US006380246B1

(12) United States Patent
Lieb et al.

(10) Patent No.: US 6,380,246 B1
(45) Date of Patent: Apr. 30, 2002

(54) ALKYL-DIHALOGENATED PHENYL-SUBSTITUTED KETOENOLS USEFUL AS PESTICIDES AND HERBICIDES

(75) Inventors: Folker Lieb; Hermann Hagemann, both of Leverkusen; Arno Widdig, Odenthal; Michael Ruther; Reiner Fischer, both of Monheim; Thomas Bretschneider, Lohmar; Christoph Erdelen, Leichlingen; Ulrike Wachendorff-Neumann, Neuwied; Peter Dahmen, Neuss; Markus Dollinger; Hans-Joachim Santel, both of Leverkusen; Alan Graff, Köln; Wolfram Andersch, Bergisch Gladbach; Norbert Mencke, Leverkusen; Andreas Turberg, Erkrath, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/404,424

(22) Filed: Sep. 23, 1999

Related U.S. Application Data

(60) Division of application No. 08/945,664, filed on Oct. 31, 1997, now abandoned, which is a continuation-in-part of application No. PCT/EP96/01781, filed on Apr. 29, 1996.

(30) Foreign Application Priority Data

May 9, 1995 (DE) ........................................ 195 16 258
Dec. 6, 1995 (DE) ........................................ 195 45 467

(51) Int. Cl.$^7$ ........................ A61K 31/34; A01N 43/08; C07D 311/96; C07D 307/02

(52) U.S. Cl. ....................... 514/462; 514/473; 549/331; 549/477

(58) Field of Search ................................ 514/462, 473; 549/477, 331

(56) References Cited

U.S. PATENT DOCUMENTS 5,191,089 A 3/1993 Baasner et al. ............. 548/550

(List continued on next page.)

FOREIGN PATENT DOCUMENTS

DE 44 13 669 1/1995

(List continued on next page.)

*Primary Examiner*—Bruck Kifle
*Assistant Examiner*—Tamthom N. Truong
(74) *Attorney, Agent, or Firm*—Norris McLaughlin & Marcus

(57) ABSTRACT

The present invention relates to new compounds of the formula (I)

(I)

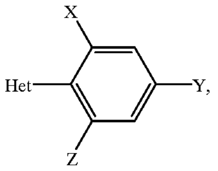

in which

X represents halogen,

Y represents halogen or alkyl and

Z represents halogen or alkyl, with the proviso that always one of the radicals Y and Z represents halogen while the other represents alkyl, and Het represents one of the groups (1)

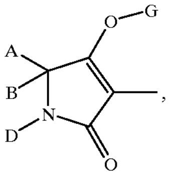

(2)

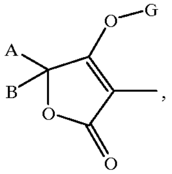

(3)

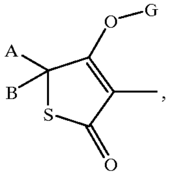

(4)

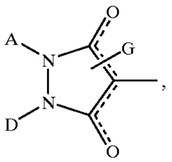

(5)

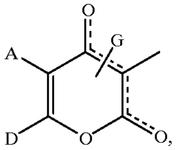

(6)

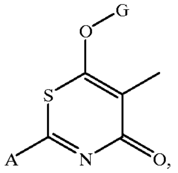

in which

A, B, D and G have the meanings given in the description, to a plurality of processes for their preparation and to their use as pesticides and herbicides.

11 Claims, No Drawings

U.S. PATENT DOCUMENTS

| | | | | |
|---|---|---|---|---|
| 5,258,527 | A | 11/1993 | Krauskopf et al. | |
| 5,262,383 | A | * 11/1993 | Fischer et al. | 504/195 |
| 5,350,861 | A | 9/1994 | Fischer et al. | 548/544 |
| 5,462,939 | A | * 10/1995 | Dolle et al. | 514/231.5 |

FOREIGN PATENT DOCUMENTS

| | | |
|---|---|---|
| EP | 0 355 599 | 2/1990 |
| EP | 0 423 482 | 4/1991 |
| EP | 0 442 077 | 8/1991 |
| EP | 0 508 126 | 10/1992 |
| EP | 0 521 334 | 1/1993 |
| EP | 0 528 156 | 2/1993 |
| EP | 0 588 137 | 3/1994 |

* cited by examiner

ALKYL-DIHALOGENATED PHENYL-SUBSTITUTED KETOENOLS USEFUL AS PESTICIDES AND HERBICIDES

This application is a division of U.S. Ser. No. 08/945,664, which was filed Oct. 31, 1997 abandonded which is a continuation-in-part of PCT/EP96/01781 filed Apr. 4, 1996.

The invention relates to new phenyl-substituted cyclic ketoenols, to a plurality of processes and intermediates for their preparation, and to their use as pesticides and herbicides.

3-Acyl-pyrrolidine-2,4-diones have already been described as having pharmaceutical properties (S. Suzuki et al. Chem. Pharm. Bull. 15 1120 (1967)). Furthermore, N-phenylpyrrolidine-2,4-diones were synthesized by R. Schmierer and H. Mildenberger (Liebigs Ann. Chem. 1985. 1095). A biological activity of these compounds has not been described.

EP-A-0 262 399 and GB-A-2 266 888 disclose compounds of a similar structure (3-aryl-pyrrolidine-2,4-diones), which, however, have not been disclosed as having a herbicidal, insecticidal or acaricidal action. Unsubstituted, bicyclic 3-aryl-pyrrolidine-2,4-dione derivatives (EP-A-355 599 and EP-A-415 211) and substituted monocyclic 3-aryl-pyrrolidine-2,4-dione derivatives (EP-A-377 893 and EP-A-442 077) having a herbicidal, insecticidal or acaricidal action are known.

Also known are polycyclic 3-arylpyrrolidine-2,4-dione derivatives (EP-A-442 073) and 1H-arylpyrrolidine-dione derivatives (EP-A-456 063, EP-A-521 334, EP-A-596 298, EP-A-613 884, EP-A-613 885, WO 94/01 997, WO 93/26954 and WO 95/01 358).

It is known that certain substituted $\Delta^3$-dihydrofuran-2-one derivatives have herbicidal properties (cf. DE-A-4 014 420). The synthesis of the tetronic acid derivatives used as starting compounds (such as, for example, 3-(2-methyl-phenyl)-4-hydroxy-5-(4-fluorophenyl)-$\Delta^3$-dihydrofuran-2-one) is also described in DE-A-4 014 420. Compounds of a similar structure are known from the publication Campbell et al., J. Chem. Soc., Perkin Trans. 1, 1985, (8) 1567–76, but no mention is made of insecticidal and/or acaricidal activity. 3-Aryl-$\Delta^3$-dihydrofuranone derivatives having herbicidal, acaricidal and insecticidal properties are furthermore known from EP-A-528 156, but the action described in this publication is not always sufficient. Thiotetronic acids are known from WO 95/26345.

Furthermore, certain 3H-pyrazole-3-one derivatives, such as, for example, 1,2-diethyl-1,2-dihydro-5-hydroxy-4-phenyl-3H-pyrazol-3-one or {[5-oxo- 1,2-diphenyl-4-(p-sulphophenyl)-3-pyrazolin-3-yl]-oxy}-disodium salt or p-(3-hydroxy-5-oxo-1,2-diphenyl-3-pyrazolin-4-yl)-benzenesulphonic acid are known from the literature (cf. J. Heterocycl. Chem., 25(5), 1301–1305, 1988 or J. Heterocycl. Chem. 25(5), 1307–1310, 1988 or Zh. Obshch. Khim., 34(7), 2397–2402, 1964). However, a biological action of these compounds is not described.

It is furthermore known that the trisodium salt of 4,4',4"-(5-hydroxy-3-oxo-1H-pyrazol-1,2,4(3H)-triyl)-tris-benzenesulphonic acid has pharmacological properties (cf. Farmakol. Toksikol. (Moscow), 38(2), 180–186, 1976). However, its use in plant protection is not known.

Moreover, 4-arylpyrazolidine-3,5-dione derivatives having herbicidal, acaricidal and insecticidal properties are described in EP-A-508 126 and in WO 92/16 510.

Certain phenyl-pyrone derivatives which are unsubstituted in the phenyl ring have already been described (cf. A. M. Chirazi, T. Kappe and E. Ziegler, Arch. Pharm. 309, 558 (1976) and K.-H. Boltze and K. Heidenbluth, Chem. Ber. 91, 2849), a potential use of these compounds as pesticides not being indicated. Phenyl-pyrone derivatives which are substituted in the phenyl ring and have herbicidal, acaricidal and insecticidal properties are described in EP-A-588 137.

Certain 5-phenyl-1,3-thiazine derivatives which are unsubstituted in the phenyl ring have already been described (cf. E. Ziegler and E. Steiner, Monatsh. 95, 147 (1964), R. Ketcham, T. Kappe and E. Ziegler, J. Heterocycl. Chem. 10, 223 (1973)), a potential use of these compounds as pesticides not being indicated. 5-Phenyl-1,3-thiazine derivatives which are substituted in the phenyl ring and have a herbicidal, acaricidal and insecticidal action are described in WO 94/14 785.

However, the activity and spectrum of action of these compounds are not always entirely satisfactory, in particular at low application rates and concentrations. Furthermore, the tolerance, by plants, of the known compounds is not always sufficient.

There have now been found new compounds of the formula (I)

(I)

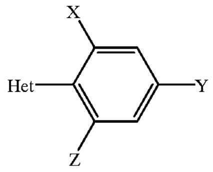

in which

X represents halogen,

Y represents halogen or alkyl and

Z represents halogen or alkyl, with the proviso that always one of the radicals Y and Z represents halogen and the other represents alkyl, Het represents one of the groups (1)

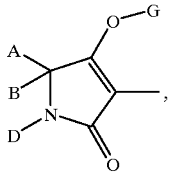

(2)

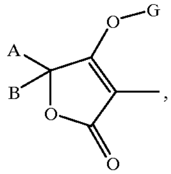

(3)

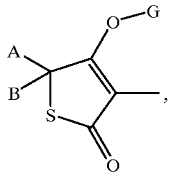

-continued (4)

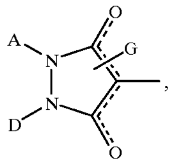

(5)

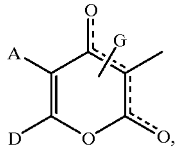

(6)

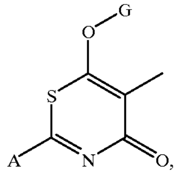

in which

A represents hydrogen, or represents alkyl, alkenyl, alkoxyalkyl, polyalkoxyalkyl or alkylthioalkyl, each of which is optionally substituted by halogen, or represents in each case saturated or unsaturated and optionally substituted cycloalkyl or heterocyclyl, or represents aryl, arylalkyl or hetaryl, each of which is optionally substituted by halogen, alkyl, halogenoalkyl, alkoxy, halogenoalkoxy, cyano or nitro, B represents hydrogen, alkyl or alkoxyalkyl, or A and B together with the carbon atom to which they are bonded represent a saturated or unsaturated, optionally substituted carbocycle or heterocycle, D represents hydrogen or an optionally substituted radical from the series consisting of alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or A and D together with the atoms to which they are bonded represent a saturated or unsaturated and optionally substituted carbocycle or heterocycle, G, in the event that Het represents one of the radicals (1), (2), (3), (5) or (6), represents hydrogen (a) or, in the event that Het represents one of the radicals (1), (2), (3), (4), (5) or (6), represents one of the groups (b)

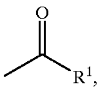

(c)

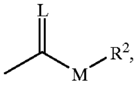

(d)

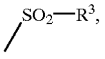

(e)

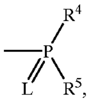

(f)

E or

-continued (g)

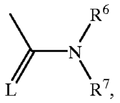

in which

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, each of which is optionally substituted by halogen, or represents cycloalkyl or heterocyclyl, each of which is optionally substituted by halogen, alkyl or alkoxy, or represents in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, each of which is optionally substituted by halogen, or represents in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, each of which is optionally substituted by halogen, or in each case represent optionally substituted phenyl, benzyl, phenoxy or phenylthio, $R^6$ and $R^7$ independently of one another represent hydrogen, or represent alkyl, cycloalkyl, alkenyl, alkoxy or alkoxyalkyl, each of which is optionally substituted by halogen, or represent in each case optionally substituted phenyl or benzyl, or together with the N atom to which they are bonded represent an optionally substituted cycle which optionally contains oxygen or sulphur.

Depending on the nature of the substituents, the compounds of the formula (I) can exist as geometric and/or optical isomers or variously composed isomer mixtures which, if desired, can be separated in the customary manner. The pure isomers and the isomer mixtures, their preparation and their use, and the compositions comprising them are all objects of the present invention. For the sake of simplicity, however, the following text will always mention compounds of the formula (I), even though this is to be understood as meaning the pure compounds and, if appropriate, also mixtures containing various proportions of isomeric compounds.

Taking into consideration the meanings (1) to (6) of the group Het, the following main structures (I-1) to (I-6) result:

(I-1)

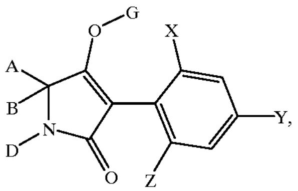

-continued
(I-2)
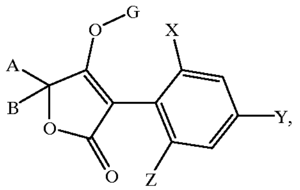
(I-3)
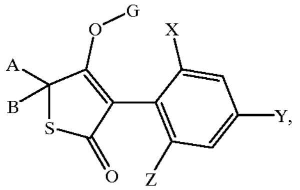
(I-4)
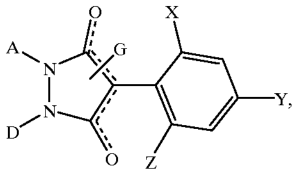
(I-5)
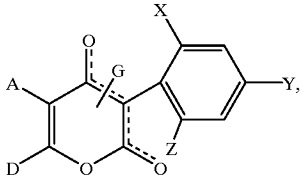
(I-6)
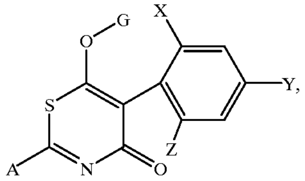
in which
A, B, D, G, X, Y and Z have the abovementioned meanings.
Taking into consideration the various meanings (a), (b), (c), (d), (e), (f) and (g) of group G, the following main structures (I-1-a) to (I-1-g) result if Het represents the group (1):
(I-1-a):
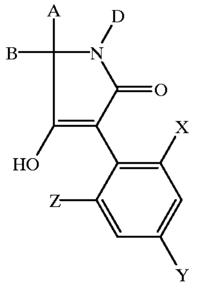
-continued
(I-1-b):
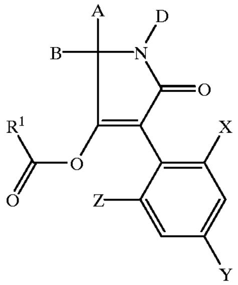
(I-1-c):
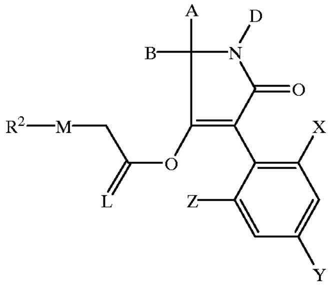
(I-1-d):
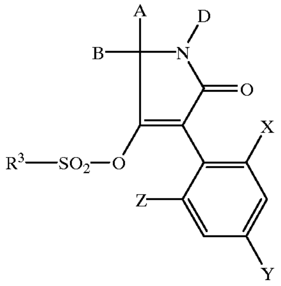
(I-1-e):
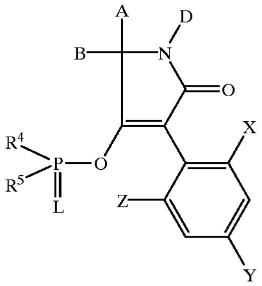
(I-1-f):
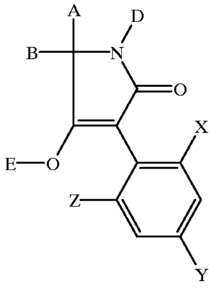

-continued (I-1-g):

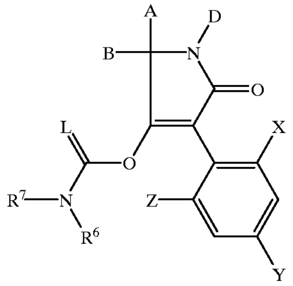

in which

A, B, D, E, L, M, X, Y, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-2-a) to (I-2-g) result if Het represents the group (2):

(I-2-a):

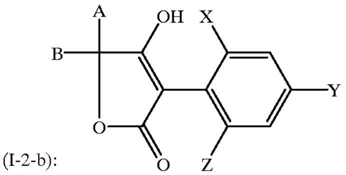

(I-2-b):

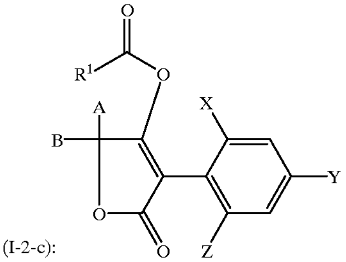

(I-2-c):

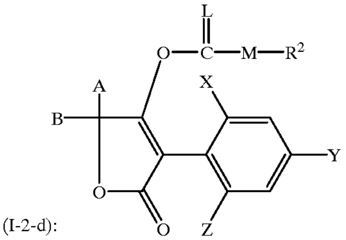

(I-2-d):

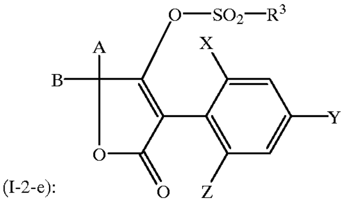

(I-2-e):

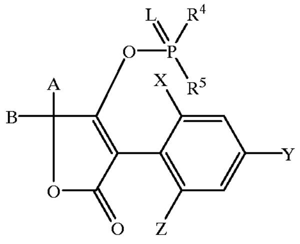

-continued (I-2-f):

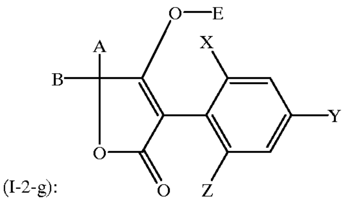

(I-2-g):

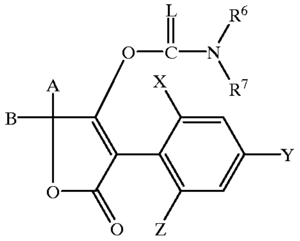

in which

A, B, E, L, M, X, Y, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-3-a) to (I-3-g) result if Het represents the group (3):

(I-3-a):

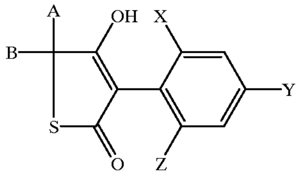

(I-3-b):

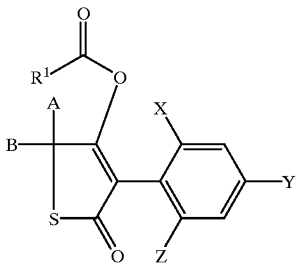

(I-3-c):

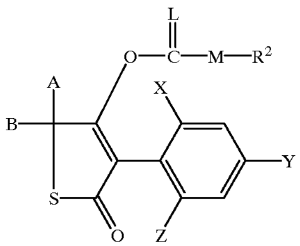

(I-3-d):

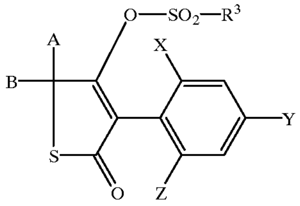

-continued (I-3-e):

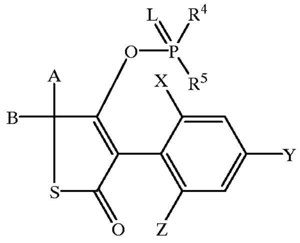

(I-3-f):

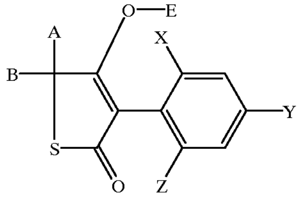

(I-3-g):

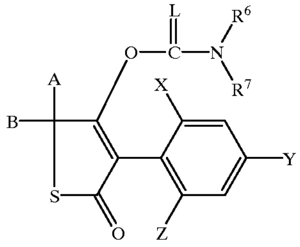

in which

A, B, E, L, M, X, Y, Z, $R^1$, $R^2$, $R^3$, $R^4$, $R^5$, $R^6$ and $R^7$ have the abovementioned meanings.

Depending on the position of the substituent G, the compounds of the formula (I-4) can exist in the two isomeric forms of the formulae $(I-4)_a$ and $(I-4)_b$ $(1-4)_a$

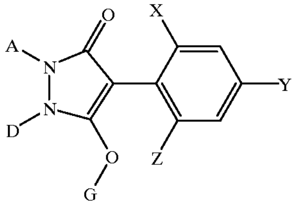

$(1-4)_{b'}$

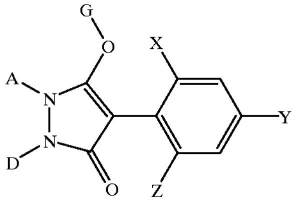

which is indicated by the broken line in formula (I-4).

The compounds of the formulae $(I-4)_a$ and $(I-^4)_b$ can exist as mixtures and also in the form of their pure isomers. If appropriate, mixtures of the compounds of the formulae $(I-4)_a$ and $(I-^4)_b$ can be separated by physical methods in a manner known per se, for example by chromatographic methods.

For reasons of clarity, only one of the isomers which are possible in each case will be given in the following text. This does not exclude that, if appropriate, the compounds may exist in the form of the isomer mixtures or in the respective other isomeric form.

Taking into consideration the various meanings (b), (c), (d), (e), (f) and (g) of group G, the following main structures (I-4-b) to (I-4-g) result if Het represents the group (4):

(I-4-b):

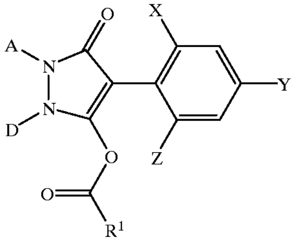

(I-4-c):

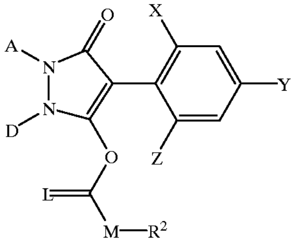

(I-4-d):

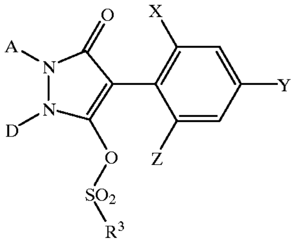

(I-4-e):

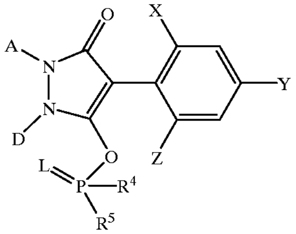

(I-4-f):

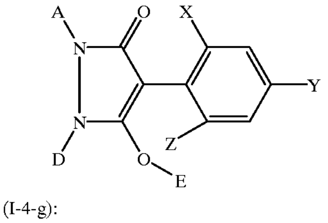

(I-4-g):

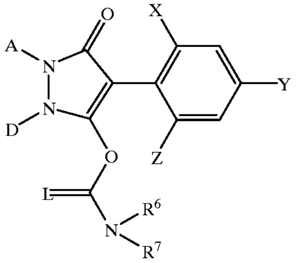

in which

A, D, E, L, M, X, Y, Z, $R^1$, $R^2$, $R^3$, $R^4$, $R^5$, $R^6$ and $R^7$ have the abovementioned meanings.

Depending on the position of the substituent G, the compounds of the formula (I-5) can exist in the two isomeric forms of the formulae $(I\text{-}5)_a$ and $(I\text{-}^5)_b$ $(I\text{-}5)_a$

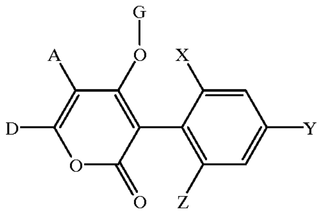

$(I\text{-}5)_b$

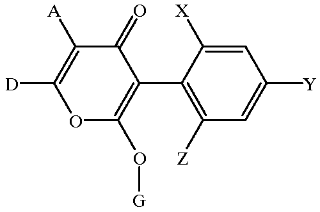

which is indicated by the broken line in formula (I-5).

The compounds of the formulae $(I\text{-}5)_a$ and $(I\text{-}5)_b$ can exist as mixtures and also in the form of their pure isomers. If appropriate, mixtures of the compounds of the formulae $(I\text{-}5)_a$ and $(I\text{-}5)_b$ can be separated by physical methods in a manner known per se, for example by chromatographic methods.

For reasons of clarity, only one of the isomers which are possible in each case will be given in the following text. This does not exclude that, if appropriate, the compounds may exist in the form of the isomer mixtures or in the respective other isomeric form.

Taking into consideration the various meanings (a), (b), (c), (d), (e), (f) and (g) of group G, the following main structures (I-5-a) to (I-5-g) result if Het represents the group (5):

(I-5-a):

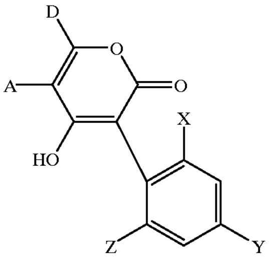

(I-5-b):

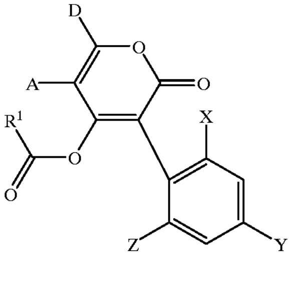

-continued (I-5-c):

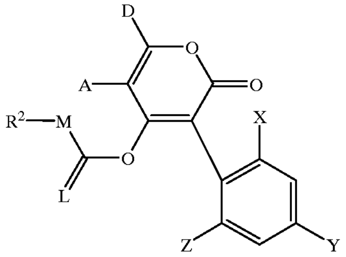

(I-5-d):

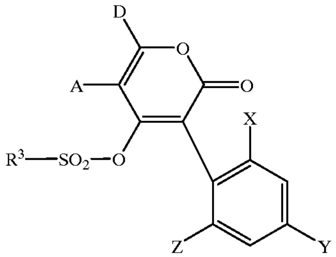

(I-5-e):

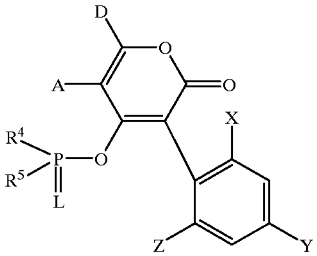

(I-5-f):

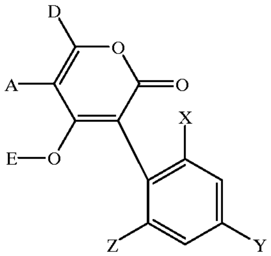

(I-5-g):

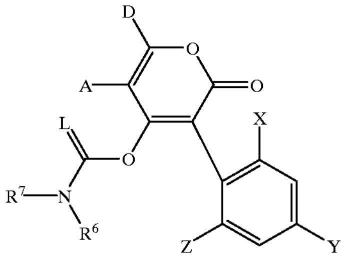

in which

A, D, E, L, M, X, Y, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-6-a) to (I-6-g) result if Het represents the group (6):

(I-6-a):

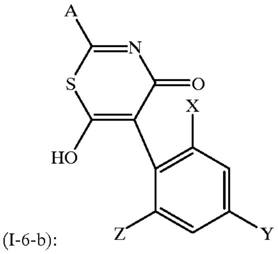

(I-6-b):

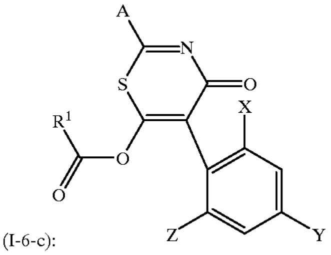

(I-6-c):

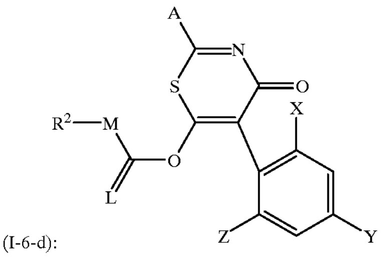

(I-6-d):

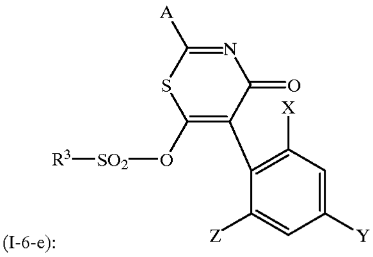

(I-6-e):

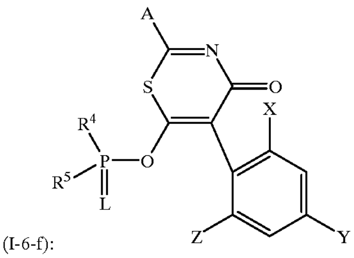

(I-6-f):

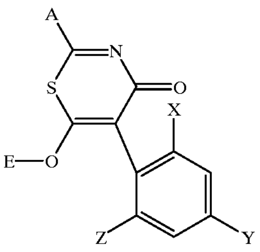

-continued (I-6-g):

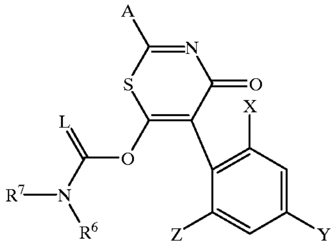

in which

A, E, L, M, X, Y, Z, $R^1$, $R^2$, $R^3$, $R^4$, $R^5$, $R^6$ and $R^7$ have the abovementioned meanings.

Furthermore, it has been found that the new compounds of the formula (I) are obtained by one of the processes described below:

(A) Compounds of the formula (I-1-a)

(I-1-a)

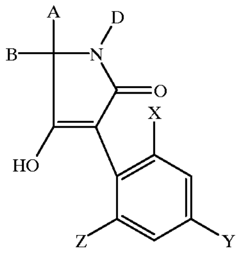

in which

A, B, D, X, Y and Z have the abovementioned meanings, are obtained when compounds of the formula (II)

(II)

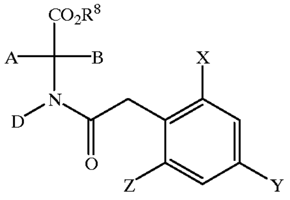

in which

A, B, D, X, Y and Z have the abovementioned meanings and $R^8$ represents alkyl (preferably $C_1$–$C_6$-alkyl), are subjected to intramolecular condensation in the presence of a diluent and in the presence of a base.

B) Furthermore, it has been found that compounds of the formula (I-2-a)

(I-2-a)

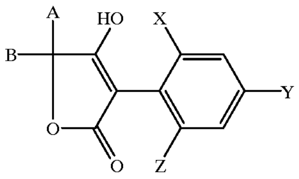

in which

A, B, X, Y and Z have the abovementioned meanings, are obtained when compounds of the formula (III)

(III)

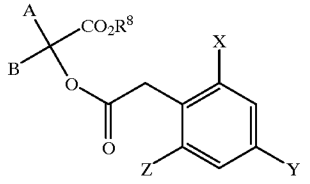

in which

A, B, X, Y, Z and $R^8$ have the abovementioned meanings, are subjected to intramolecular condensation in the presence of a diluent and in the presence of a base.

(C) Furthermore, it has been found that compounds of the formula (I-3-a)

(I-3-a)

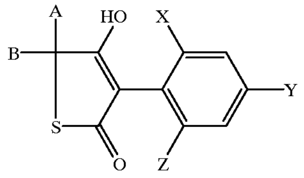

in which

A, B, X, Y and Z have the abovementioned meanings, are obtained when compounds of the formula (IV)

(IV)

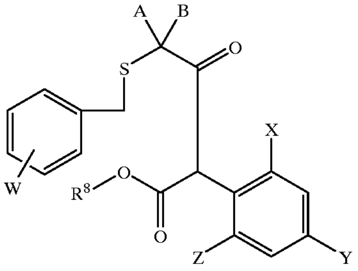

in which

A, B, X, Y, Z and $R^8$ have the abovementioned meanings and

W represents hydrogen, halogen, alkyl (preferably $C_1$–$C_6$-alkyl) or alkoxy (preferably $C_1$–$C_8$-alkoxy), are subjected to intramolecular cyclization, if appropriate in the presence of a diluent and in the presence of an acid.

(E) Furthermore, it has been found that the compounds of the formula (I-5-a)

(I-5-a)

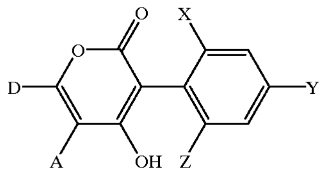

in which

A, D, X, Y and Z have the abovementioned meanings are obtained when compounds of the formula (VIII)

(VIII)

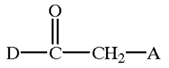

in which

A and D have the abovementioned meanings or their silyl enol ethers of the formula (VIIIa)

(VIIIa)

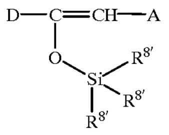

in which

A and D have the abovementioned meanings and $R^{8'}$ represents alkyl (preferably methyl)

are reacted with compounds of the formula (V)

(V)

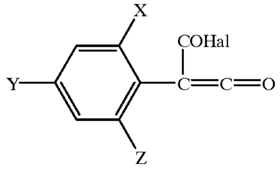

in which

X, Y and Z have the abovementioned meanings and

Hal represents halogen (preferably chlorine or bromine), if appropriate in the presence of a diluent and if appropriate in the presence of an acid acceptor.

(F) Furthermore, it has been found that the compounds of the formula (I-6-a)

(I-6-a)

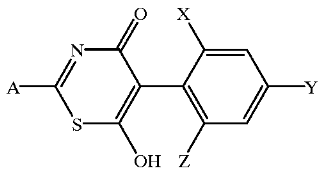

in which

A, X, Y and Z have the abovementioned meanings, are obtained when compounds of the formula (IX)

(IX)

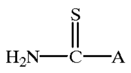

in which

A has the abovementioned meaning, are reacted with compounds of the formula (V)

(V)

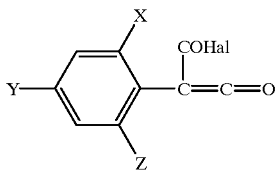

in which

Hal, X, Y and Z have the abovementioned meanings, if appropriate in the presence of a diluent and if appropriate in the presence of an acid acceptor.

Moreover, it has been found (G) that the compounds of the formulae (I-1-b) to (I-3-b), (I-5-b) and (I-6-b) shown above in which A, B, D, $R^1$, X, Y and Z have the abovementioned meanings are obtained when compounds of the formulae (I-1-a) to (I-3-a), (I-5-a) and (I-6-a) shown above in which A, B, D, X, Y and Z have the abovementioned meanings, and that compounds of the formulae (I-4-b) shown above in which A, D, $R^1$, X, Y and Z have the abovementioned meanings are obtained when compounds of the formula (I-4-a)

(I-4-a)

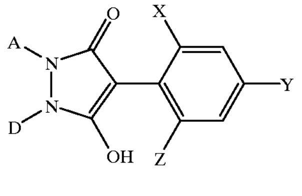

in which

A, D, X, Y and Z have the abovementioned meanings are in each case reacted

α) with acid halides of the formula (X)

(X)

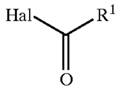

in which $R^1$ has the abovementioned meaning and

Hal represents halogen (in particular chlorine or bromine) or

β) with carboxylic anhydrides of the formula (XI)

$R^1—CO—O—CO—R^1$ (XI)

in which $R^1$ has the abovementioned meaning, if appropriate in the presence of a diluent and if appropriate in the presence of an acid-binding agent;

(H) that the compounds of the formulae (I-1-c) to (I-6-c) shown above in which A, B, D, $R^2$, M, X, Y and Z have the abovementioned meanings and L represents oxygen are obtained when compounds of the formulae (I-1-a) to (I-6-a) shown above in which A, B, D, X, Y and Z have the abovementioned meanings are reacted in each case with chloroformic esters or chloroformic thioesters of the formula (XII)

$R^2—M—CO—Cl$ (XII)

in which $R^2$ and M have the abovementioned meanings, if appropriate in the presence of a diluent and if appropriate in the presence of an acid-binding agent;

(I) that compounds of the formulae (I-1-c) to (I-6-c) shown above in which A, B, D, $R^2$, M, X, Y and Z have the abovementioned, meanings and L represents sulphur are obtained when compounds of the formulae (I-1-a) to (I-6-a) shown above in which A, B, D, X, Y and Z have the abovementioned meanings are reacted in each case α) with chloromonothioformic esters or chlorodithioformic esters of the formula (XIII)

(XIII)

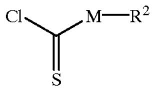

in which

M and $R^2$ have the abovementioned meanings, if appropriate in the presence of a diluent and if appropriate in the presence of an acid-binding agent, or β) with carbon disulphide and subsequently with compounds of the formula (XIV)

$R^2—Hal$ (XIV)

in which $R^2$ has the abovementioned meaning and

Hal represents chlorine, bromine or iodine, if appropriate in the presence of a diluent and if appropriate in the presence of a base, (J) that compounds of the formulae (I-1-d) to (I-6-d) shown above in which A, B, D, $R^3$, X, Y and Z have the abovementioned meanings are obtained when compounds of the formulae (I-1-a) to (I-6-a) shown above in which A, B, D, X, Y and Z have the abovementioned meanings are reacted in each case with sulphonyl chlorides of the formula (XV)

$R^3—SO_2—Cl$ (XV)

in which $R^3$ has the abovementioned meaning;

if appropriate in the presence of a diluent and if appropriate in the presence of an acid-binding agent, (K) that compounds of the formulae (I-1-e) to (I-6-e) shown above in which A, B, D, L, $R^4$, $R^5$, X, Y and Z have the abovementioned meanings are obtained when compounds of the formulae (I-1-a) to (I-6-a) shown above in which A, B, D, X, Y and Z have the abovementioned meanings are reacted in each case with phosphorus compounds of the formula (XVI)

(XVI)

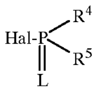

in which

L, $R^4$ and $R^5$ have the abovementioned meanings and

Hal represents halogen (in particular chlorine or bromine), if appropriate in the presence of a diluent and if appropriate in the presence of an acid-binding agent, (L) that compounds of the formulae (I-1-f) to (I-6-f) shown above in which A, B, D, E, X, Y and Z have the abovementioned meanings are obtained when compounds of the formulae (I-1-a) to (I-6-a) in which A, B, D, X, Y and Z have the abovementioned meanings are reacted in each case with metal compounds or amines of the formulae (XVII) or (XVIII)

$Me(OR^{10})_t$ (XVII)

(XVIII)

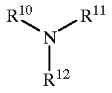

in which

Me represents a mono- or divalent metal (preferably an alkali metal or alkaline earth metal, such as lithium, sodium, potassium, magnesium or calcium), t represents the number 1 or 2 and $R^{10}$, $R^{11}$ and $R^{12}$ independently of one another represent hydrogen or alkyl (preferably $C_1$–$C_8$-alkyl), if appropriate in the presence of a diluent, (M) that compounds of the formulae (I-1-g) to (I-6-g) shown above in which A, B, D, L, $R^6$, $R^7$, X, Y and Z have the abovementioned meanings are obtained when compounds of the formulae (I-1-a) to (I-6-a) shown above in which A, B, D, X, Y and Z have the abovementioned meanings are reacted in each case α) with isocyanates or isothiocyanates of the formula (XIX)

$$R^6—N=C=L \qquad (XIX)$$

in which $R^6$ and L have the abovementioned meanings, if appropriate in the presence of a diluent and if appropriate in the presence of a catalyst, or β) with carbamoyl chlorides or thiocarbamoyl chlorides of the formula (XX)

(XX)

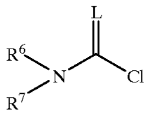

in which

L, $R^6$ and $R^7$ have the abovementioned meanings, if appropriate in the presence of a diluent and if appropriate in the presence of an acid-binding agent.

Furthermore, it has been found that the new compounds of the formula (I) have a very good activity as pesticides, preferably as insecticides, acaricides and also as herbicides.

Formula (I) provides a general definition of the compounds according to the invention. Preferred substituents or ranges of the radicals listed in the formulae mentioned hereinabove and hereinbelow are illustrated in the following text:

X preferably represents halogen.

Y preferably represents halogen or $C_1$–$C_6$-alkyl.

Z preferably represents halogen or $C_1$–$C_6$-alkyl.

One of the substituents Y and Z always represents halogen, while the other represents alkyl.

Het preferably represents one of the groups (1)

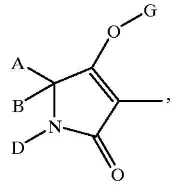

(2)

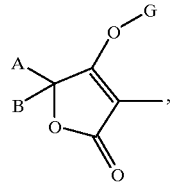

(3)

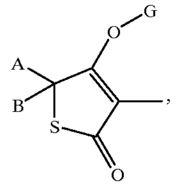

(4)

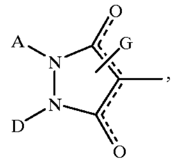

(5)

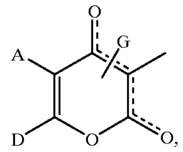

(6)

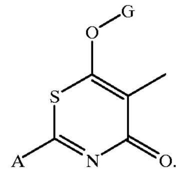

A preferably represents hydrogen, or represents $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl, naphthyl, phenyl-$C_1$–$C_6$-alkyl, naphthyl-$C_1$–$C_6$-alkyl or -hetaryl having 5 or 6 ring atoms and one to three hetero atoms from the series consisting of oxygen, sulphur and nitrogen, in each case optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro.

B preferably represents hydrogen, $C_1$–$C_{12}$-alkyl or $C_1$–$C_8$-alkoxy-$C_1$–$C_6$-alkyl, or A, B and the carbon atom to which they are bonded preferably represent $C_3$–$C_{10}$-cycloalkyl or $C_5$–$C_{10}$-cycloalkenyl in each of which a methylene group is optionally replaced by oxygen or sulphur and which are optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are bonded preferably represent $C_5$–$C_6$-cycloalkyl which is substituted by an alkylenediyl group which optionally contains one or two oxygen and/or sulphur atoms or by an alkylenedioxy or by an alkylenedithioyl group, this group, together with the carbon atom to which it is bonded forming a further five to eight-membered ring, or A, B and the carbon atom to which they are bonded preferably represent $C_3$–$C_8$-cycloalkyl or $C_5$–$C_8$-cycloalkenyl in which two substituents together with the carbon atoms to which they are bonded represent $C_3$–$C_6$-alkanediyl, $C_3$–$C_6$-alkenediyl or $C_4$–$C_6$-alkanedienediyl, each of which is optionally substituted by $C_1$–$C_6$-alkyl, $C_1$–$C_6$-alkoxy or halogen and in which in each case one methylene group is optionally replaced by oxygen or sulphur.

D preferably represents hydrogen, or represents $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1C_{10}$-alkylthio-$C_2$–$C_8$-alkyl, each of which is optionally substituted by halogen, or represents $C_3$–$C_8$-cycloalkyl which is optionally substituted by halogen, $C_1$–$C_4$-alkyl, $C_1$–$C_4$-alkoxy or $C_1$–$C_4$-halogenoalkyl and in which one or two methylene groups which are not directly adjacent are optionally replaced by oxygen and/or sulphur, or represents phenyl, hetaryl having 5 to 6 ring atoms and one or two hetero atoms from the series consisting of oxygen, sulphur and nitrogen, phenyl-$C_1$–$C_6$-alkyl or hetaryl-$C_1$–$C_6$-alkyl having 5 to 6 ring atoms and one or two hetero atoms from the series consisting of oxygen, sulphur and nitrogen, in each case optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together preferably represent a $C_3$–$C_6$-alkanediyl, $C_3$-$C_6$-alkenediyl or $C_4$–$C_6$-alkanedienediyl group in each of which one methylene group is optionally replaced by oxygen or sulphur and which is in each case optionally substituted by halogen, hydroxyl, mercapto, or by $C_1$–$C_{10}$-alkyl, $C_1$–$C_6$-alkoxy, $C_1$–$C_6$-alkylthio, $C_3$–$C_7$-cycloalkyl, phenyl or benzyloxy, each of which is optionally substituted by halogen, or by a further $C_3$–$C_6$-alkanediyl, $C_3$–$C_6$-alkenediyl or $C_4$–$C_6$-alkanedienediyl group which forms a fused ring and in each of which one methylene group is optionally replaced by oxygen or sulphur and which is optionally substituted by $C_1$–$C_6$-alkyl or in which two adjacent substituents together with the carbon atoms to which they are bonded optionally form a further saturated or unsaturated carbocycle having 5 or 6 ring atoms, or A and D together represent a $C_3$–$C_6$-alkanediyl or $C_3$–$C_6$-alkenediyl group in each of which one of the following groups

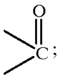 ; 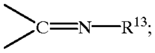 ; 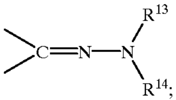 ;

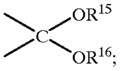 ; 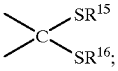 ; 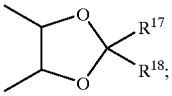 ;

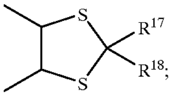 ; 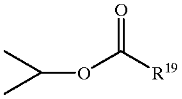 or

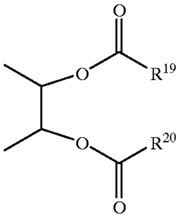

is optionally present.

G preferably, in the event that Het represents one of the radicals (1), (2), (3), (5) or (6), represents hydrogen (a) or, in the event that Het represents one of the radicals (1), (2), (3), (4), (5) or (6), represents one of the groups (b)

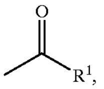

(c)

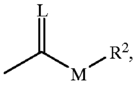

(d)

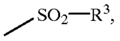

(e)

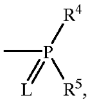

(f)

E or (g)

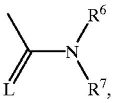

in which

E represents a metal ion equivalent or an ammonium ion,

L represents oxygen or sulphur and

M represents oxygen or sulphur.

$R^1$ preferably represents $C_1$–$C_{20}$-alkyl, $C_2$–$C_{20}$-alkenyl, $C_1$–$C_9$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents 5- or 6-membered hetaryl having one or two hetero atoms from the series consisting of oxygen, sulphur and nitrogen which is optionally substituted by halogen or $C_1$–$C_6$-alkyl, or represents phenoxy-$C_1$–$C_6$-alkyl which is optionally substituted by halogen or $C_1$–$C_6$-alkyl, or represents 5- or 6-membered hetaryloxy-$C_1$–$C_6$-alkyl having one or two hetero atoms from the series consisting of oxygen, sulphur and nitrogen which is optionally substituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy, or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents $C_1$–$C_8$-alkyl which is optionally-substituted by halogen, or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_2$–$C_8$-alkenylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, each of which is optionally substituted by halogen, or represent phenyl or benzyl, each of which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical which is optionally substituted by $C_1$–$C_6$-alkyl and in which one methylene group is optionally replaced by oxygen or sulphur.

$R^{13}$ preferably represents hydrogen, or represents $C_1$–$C_8$-alkyl or $C_1$–$C_8$-alkoxy, each of which is optionally substituted by halogen, or represents $C_3$–$C_8$-cycloalkyl which is optionally substituted by halogen, $C_1$–$C_4$-alkyl or $C_1$–$C_4$-alkoxy and in which one methylene group is optionally replaced by oxygen or sulphur, or represents phenyl, phenyl-$C_1$–$C_4$-alkyl or phenyl-$C_1$–$C_4$-alkoxy, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^{14}$ preferably represents hydrogen or $C_1$–$C_8$-alkyl or $R^{13}$ and $R^{14}$ together preferably represent $C_4$–$C_6$-alkanediyl.

$R^{15}$ and $R^{16}$ are identical or different and preferably represent $C_1$–$C_6$-alkyl or $R^{15}$ and $R^{16}$ together preferably represent a $C_2$–$C_4$-alkanediyl radical which is optionally substituted by $C_1$–$C_6$-alkyl or by phenyl which is optionally substituted by halogen, $C_1$–$C_4$-alkyl, $C_1$–$C_4$-halogenoalkyl, $C_1$–$C_4$-alkoxy, $C_1$–$C_4$-halogenoalkoxy, nitro or cyano.

$R^{17}$ and $R^{18}$ independently of one another preferably represent hydrogen, or represent $C_1$–$C_8$-alkyl which is optionally substituted by halogen, or represent phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or $R^{17}$ and $R^{18}$ together with the carbon atom to which they are bonded represent $C_5$–$C_7$-cycloalkyl which is optionally substituted by $C_1$–$C_4$-alkyl or $C_1$–$C_4$-alkoxy and in which one methylene group is optionally replaced by oxygen or sulphur.

$R^{19}$ and $R^{20}$ independently of one another preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

X particularly preferably represents fluorine, chlorine or bromine.

Y particularly preferably represents fluorine, chlorine, bromine or $C_1$–$C_4$-alkyl.

Z particularly preferably represents fluorine, chlorine, bromine or $C_1$–$C_4$-alkyl.

One of the radicals Y and Z always represents halogen while the other represents alkyl.

Het particularly preferably represents one of the groups (1)

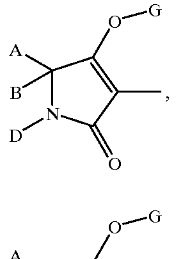

(2)

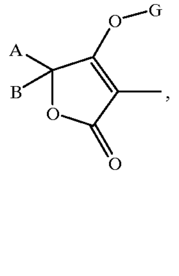

-continued (3)

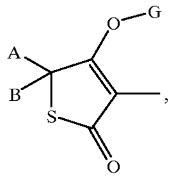

(4)

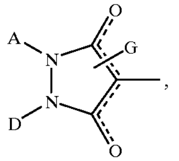

(5)

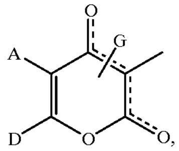

(6)

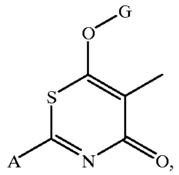

A particularly preferably represents hydrogen, or represents $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl, each of which is optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy and in which one or two methylene groups which are not directly adjacent are optionally replaced by oxygen and/or sulphur, or represents phenyl, furanyl, pyridyl, imidazolyl, triazolyl, pyrazolyl, indolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro.

B particularly preferably represents hydrogen, $C_1$–$C_{10}$-alkyl or $C_1$–$C_6$-alkoxy-$C_1$–$C_4$-alkyl, or A, B and the carbon atom to which they are bonded particularly preferably represent $C_3$–$C_8$-cycloalkyl or $C_5$–$C_8$-cycloalkenyl in each of which one methylene group is optionally replaced by oxygen or sulphur and which are optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are bonded particularly preferably represent $C_5$–$C_6$-cycloalkyl which is substituted by an alkylenediyl group which optionally contains one or two oxygen or sulphur atoms or by an alkylenedioxy or by an alkylenedithioyl group, this group, together with the carbon atom to which it is bonded forming a further five to seven-membered ring, or A, B and the carbon atom to which they are bonded particularly preferably represent $C_3$–$C_6$-cycloalkyl or $C_5$–$C_6$-cycloalkenyl in which two substituents together with the carbon atoms to which they are bonded represent $C_3$–$C_5$-alkanediyl, $C_3$–$C_5$-alkenediyl or butadienediyl, each of which is optionally substituted by $C_1$–$C_5$-alkyl, $C_1$–$C_5$-alkoxy, fluorine, chlorine or bromine and in which in each case one methylene group is optionally replaced by oxygen or sulphur.

D particularly preferably represents hydrogen, or represents $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine, or represents $C_3$–$C_7$-cycloalkyl which is optionally substituted by fluorine, chlorine, $C_1$–$C_4$-alkyl, $C_1$–$C_4$-alkoxy or $C_1$—$C_2$-halogenoalkyl and in which one or two methylene groups which are not directly adjacent are optionally replaced by oxygen and/or sulphur, or represents phenyl, furanyl, imidazolyl, pyridyl, thiazolyl, pyrazolyl, pyrimidyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together particularly preferably represent a $C_3$–$C_5$-alkanediyl or $C_3$–$C_5$-alkenediyl group in each of which one methylene group is optionally replaced by oxygen or sulphur and which are optionally substituted by fluorine, chlorine, hydroxyl, mercapto, or by $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or in which in each case one of the following groups

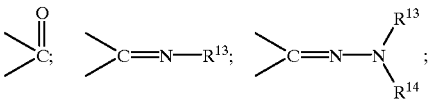

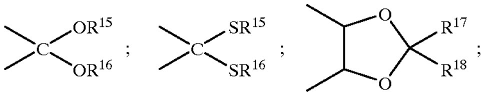

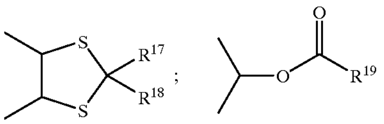

or

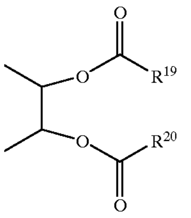

is optionally present;

or A and D (in the case of the compounds of the formula (I-1)) together with the atoms to which they are bonded represent one of the groups AD-1 to AD-27

AD-1
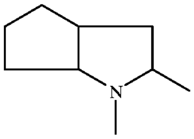
AD-2
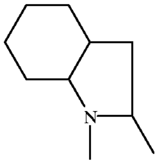
AD-3
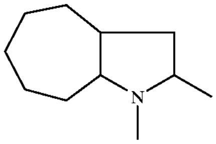
AD-4
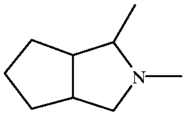
AD-5
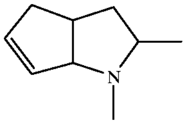
AD-6
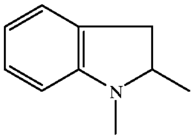
AD-7
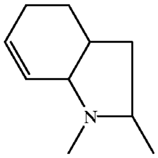
AD-8
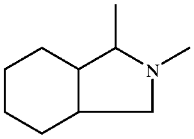
AD-9
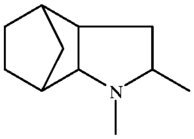
AD-10
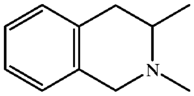
-continued
AD-11
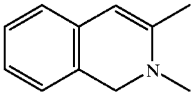
AD-12
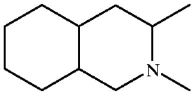
AD-13
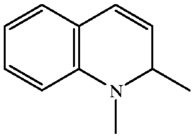
AD-14
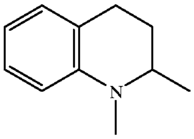
AD-15
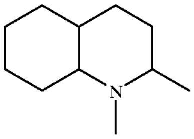
AD-16
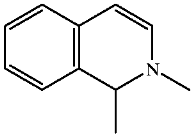
AD-17
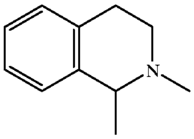
AD-18
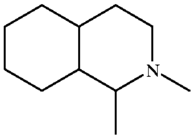
AD-19
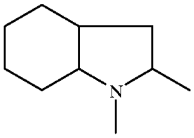
AD-20
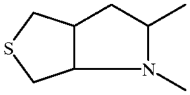
AD-21
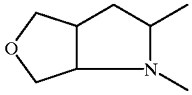

-continued

AD-22

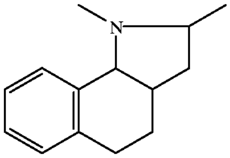

AD-23

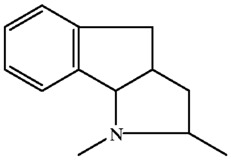

AD-24

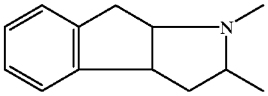

AD-25

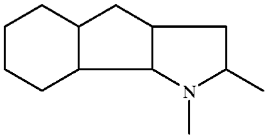

AD-26

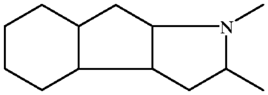

AD-27

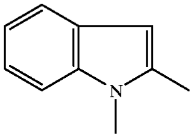

G particularly preferably, in the event that Het represents one of the radicals (1), (2), (3), (5) or (6), represents hydrogen (a) or, in the event that Het represents one of the radicals (1), (2), (3), (4), (5) or (6), represents one of the groups (b)

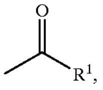

(c)

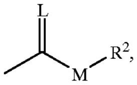

(d)

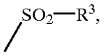

(e)

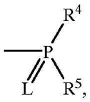

(f)

E

-continued or (g)

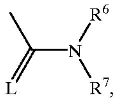

in which

E represents a metal ion equivalent or an ammonium ion,

L represents oxygen or sulphur and

M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_{1-C6}$-alkyl, each of which is optionally substituted by fluorine or chlorine, or represents $C_3$–$C_7$-cycloalkyl which is optionally substituted by fluorine, chlorine, $C_1$–$C_5$-alkyl or $C_1$–$C_5$-alkoxy and in which one or two methylene groups which are not directly adjacent are optionally replaced by oxygen and/or sulphur, or represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyrazolyl, thiazolyl, pyridyl, pyrimidyl, furanyl or thienyl, each of which is optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy, or represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents $C_1$–$C_6$-alkyl which is optionally substituted by fluorine or chlorine, or represents phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro.

$R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or represent phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical which is optionally substituted by $C_1$–$C_4$-alkyl and in which one methylene group is optionally replaced by oxygen or sulphur.

$R^{13}$ particularly preferably represents hydrogen, or represents $C_1$–$C_6$-alkyl or $C_1$–$C_6$-alkoxy, each of which is optionally substituted by fluorine or chlorine, or represents $C_3$–$C_7$-cycloalkyl which is optionally substituted by fluorine, $C_1$–$C_2$-alkyl or $C_1$–$C_2$-alkoxy and in which one methylene group is optionally replaced by oxygen or sulphur, or represents phenyl, phenyl-$C_1$–$C_3$-alkyl or phenyl-$C_1$–$C_2$-alkoxy, each of which is optionally substituted by fluorine, chlorine, bromine, $C_1$–$C_5$-alkyl, $C_1$–$C_5$-alkoxy, $C_1$–$C_2$-halogenoalkyl, $C_1$–$C_2$-halogenoalkoxy, nitro or cyano.

$R^{14}$ particularly preferably represents hydrogen or $C_1$–$C_6$-alkyl or $R^{13}$ and $R^{14}$ together particularly preferably represent $C_4$–$C_6$-alkanediyl.

$R^{15}$ and $R^{16}$ are identical or different and particularly preferably represent $C_1$–$C_4$-alkyl or $R^{15}$ and $R^{16}$ together particularly preferably represent a $C_2$–$C_3$-alkanediyl radical which is optionally substituted by $C_1$–$C_4$-alkyl or by phenyl which is optionally substituted by fluorine, chlorine, bromine, $C_1$–$C_2$-alkyl, $C_1$–$C_2$-halogenoalkyl, $C_1$–$C_2$-alkoxy, $C_1$–$C_2$-halogenoalkoxy, nitro or cyano.

$R^{17}$ and $R^{18}$ independently of one another particularly preferably represent hydrogen, or represent $C_1$–$C_8$-alkyl which is optionally substituted by fluorine or chlorine, or represent phenyl which is optionally substituted by fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro or cyano, or $R^{17}$ and $R^{18}$ particularly preferably together with the carbon atom to which they are bonded represent $C_5$–$C_6$-cycloalkyl which is optionally substituted by $C_1$–$C_3$-alkyl or $C_1$–$C_3$-alkoxy and in which one methylene group is optionally replaced by oxygen or sulphur.

$R^{19}$ and $R^{20}$ independently of one another particularly preferably represent $C_1$–$C_6$-alkyl, $C_2$–$C_6$-alkenyl, $C_1$–$C_6$-alkoxy, $C_1$–$C_6$-alkylamino, $C_3$–$C_6$-alkenylamino, di-($C_1$–$C_6$-alkyl)amino or di-($C_3$–$C_6$-alkenyl)amino.

X very particularly preferable represents fluorine, chlorine or bromine.

Y very particularly preferably represents fluorine, chlorine, bromine, methyl, ethyl, n-propyl or isopropyl.

Z very particularly preferably represents fluorine, chlorine, bromine, methyl, ethyl, n-propyl or isopropyl.

One of the radicals Y and Z always represents halogen while the other represents alkyl.

Het very particularly preferably represents one of the groups (1)

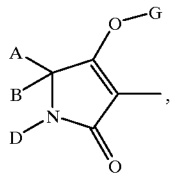

(2)

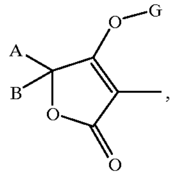

(3)

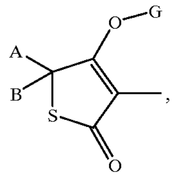

(4)

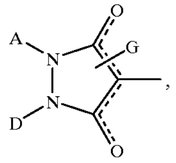

(5)

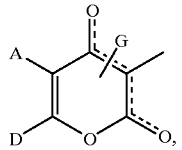

(6)

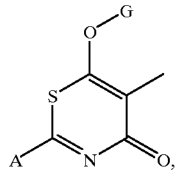

A very particularly preferably represents hydrogen, or represents $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, each of which is optionally substituted by fluorine or chlorine, or represents $C_3$–$C_6$-cycloalkyl which is optionally substituted by fluorine, chlorine, methyl or methoxy and in which one or two methylene groups which are not directly adjacent are optionally replaced by oxygen and/or sulphur, or represents phenyl, pyridyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro.

B very particularly preferably represents hydrogen, $C_1$–$C_8$-alkyl or $C_1$–$C_4$-alkoxy-$C_1$–$C_2$-alkyl, or A, B and the carbon atom to which they are bonded very particularly preferably represent $C_3$–$C_8$-cycloalkyl or $C_5$–$C_8$-cycloalkenyl in each of which one methylene group is optionally replaced by oxygen or sulphur and which are optionally substituted by methyl, ethyl, n-propyl, iso-propyl, butyl, iso-butyl, sec-butyl, tert-butyl, cyclohexyl, trifluoromethyl, methoxy, ethoxy, n-propoxy, iso-propoxy, butoxy, iso-butoxy, sec-butoxy, tert-butoxy, methylthio, ethylthio, fluorine, chlorine or phenyl, or A, B and the carbon atom to which they are bonded very particularly preferably represent $C_5$–$C_6$-cycloalkyl which is substituted by an alkylenediyl group which optionally contains an oxygen or sulphur atom or by an alkylenedioxy group, this alkylenediyl or alkylenedioxy group together with-the carbon atom to which it is bonded forming a further five to six-membered ring, or A, B and the carbon atom to which they are bonded very particularly preferably represent $C_3$–$C_6$-cycloalkyl or $C_5$–$C_6$-cycloalkenyl in which two substituents together with the carbon atoms to which they are bonded represent $C_3$–$C_4$-alkanediyl, $C_3$–$C_4$-alkenediyl or butadienediyl, in each of which one methylene group is optionally replaced by oxygen or sulphur.

D very particularly preferably represents hydrogen, or represents $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl, in which one or two methylene groups which are not directly adjacent are replaced by oxygen and/or sulphur, in each case optionally substituted by fluorine or chlorine, or represents phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together very particularly preferably represent a $C_3$–$C_5$-alkanediyl or $C_3$–$C_5$-alkenediyl group in each of which one methylene group is optionally replaced by oxygen or sulphur and which are optionally substituted by fluorine, chlorine, hydroxyl, mercapto, or by $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or in which in each case one of the following groups

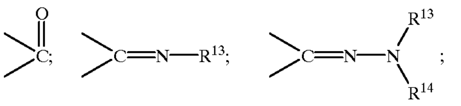

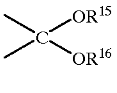

or

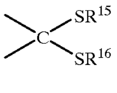

is optionally present, or A and D, in the case of the compounds of the formula (I-1), together with the atoms to which they are bonded represent one of the following groups:

AD-1

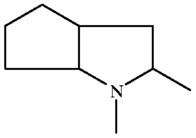

AD-2

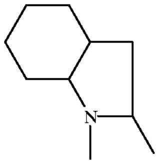

AD-4

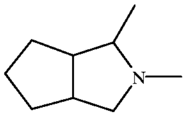

AD-6

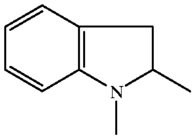

AD-8

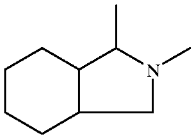

AD-10

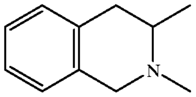

AD-12

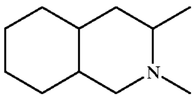

AD-14

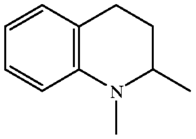

AD-15

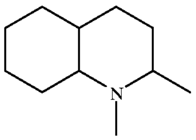

AD-17

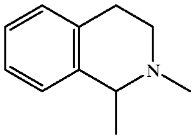

-continued

AD-18

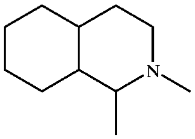

AD-27

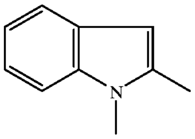

G very particularly preferably, in the event that Het represents one of the radicals (1), (2), (3), (5) or (6), represents hydrogen (a) or, in the event that Het represents one of the radicals (1), (2), (3), (4), (5) or (6), represents one of the groups (b)

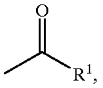

(c)

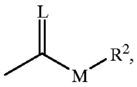

(d)

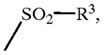

(e)

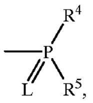

(f)

E or (g)

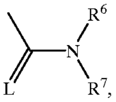

in which

E represents a metal ion equivalent or an ammonium ion,

L represents oxygen or sulphur an

M represents oxygen or sulphur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is optionally substituted by fluorine or chlorine, or represents $C_3$–$C_6$-cycloalkyl which is optionally substituted by fluorine, chlorine, methyl, ethyl, n-propyl, i-propyl, n-butyl, i-butyl, tert-butyl, methoxy, ethoxy, n-propoxy or, iso-propoxy and in which one or two methylene groups which are not directly adjacent are optionally replaced by oxygen and/or sulphur, or represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, or represents benzyl which is optionally substituted by fluorine, chlorine, bromine, methyl, ethyl, n-propyl, i-propyl, methoxy, -ethoxy, trifluoromethyl or trifluoromethoxy, or represents furanyl, thienyl or pyridyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents $C_1$–$C_4$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, or represents $C_3$–$C_6$-cycloalkyl which is optionally substituted by fluorine, chlorine, methyl, ethyl, n-propyl, iso-propyl or methoxy, or represents phenyl or benzyl, each of which is optionally substituted by fluorine, chlorine, cyano, nitro, methyl, ethyl, n-propyl, i-propyl, methoxy, ethoxy, trifluoromethyl or trifluoromethoxy, $R^3$ very particularly preferably represents methyl, ethyl, propyl or isopropyl, each of which is optionally substituted by fluorine or chlorine, or represents phenyl or benzyl, each of which is optionally substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro.

$R^4$ and $R^5$ independently of one another very particularly preferably represent $C_1$–$C_4$-alkyl, $C_1$–$C_4$-alkoxy, $C_1$–$C_4$-alkylamino, di-($C_1$–$C_4$-alkyl)amino or $C_{C4}$-alkylthio, each of which is optionally substituted by fluorine or chlorine, or represent phenyl, phenoxy or phenylthio, each of which is optionally substituted by fluorine, chlorine, bromine, nitro, cyano, methyl, methoxy, trifluoromethyl or trifluoromethoxy.

$R^6$ and $R^7$ independently of one another very particularly preferably represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine or chlorine, or represent phenyl or benzyl, each of which is optionally substituted by fluorine, chlorine, bromine, methyl, methoxy or trifluoromethyl, or together represent a $C_5$–$C_6$-alkylene radical which is optionally substituted by methyl or ethyl and in which one methylene group is optionally replaced by oxygen or sulphur.

$R^{13}$ very particularly preferably represents hydrogen, or represents $C_1$–$C_4$-alkyl or $C_1$–$C_4$-alkoxy, each of which is optionally substituted by fluorine or chlorine, or represents $C_3$–$C_6$-cycloalkyl, or represents phenyl, phenyl-$C_1$–$C_2$-alkyl or benzyloxy, each of which is optionally substituted by fluorine, chlorine, bromine, methyl, ethyl, iso-propyl, tert-butyl, methoxy, ethoxy, isopropoxy, tert-butoxy, trifluoromethyl, trifluoromethoxy, nitro or cyano.

$R^{14}$ very particularly preferably represents hydrogen or $C_1$–$C_4$-alkyl, or $R^{13}$ and $R^{14}$ together very particularly preferably represent $C_4$–$C_6$-alkanediyl.

$R^{15}$ and $R^{16}$ are identical or different and very particularly preferably represent methyl or ethyl, or $R^{15}$ and $R^{16}$ together very particularly preferably represent a $C_2$-$C_3$-alkanediyl radical which is optionally substituted by methyl, ethyl, n-propyl, iso-propyl, n-butyl, iso-butyl, sec-butyl or tert-butyl, or by phenyl which is optionally substituted by fluorine, chlorine, methoxy, trifluoromethyl, trifluoromethoxy, nitro or cyano.

The abovementioned definitions of radicals or illustrations, in general or where preferred ranges have been given, can be combined with each other as desired, that is to say combinations between the respective ranges and preferred ranges are also possible. They apply to the end products and, analogously, to the precursors and intermediates.

Preferred according to the invention are the compounds of the formula (I) in which a combination of the meanings mentioned above as being preferred (preferable) is present.

Particularly preferred according to the invention are the compounds of the formula (I) in which a combination of the meanings mentioned above as being particularly preferred is present.

Very particularly preferred according to the invention are the compounds of the formula (I) in which a combination of the meanings mentioned above as being very particularly preferred is present.

Saturated or unsaturated hydrocarbon radicals, such as alkyl or alkenyl, also in connection with hetero atoms, such as, for example, in alkoxy, can be in each case straight-chain or branched as far as this is possible.

Optionally substituted radicals can be monosubstituted or polysubstituted, it being possible for the substituents in multiple substitutions to be identical or different.

Individual compounds of the formula (I-1-a) which may be mentioned in addition to the compounds mentioned in the preparation examples are those which follow:

TABLE 1

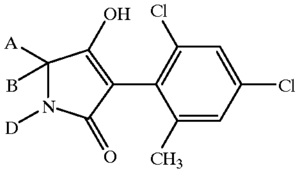

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |

TABLE 1-continued

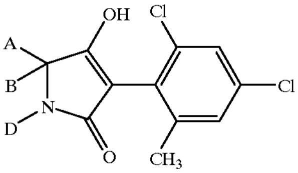

| A | B | D |
|---|---|---|
| $C_4H_9$ | $CH_3$ | H |
| i-$C_4H_9$ | $CH_3$ | H |
| s-$C_4H_9$ | $CH_3$ | H |
| —$C_4H_9$ | $CH_3$ | H |
| $C_2H_5$ | $C_2H_5$ | H |
| $C_3H_7$ | $C_3H_7$ | H |
| 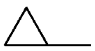 | $CH_3$ | H |
| 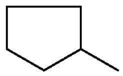 | $CH_3$ | H |
| 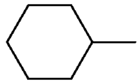 | $CH_3$ | H |
| $—(CH_2)_2—$ | | H |
| $—(CH_2)_4—$ | | H |
| $—(CH_2)_5—$ | | H |
| $—(CH_2)_6—$ | | H |
| $—(CH_2)_7—$ | | H |
| $—(CH_2)_2—O—(CH_2)_2—$ | | H |
| $—(CH_2)_2—S—(CH_2)_2—$ | | H |
| $—CH_2—CHCH_3—(CH_2)_3—$ | | H |
| $—(CH_2)_2—CHCH_3—(CH_2)_2—$ | | H |
| $—(CH_2)_2—CHC_2H_5—(CH_2)_2—$ | | H |
| $—(CH_2)_2—CHC_3H_7—(CH_2)_2—$ | | H |
| $—(CH_2)_2—CHi—C_3H_7—(CH_2)_2—$ | | H |
| $—(CH_2)_2—CHOCH_3—(CH_2)_2—$ | | H |
| $—(CH_2)_2—CHOC_2H_5—(CH_2)_2—$ | | H |
| $—(CH_2)_2—CHOC_3H_7—(CH_2)_2—$ | | H |
| $—(CH_2)_2—CHi—C_3H_7—(CH_2)_2—$ | | H |
| $—(CH_2)_2—C(CH_3)_2—(CH_2)_2—$ | | H |
| $—CH_2—(CHCH_3)_2—(CH_2)_2—$ | | H |
| 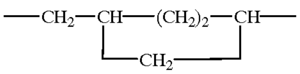 | | H |
| 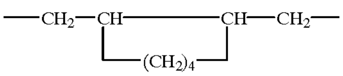 | | H |
| 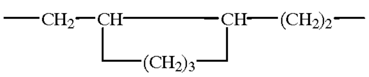 | | H |
| 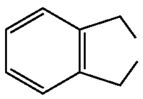 | | H |
| 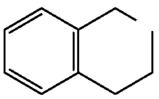 | | H |
| $—(CH_2)_3—$ | | H |

TABLE 1-continued

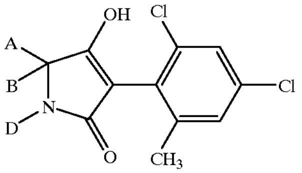

| A | B | D |
|---|---|---|
| $-(CH_2)_4-$ | | H |
| $-CH_2-CHCH_3-CH_2-$ | | H. - |
| $-CH_2-CH_2-CHCH_3-$ | | H |
| $-CH_2-CHCH_3-CHCH_3-$ | | H |
| $-CH_2-S-CH_2-$ | | H |
| $-CH_2-S-(CH_2)_2-$ | | H |
| $-(CH_2)_2-S-CH_2-$ | | H |
| 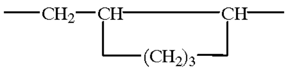 | | H |
| H | $CH_3$ | H |
| H | $C_2H_5$ | H |
| H | $C_3H_7$ | H |
| H | i-$C_3H_7$ | H |
| H | 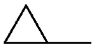 | H |
| H | 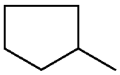 | H |
| H | 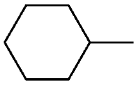 | H |
| $CH_3$ | $CH_3$ | H |
| $CH_3$ | $C_2H_5$ | H |
| $CH_3$ | $C_3H_7$ | H |
| $CH_3$ | i-$C_3H_7$ | H |
| $CH_3$ | 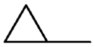 | H |
| $CH_3$ | 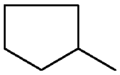 | H |
| $CH_3$ | 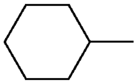 | H |
| $C_2H_5$ | $CH_3$ | H |
| $C_2H_5$ | $C_2H_5$ | H |

TABLE 2

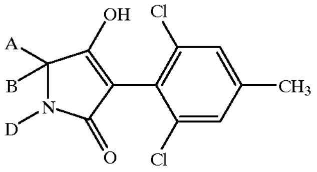

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| 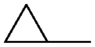 | $CH_3$ | H |
| 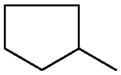 | $CH_3$ | H |
| 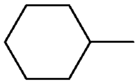 | $CH_3$ | H |
| $-(CH_2)_2-$ | | H |
| $-(CH_2)_4-$ | | H |
| $-(CH_2)_5-$ | | H |
| $-(CH_2)_6-$ | | H |
| $-(CH_2)_7-$ | | H |
| $-(CH_2)_2-O-(CH_2)_2-$ | | H |
| $-(CH_2)_2-S-(CH_2)_2-$ | | H |
| $-CH_2-CHCH_3-(CH_2)_3-$ | | H |
| $-(CH_2)_2-CHCH_3-(CH_2)_2-$ | | H |
| $-(CH_2)_2-CHC_2H_5-(CH_2)_2-$ | | H |
| $-(CH_2)_2-CHC_3H_7-(CH_2)_2-$ | | H |
| $-(CH_2)_2-CHi-C_3H_7-(CH_2)_2-$ | | H |
| $-(CH_2)_2-CHOCH_3-(CH_2)_2-$ | | H |
| $-(CH_2)_2-CHOC_2H_5-(CH_2)_2-$ | | H |
| $-(CH_2)_2-CHOC_3H_7-(CH_2)_2-$ | | H |
| $-(CH_2)_2-CHi-C_3H_7-(CH_2)_2-$ | | H |
| $-(CH_2)_2-C(CH_3)_2-(CH_2)_2-$ | | H |
| $-CH_2-(CHCH_3)_2-(CH_2)_2-$ | | H |
| 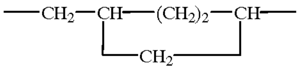 | | H |
| 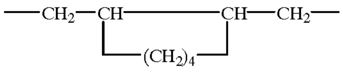 | | H |
| 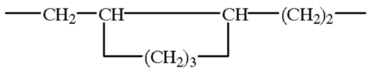 | | H |

TABLE 2-continued

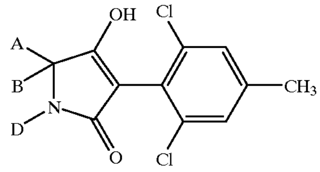

| A | B | D |
|---|---|---|
| 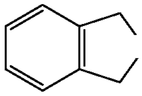 | | H |
| 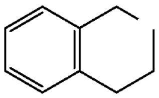 | | H |
| $—(CH_2)_3—$ | | H |
| $—(CH_2)_4—$ | | H |
| $—CH_2—CHCH_3—CH_2—$ | | H |
| $—CH_2—CH_2—CHCH_3—$ | | H |
| $—CH_2—CHCH_3—CHCH_3—$ | | H |
| $—CH_2—S—CH_2—$ | | H |
| $—CH_2—S—(CH_2)_2—$ | | H |
| $—(CH_2)_2—S—CH_2—$ | | H |
| 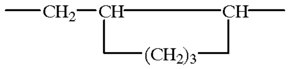 | | H |
| H | $CH_3$ | H |
| H | $C_2H_5$ | H |
| H | $C_3H_7$ | H |
| H | $i-C_3H_7$ | H |
| H | 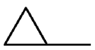 | H |
| H | 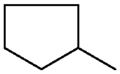 | H |
| H | 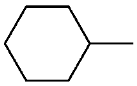 | H |
| $CH_3$ | $CH_3$ | H |
| $CH_3$ | $C_2H_5$ | H |
| $CH_3$ | $C_3H_7$ | H |
| $CH_3$ | $i-C_3H_7$ | H |
| $CH_3$ | 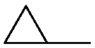 | H |
| $CH_3$ | 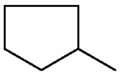 | H |
| $CH_3$ | 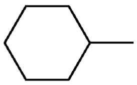 | H |
| $C_2H_5$ | $CH_3$ | H |
| $C_2H_5$ | $C_2H_5$ | H |

Individual compounds of the formula (I-2-a) which may be mentioned in addition to the compounds mentioned in the preparation examples are those which follow:

TABLE 3

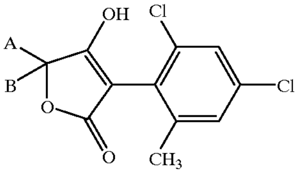

| A | B |
|---|---|
| $CH_3$ | H |
| $C_2H_5$ | H |
| $C_3H_7$ | H |
| $i-C_3H_7$ | H |
| $C_4H_9$ | H |
| $i-C_4H_9$ | H |
| $s-C_4H_9$ | H |
| $t-C_4H_9$ | H |
| $CH_3$ | $CH_3$ |
| $C_2H_5$ | $CH_3$ |
| $C_3H_7$ | $CH_3$ |
| $i-C_3H_7$ | $CH_3$ |
| $C_4H_9$ | $CH_3$ |
| $i-C_4H_9$ | $CH_3$ |
| $s-C_4H_9$ | $CH_3$ |
| $—C_4H_9$ | $CH_3$ |
| $C_2H_5$ | $C_2H_5$ |
| $C_3H_7$ | $C_3H_7$ |
| 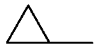 | $CH_3$ |
| 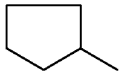 | $CH_3$ |
| 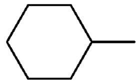 | $CH_3$ |
| $—(CH_2)_2—$ | |
| $—(CH_2)_4—$ | |
| $—(CH_2)_5—$ | |
| $—(CH_2)_6—$ | |
| $—(CH_2)_7—$ | |
| $—(CH_2)_2—O—(CH_2)_2—$ | |
| $—(CH_2)_2—S—(CH_2)_2—$ | |
| $—CH_2—CHCH_3—(CH_2)_3—$ | |
| $—(CH_2)_2—CHCH_3—(CH_2)_2—$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi—C_3H_7—(CH_2)_2—$ | |
| $—(CH_2)_2—CHOCH_3—(CH_2)_2—$ | |
| $—(CH_2)_2—CHOC_2H_5—(CH_2)_2—$ | |
| $—(CH_2)_2—CHOC_3H_7—(CH_2)_2—$ | |
| $—(CH_2)_2—CHi—C_3H_7—(CH_2)_2—$ | |
| $—(CH_2)_2—C(CH_3)_2—(CH_2)_2—$ | |
| $—CH_2—(CHCH_3)_2—(CH_2)_2—$ | |
| 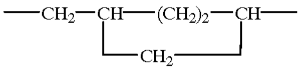 | |
| 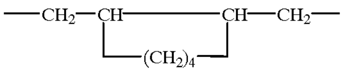 | |

TABLE 3-continued

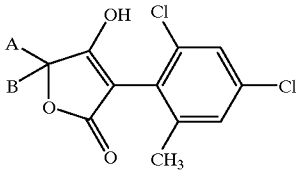

| A | B |
| --- | --- |
| 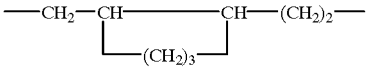 | |
| 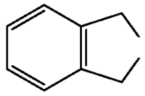 | |
| 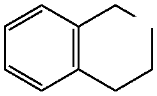 | |

TABLE 4

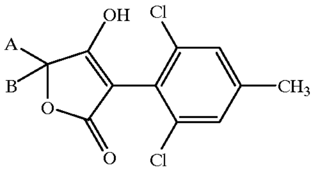

| A | B |
| --- | --- |
| $CH_3$ | H |
| $C_2H_5$ | H |
| $C_3H_7$ | H |
| i-$C_3H_7$ | H |
| $C_4H_9$ | H |
| i-$C_4H_9$ | H |
| s-$C_4H_9$ | H |
| t-$C_4H_9$ | H |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| $—C_4H_9$ | $CH_3$ |
| $C_2H_5$ | $C_2H_5$ |
| $C_3H_7$ | $C_3H_7$ |
| 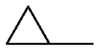 | $CH_3$ |
| 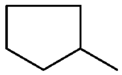 | $CH_3$ |
| 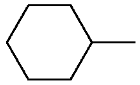 | $CH_3$ |
| $—(CH_2)_2—$ | |
| $—(CH_2)_4—$ | |

TABLE 4-continued

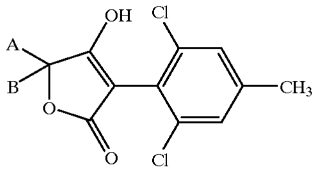

| A | B |
| --- | --- |
| $—(CH_2)_5—$ | |
| $—(CH_2)_6—$ | |
| $—(CH_2)_7—$ | |
| $—(CH_2)_2—O—(CH_2)_2—$ | |
| $—(CH_2)_2—S—(CH_2)_2—$ | |
| $—CH_2—CHCH_3—(CH_2)_3—$ | |
| $—(CH_2)_2—CHCH_3—(CH_2)_2—$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi—C_3H_7—(CH_2)_2—$ | |
| $—(CH_2)_2—CHOCH_3—(CH_2)_2—$ | |
| $—(CH_2)_2—CHOC_2H_5—(CH_2)_2—$ | |
| $—(CH_2)_2—CHOC_3H_7—(CH_2)_2—$ | |
| $—(CH_2)_2—CHi—C_3H_7—(CH_2)_2—$ | |
| $—(CH_2)_2—C(CH_3)_2—(CH_2)_2—$ | |
| $—CH_2—(CHCH_3)_2—(CH_2)_2—$ | |
| 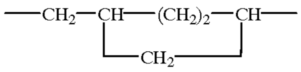 | |
| 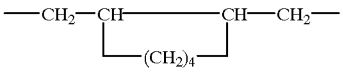 | |
| 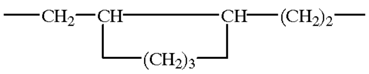 | |
| 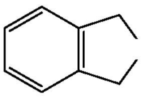 | |
| 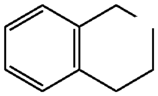 | |

Individual compounds of the formula (1-3-a) which may be mentioned in addition to the compounds mentioned in the preparation examples are those which follow:

TABLE 5

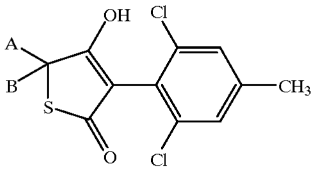

| A | B |
| --- | --- |
| $CH_3$ | H |
| $C_2H_5$ | H |
| $C_3H_7$ | H |
| i-$C_3H_7$ | H |
| $C_4H_9$ | H |
| i-$C_4H_9$ | H |

TABLE 5-continued

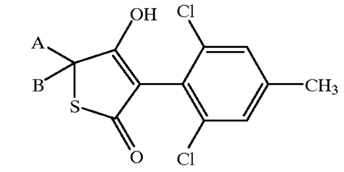

| A | B |
|---|---|
| s-$C_4H_9$ | H |
| t-$C_4H_9$ | H |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
| 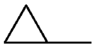 | $CH_3$ |
| 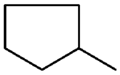 | $CH_3$ |
| 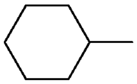 | $CH_3$ |
| $—(CH_2)_2—$ | |
| $—(CH_2)_4—$ | |
| $—(CH_2)_5—$ | |
| $—(CH_2)_6—$ | |
| $—(CH_2)_7—$ | |
| $—(CH_2)_2—O—(CH_2)_2—$ | |
| $—(CH_2)_2—S—(CH_2)_2—$ | |
| $—CH_2—CHCH_3—(CH_2)_3—$ | |
| $—(CH_2)_2—CHCH_3—(CH_2)_2—$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi—C_3H_7—(CH_2)_2—$ | |
| $—(CH_2)_2—CHOCH_3—(CH_2)_2—$ | |
| $—(CH_2)_2—CHOC_2H_5—(CH_2)_2—$ | |
| $(CH_2)_2—CHOC_3H_7—(CH_2)_2—$ | |
| $—(CH_2)_2—CHi—C_3H_7—(CH_2)_2—$ | |
| $—(CH_2)_2—C(CH_3)_2—(CH_2)_2—$ | |
| $—CH_2—(CHCH_3)_2—(CH_2)_2—$ | |
| 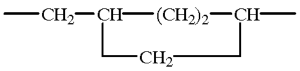 | |
| 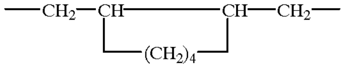 | |
| 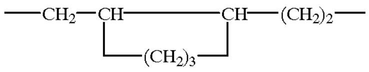 | |
| 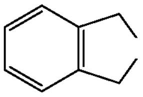 | |

TABLE 5-continued

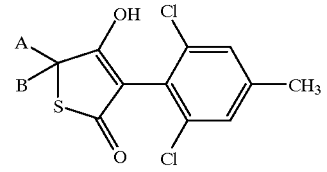

| A | B |
|---|---|
| 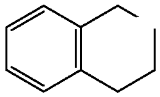 | |

Individual compounds of the formula (I-5-a) which may be mentioned in addition to the compounds mentioned in the preparation examples are those which follow:

TABLE 6

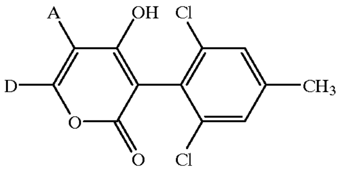

| A | D |
|---|---|
| H | $CH_3$ |
| H | $C(CH_3)_3$ |
| H | $C(CH_3)_2CH_2Cl$ |
| $CH_3$ | $CH_3$ |
| $CH_3$ | $CH_2CHCH_3CH_2CH_3$ |
| H | $CH{=}C(CH_3)_2$ |
| $CH_3$ | 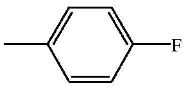 |
| $CH_3$ | 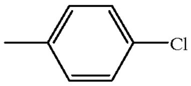 |
| $CH_3$ | 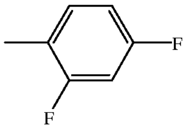 |
| $CH_3$ | 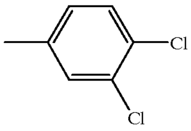 |
| $CH_3$ | 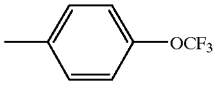 |
| 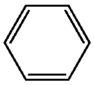 | $CH_3$ |

TABLE 6-continued
| | |
|---|---|
| H | 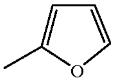 |
| $CH_3$ | 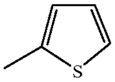 |
| $CH_3$ | 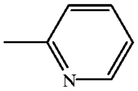 |
| $CH_3$ | 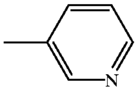 |
| $CH_3$ | 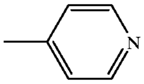 |
| H | 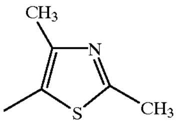 |
| $CH_3$ | $C_5H_9$ |
| $CH_3$ | $C_3H_5$ |
| H | $C_3H_4Cl$ |
| | $(CH_2)_3$ |
| | $(CH_2)_4$ |
| | $C(CH_3)_2OC(CH_3)_2$ |
| H | $CH_3$ |
| H | $C(CH_3)_3$ |
| H | $C(CH_3)_2CH_2Cl$ |
| $CH_3$ | $CH_3$ |
| $CH_3$ | $CH_2CHCH_3CH_2CH_3$ |
| H | $CH{=}C(CH_3)_2$ |
| $CH_3$ | 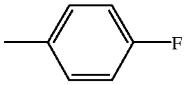 |
| $CH_3$ | 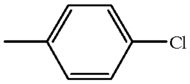 |
| $CH_3$ | 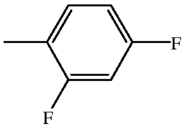 |
| $CH_3$ | 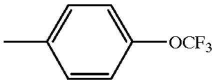 |
| 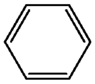 | $CH_3$ |
TABLE 6-continued
| | |
|---|---|
| H | 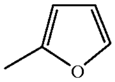 |
| $CH_3$ | 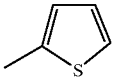 |
| $CH_3$ | 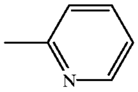 |
| $CH_3$ | 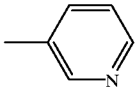 |
| $CH_3$ | 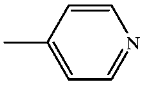 |
| $CH_3$ | $C_5H_9$ |
| $CH_3$ | $C_3H_5$ |
| H | $C_3H_4Cl$ |
| | $(CH_2)_3$ |
| | $(CH_2)_4$ |
| | $C(CH_3)_2OC(CH_3)_2$ |
| A |
|---|
| $CH_3$ |
| $CH(CH_3)_2$ |
| 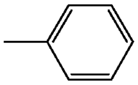 |
| 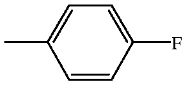 |
| 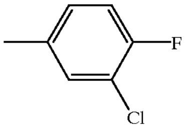 |
| 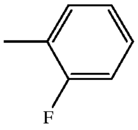 |
| $CH_3$ |
| $CH(CH_3)_2$ |
| 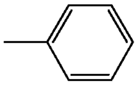 |
| 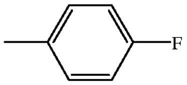 |

TABLE 6-continued

| |
|---|
| 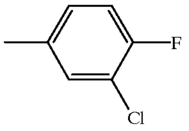 |
| 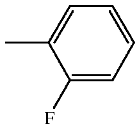 |

If, in accordance with process (B), ethyl O-[(2,6-dichloro-4-methyl)-phenylacetyl]-hydroxyacetate is used, the course of the process according to the invention can be represented by the following equation:

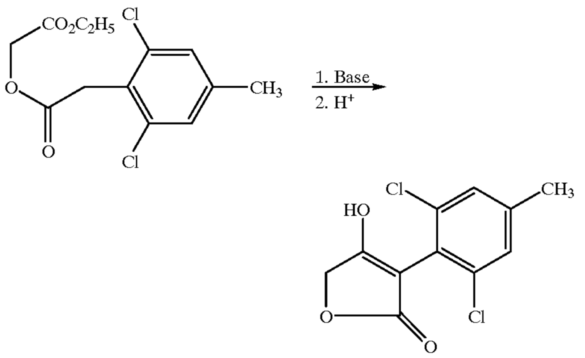

If, in accordance with process (C), ethyl 2-[(2-chloro-6-fluoro-4-methyl)-phenyl]-4-(4-methoxy)-benzylmercapto-4-methyl-3-oxo-valerate is used, the course of the process according to the invention can be represented by the following equation:

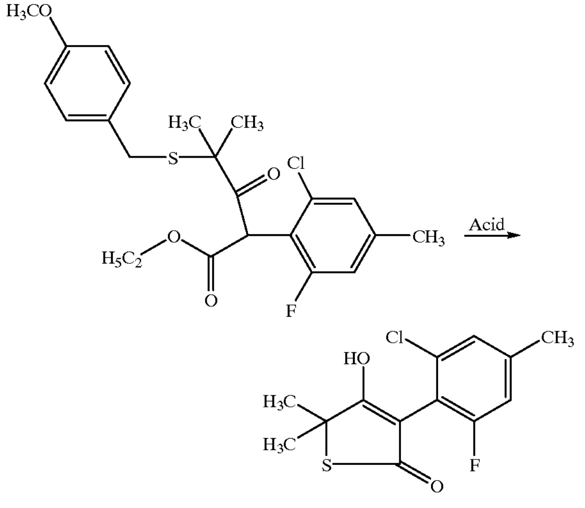

If, for example, in accordance with process (E), chlorocarbonyl 2-[(2,4-dichloro-6-methyl)-phenyl] ketene and acetone are used as starting compounds, the course of the methyl)-phenyl] ketene and thiobenzamide are used as starting compounds, the course of the process according to the invention can be represented by the following equation:

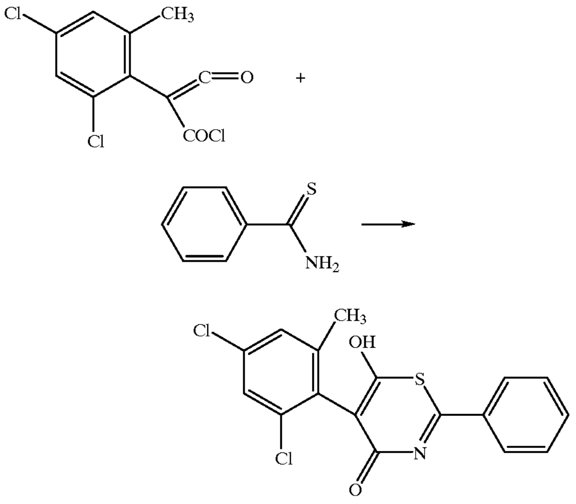

If, in accordance with process (Gα), 3-[(2,6-dichloro-4-methyl)-phenyl]-5,5-dimethyl-pyrrolidine-2,4-dione and pivaloyl chloride are used as starting substances, the course of the process according to the invention can be represented by the following equation:

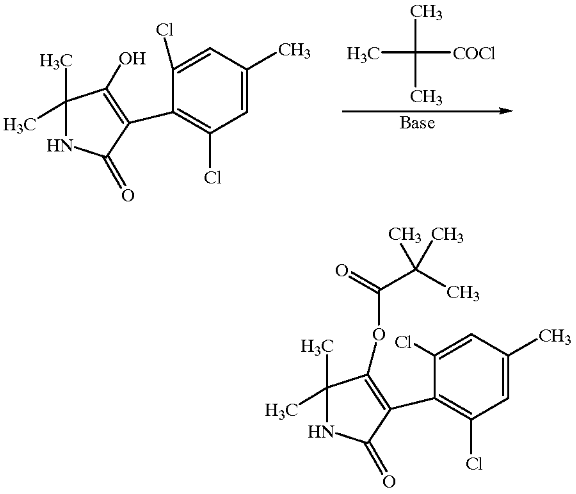

If, in accordance with process (G) (variant β), 3-[(2,4-dichloro-6-methyl)-phenyl]-4-hydroxy-5-phenyl-$\Delta^3$-dihydrofuran-2-one and acetic anhydride are used as starting compounds, the course of the process according to the invention can be represented by If, in accordance with process (H), 8-[(2,4-dichloro-6-methyl)-phenyl]-1,6-diazabicyclo-(4,3,$0^{1,6}$)-nonane-7,9-dione and ethoxyethyl chloroformate are used as starting compounds, the course of the process according to the invention can be represented by the following equation:

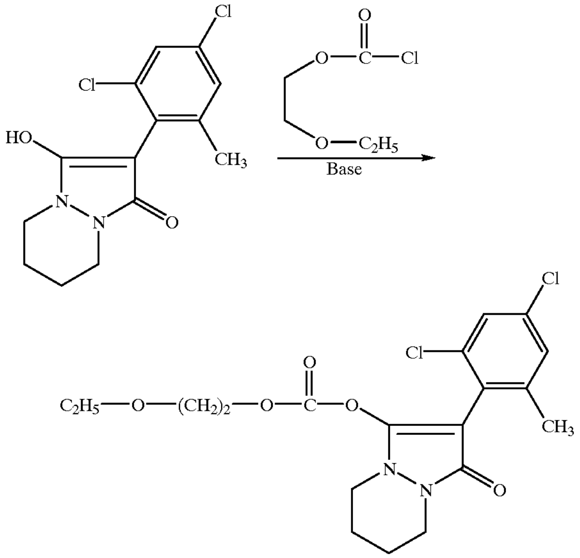

If, in accordance with process (I), variant α, 3-[(2,6-dichloro-4-methyl)-phenyl]-4-hydroxy-6-(3-pyridyl)-pyrone and methyl chloromonothioformate are used as starting materials, the course of the reaction can be represented as follows:

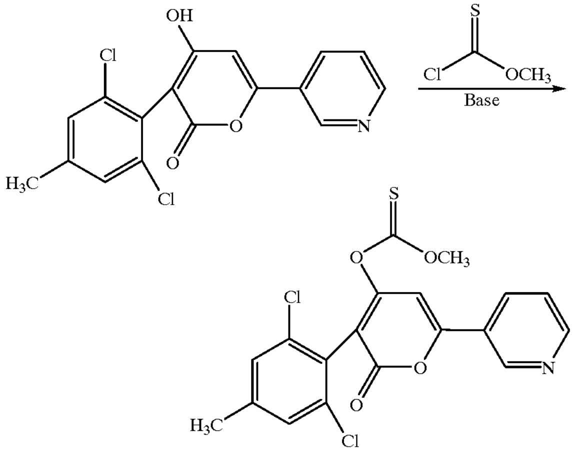

If, in accordance with process (K), variant β, 5-[(2-chloro-6-fluoro-4-methyl)-phenyl]-6-hydroxy-2-(4-chlorophenyl)-thiazin-4-one, carbon disulphide and methyl iodide are used If, in accordance with process (J), 2-[(2,4-dichloro-6-methyl)-phenyl]-1,5-dimethylene-pyrrolidine-2,4-dione and methanesulphonyl chloride are used as starting materials, the course of the reaction can be represented by the following equation:

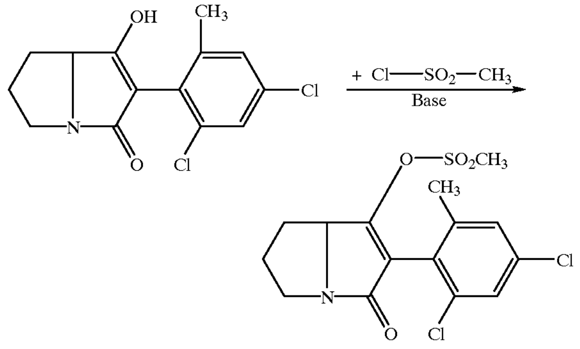

If, in accordance with process (K), 2-[(2,6-dichloro-4-methyl)-phenyl]-4-hydroxy-5-methyl-6-(2-pyridyl)-pyrone and 2,2,2-trifluoroethyl methanethiochlorophosphonate are used as starting materials, the course of the reaction can be represented by the following equation:

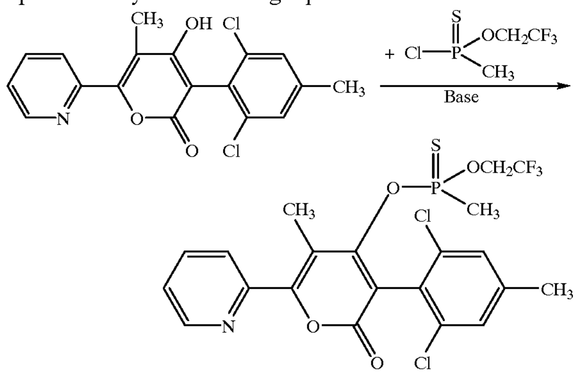

If, in accordance with process (L), 3-[(2,4-dichloro-6-methyl)-phenyl]-5-cyclopropyl-5-methyl-pyrrolidine-2,4-dione and NaOH are used as components, the course of the process according to the invention can be represented by the following equation:

If, in accordance with process (M), variant α, 3-[(2,6-dichloro-4-methyl)-phenyl]-4-hydroxy-5,5-tetramethylene-$\Delta^3$-dihydro-furan-2-one and ethyl isocyanate are used as starting materials, the course of the reaction can be represented by the following equation:

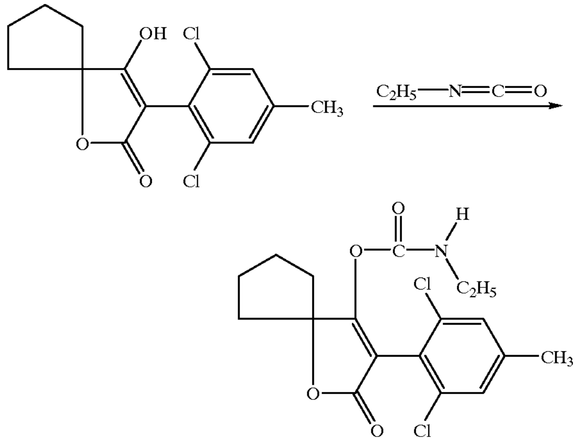

If, in accordance with process (M), variant β, 3-[(2,6-dichloro-4-methyl)-phenyl]-5-methyl-pyrrolidine-2,4-dione and dimethylcarbamoyl chloride are used as starting materials, the course of the reaction can be represented by the following equation:

The compounds of the formula (II)

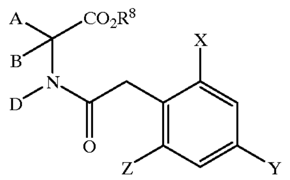

(II)

in which

A, B, D, X, Y, Z and $R^8$ have the abovementioned meanings, and which are required as starting substances in process (A) according to the invention are new.

The acylamino acid esters of the formula (II) are obtained, for example, when amino acid derivatives of the formula (XXI)

(XXI)

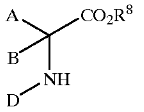

in which in which

X, Y and Z have the abovementioned meanings and

Hal represents chlorine or bromine (Chem. Reviews 52, 237–416 (1953); Bhattacharya, Indian J. Chem. 6, 341–5, 1968) or when acylamino acids of the formula (XXIII)

(XXIII)

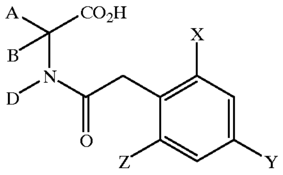

in which

A, B, D, X, Y and Z have the abovementioned meanings, are esterified (Chem. Ind. (London) 1568 (1968)).

The compounds of the formula (XXIII) are new.

The compounds of the formula (XXIII) are obtained when amino acids of the formula (XXIV)

(XXIV)

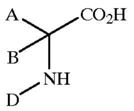

in which

A, B and D have the abovementioned meanings, are acylated with substituted phenylacetyl halides of the formula (XXII)

(XXII)

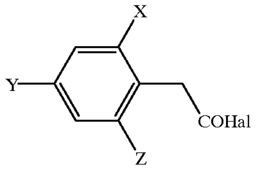

in which

X, Y and Z have the abovementioned meanings and

Hal represents chlorine and bromine, (XXV)

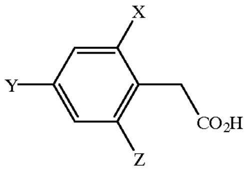

in which

X, Y and Z have the abovementioned meanings, with halogenating agents (for example thionyl chloride, thionyl bromide, oxalyl chloride, phosgene, phosphorus trichloride, phosphorus tribromide or phosphorus pentachloride) at temperatures from −20° C. to 150° C., preferably from −10° C. to 100° C., if appropriate in the presence of a diluent (for example optionally chlorinated aliphatic or aromatic hydrocarbons, such as toluene or methylene chloride).

The compounds of the formula (XXV) are new with the exception of 2,4-dichloro-6-methyl-phenylacetic acid (see Crosby et al., J. Agric. Food Chem. 33, 569–73 (1985).

The compounds of the formula (XXV) are obtained, for example, by hydrolysing substituted phenylacetic esters of the formula (XXVI)

(XXVI)

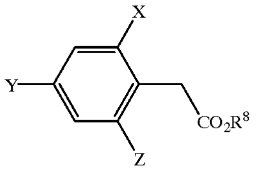

aqueous alcohol, such as methanol or ethanol).

The compounds of the formula (XXVI) are new.

The compounds of the formula (XXVI) are obtained, for example, by reacting substituted 1,1,1-trichloro-2-phenylethanes of the formula (XXVII)

(XXVII)

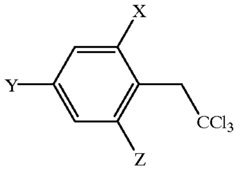

in which

X, Y and Z have the abovementioned meanings, first with alcoholates (for example alkali metal alcoholates, such as sodium methylate or sodium ethylate) at temperatures between 0° C. and 150° C., preferably between 20° C. and 120° C., in the presence of a diluent (for example the alcohol derived from the alcoholate), and subsequently with an acid (preferably an inorganic acid such as, for example, sulphuric acid) at temperatures between −20° C. and 150° C., preferably 0° C. and 100° C.

The compounds of the formula (XXVII) are new.

in which

X, Y and Z have the abovementioned meanings, are reacted with vinylidene chloride ($CH_2{=}CCl_2$) at a temperature from −20° C. to 80° C., preferably 0° C. to 60°

C., in the presence of an alkyl nitrite of the formula (XXIX)

$R^{21}$—ONO (XXIX)

in which $R^{21}$ represents alkyl, preferably $C_1$–$C_6$-alkyl, in the presence of copper(II) chloride and, if appropriate, in the presence of a diluent (for example an aliphatic nitrite, such as acetonitrile).

The compounds of the formulae (XXVIII) and (XXIX) are known compounds of organic chemistry. Copper(II) chloride and vinylidene chloride have been known for a long time and are commercially available.

Some of the compounds of the formulae (XXI) and (XXIV) are known and/or can be synthesized from known processes (see, for example, Compagnon, Miocque Ann. Chim. (Paris) [14] 5, p. 11–22, 23–27 (1970)). position.

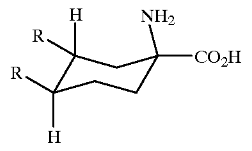
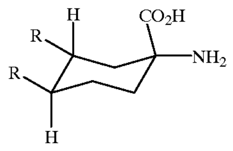

(L. Munday, J. Chem. Soc. 4372 (1961); J. T. Eward, C. Jitrangeri, Can. J. Chem. 53, 3339 (1975).

Furthermore, the starting substances of the formula (II)

(II)

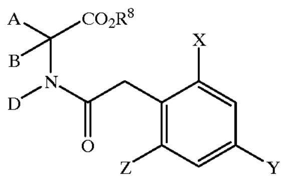

in which

A, B, D, X, Y, Z and $R^8$ have the abovementioned meanings, and which are used in the above process (A) can be prepared when aminonitriles of the A, B and D have the abovementioned meanings, are reacted with substituted phenylacetyl halides of the formula (XXII)

(XXII)

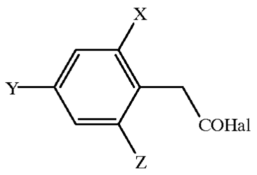

in which

X, Y, Z and Hal have the abovementioned meanings, to give compounds of the formula (XXXI)

(XXXI)

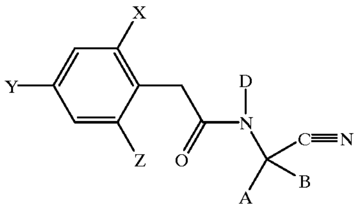

in which

A, B, D, X, Y and Z have the abovementioned meanings, (III)

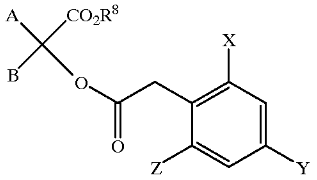

in which

A, B, X, Y, Z and $R^8$ have the abovementioned meanings, and which are required as starting substances in process (B) according to the invention are new.

They can be prepared in a simple manner by methods known in principle.

The compounds of the formula (III) are obtained, for example, when 2-hydroxycarboxylic esters of the formula (XXII)

(XXXII)

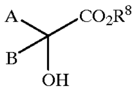

in which

A, B and $R^8$have the abovementioned meanings, are acylated with substituted phenylacetyl halides of the formula (XXII)

X, Y, Z and Hal have the abovementioned meanings, (Chem. Reviews 52, 237–416 (1953)).

Furthermore, compounds of the formula (III) are obtained when substituted phenylacetic acids of the formula (XXV)

(XXV)

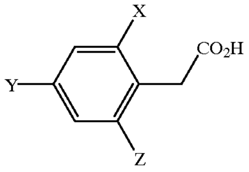

in which

X, Y and Z have the abovementioned meanings, are reacted with α-halogenocarboxylic esters of the formula (XXXIII)

(XXXIII)

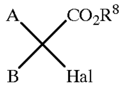

in which

A, B and $R^8$ have the abovementioned meanings and (IV)

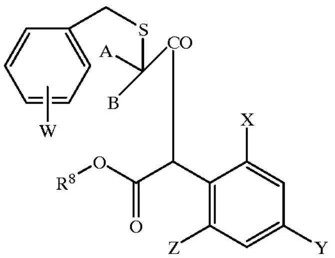

in which

A, B, W, X, Y, Z and $R^8$ have the abovementioned meanings and which are required as starting substances in the above process (C) are new.

They can be prepared by methods known in principle.

The compounds of the formula (IV) are obtained, for example, when substituted phenylacetic esters of the formula (XXVI)

(XXVI)

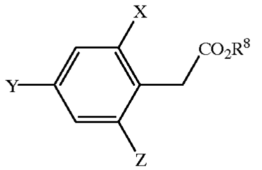

in which in which

A, B and W have the abovementioned meanings and

Hal represents halogen (in particular chlorine or bromine), in the presence of strong bases (see, for example, M. S. Chambers, E. J. Thomas, D. J. Williams, J. Chem. Soc. Chem. Commun., (1987), 1228).

Some of the benzylthio-carbonyl halides of the formula (XXXIV) are known and/or can be prepared by known processes (J. Antibiotics (1983), 26, 1589).

The halogenocarbonyl ketenes of the formula (V) which are required as starting substances in process (E) are new. They can be prepared in a simple manner by methods known in principle (cf., for example, Org. Prep. Proced. Int., 7, (4), 155–158, 1975 and DE 1 945 703). The compounds of the formula (V)

(V)

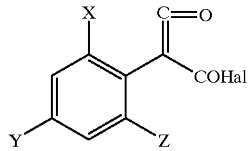

in which (XXXV)

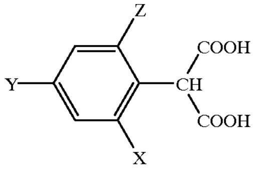

in which

X, Y and Z have the abovementioned meanings are reacted with acid halides, such as, for example, thionyl chloride, phosphorus(V) chloride, phosphorus(III) chloride, oxalyl chloride, phosgene or thionyl bromide, at a temperature between −20° C. and 200° C., preferably between 0° C. and 150° C., if appropriate in the presence of catalysts, such as, for example, diethylformamide, methyl-stearylformamide or triphenylphosphine, and, if appropriate, in the presence of bases, such as, for example, pyridine or triethylamine.

The substituted phenylmalonic acids of the formula (XXXV) are new. However, they can be prepared in a simple manner by known processes (cf., for example, Organikum [Laboratory Practical in Organic Chemistry], VEB Deutscher Verlag der Wissenschaften, Berlin 1977, p. 517 et seq.).

The carbonyl compounds of the formula (VIII) or their silyl enol ethers of the formula (VIIIa)

and which are required as starting substances for the process (E) according to the invention are commercially available, generally known or accessible by known processes.

The preparation of the ketene acid chlorides of the formula (V) which are required as starting substances for carrying out process (F) according to the invention were already described in process (E) according to the invention. The thioamides of the formula (IX)

(IX)

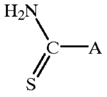

in which

A has the abovementioned meaning and which are required for carrying out process (F) according to the invention are compounds generally known in organic chemistry.

The compounds of the formula (I-4-a) which are required as starting substances in process (G) are known and/or can be prepared in a simple manner by known methods (cf. also WO 92/16510).

The compounds of the formula (I-4-a) are obtained, for example, when compounds of the formula (V)

(V)

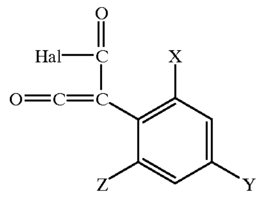

in which

X, Y and Z have the abovementioned meanings and

Hal represents halogen (in particular chlorine or bromine)

or compounds of the formula (VI)

(VI)

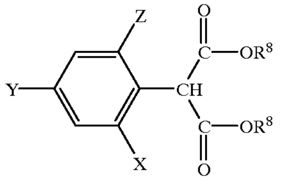

in which $R^8$, X, Y and Z have the abovementioned meanings are reacted with hydrazines of the formula (VII)

A—NH—NH—D (VII)

in which

A and D have the abovementioned meanings, at temperatures between −20° C. and 250° C., preferably between 0° C. and 150° C., if appropriate in the presence of a diluent, the following being suitable: hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and, only in the event that compounds of the formula (VI) are employed, alcohols, such as methanol, ethanol, propanol, iso-propanol, butanol, iso-butanol and tert-butanol, and, if appropriate, in the presence of a base, suitable bases being, in the event that compounds of the formula (V) are employed, inorganic bases, in particular alkali metal carbonates or alkaline earth metal carbonates, such as sodium carbonate, potassium carbonate or calcium carbonate, and organic bases, such as, for example, pyridine or triethylamine, and, in the event that compounds of the formula (V) are employed, alkali metal oxides, alkali metal hydroxides and alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine), alkali metals, such as sodium or potassium, alkali metal amides, alkali metal hydrides, alkaline earth metal amides and alkaline earth metal hydrides, such as sodium amide, sodium hydride and calcium hydride, and, moreover, also alkali metal alcoholates, such as sodium methylate, sodium ethylate and potassium tert-butylate.

The malonic esters of the formula (VI)

(VI)

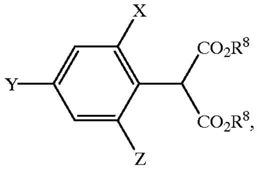

in which $R^8$, X, Y and Z have the abovementioned meanings, are new. They can be synthesized by generally known methods of organic chemistry (cf., for example, Tetrahedron Lett. 27, 2763 (1986) and Organikum [Laboratory Practical in Organic Chemistry] VEB Deutscher Verlag der Wissenschaften, Berlin 1977, p. 587 et seq.).

The hydrazines of the formula (VII)

A—NH—NH—D (VII), in which

A and D have the abovementioned meanings, are known in some cases and/or can be prepared by methods known from the literature (cf, for example, Liebigs Ann. Chem. 585, 6 (1954); Reaktionen der organischen Synthese [Reactions in Organic Synthesis], C. Ferri, pages 212, 513; Georg Thieme Verlag Stuttgart, 1978; Liebigs Ann. Chem. 443, 242 (1925); Chem. Ber. 98, 2551 (1965), EP 508 126).

The acid halides of the formula (X), carboxylic anhydrides of the formula (XI), chloroformic esters or chloroformic thioesters of the formula (XII), chloromonothioformic esters or chlorodithioformic esters of the formula (XIII), alkyl halides of the formula (XIV), sulphonyl chlorides of the formula (XV), phosphorus compounds of the formula (XVI), metal hydroxides, metal alkoxides or amines of the formulae (XVII) and (XVIII), isocyanates of the formula (XIX) and carbamoyl chlorides of the formula (XX), all of which are furthermore required as starting substances for carrying out processes (G), (H), (I), (J), (K), (L) and (M) according to the invention are generally known compounds of organic or inorganic chemistry.

Moreover, the compounds of the formulae (VII), (VIII), (IX). to (XXI), (XXIV) and (XXXII) to (XXXIV) are disclosed in the patent applications cited at the outset and/or can be prepared by the methods described in these publications.

Process (A) is characterized in that compounds of the formula (II) in which A, B, D, X, Y, Z and $R^8$ have the abovementioned meanings are subjected to intramolecular condensation in the presence of a diluent and in the presence of a base.

Diluents which can be employed in process (A) according to the invention are all organic solvents which are inert to the reactants. The following can preferably be used: hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Bases (deprotonating agents) which can be employed for carrying out process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, all of which can be employed in the presence of phase transfer catalysts, such as, for example, triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine. Alkali metals, such as sodium or potassium, can furthermore be used. It is also possible to employ alkali metal amides, alkali metal hydrides, alkaline earth metal amides and alkaline earth metal hydrides, such as sodium amide, sodium hydride and calcium hydride, and furthermore also alkali metal alcoholates, such as sodium methylate, sodium ethylate and potassium tert-butylate.

When carrying out process (A) according to the invention, the reaction temperature can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactant of the formula (II) and the deprotonating base are generally employed in an equimolar to approximately twice the equimolar amounts. However, it is also possible to use one or the other reactant in a larger excess (up to 3 mol).

Process (B) is characterized in that compounds of the formula (III) in which A, B, X, Y, Z and $R^8$ have the abovementioned meanings are subjected to intramolecular condensation in the presence of a diluent and in the presence of a base.

Diluents which can be employed in process (B) according to the invention are all organic solvents which are inert to the reactants. The following can preferably be used: hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. Alcohols, such as methanol, ethanol, propanol, iso-propanol, butanol, iso-butanol and tert-butanol, can furthermore be employed.

Bases (deprotonating agents) which can be employed for carrying out process (B) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, all of which can be employed in the presence of phase transfer catalysts, such as, for example, triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine. Alkali metals, such as sodium or potassium, can furthermore be used. It is also possible to employ alkali metal amides, alkali metal hydrides, alkaline earth metal amides and alkaline earth metal hydrides, such as sodium amide, sodium hydride and calcium hydride, and furthermore also alkali metal alcoholates, such as sodium methylate, sodium ethylate and potassium tert-butylate.

When carrying out process (B) according to the invention, the reaction temperature can be varied within a substantial range. In general, the process is carried out at temperatures between 0° C. and 250° C., preferably between 50° C. and 150° C.

Process (B) according to the invention is generally carried out under atmospheric pressure.

When carrying out process (B) according to the invention, the reactants of the formula (III) and the deprotonating base are generally employed in approximately equimolar amounts. However, it is also possible to use one or the other reactant in a larger excess (up to 3 mol).

Process (C) is characterized in that compounds of the formula (IV) in which A, B, W, X, Y, Z and $R^8$ have the abovementioned meanings are subjected to intramolecular cyclization in the presence of an acid, and, if appropriate, in the presence of a diluent.

Diluents which can be employed in process (C) according to the invention are all organic solvents which are inert to the reactants. The following can preferably be used: hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methyl-pyrrolidone. Alcohols, such as methanol, ethanol, propanol, iso-propanol, butanol, iso-butanol and tert-butanol, can furthermore be employed.

If appropriate, the acid employed can also act as the diluent.

Acids which can be employed in process (C) according to the invention are all customary inorganic and organic acids, such as, for example, hydrohalic acids, sulphuric acid, alkyl-, aryl- and haloalkylsulphonic acids; acids which are used in particular are halogenated alkylcarboxylic acids, such as, for example, trifluoroacetic acid.

When carrying out process (C) according to the invention, the reaction temperature can be varied within a substantial range. In general, the process is carried out at temperatures between 0° C. and 250° C., preferably between 50° C. and 150° C.

Process (C) according to the invention is generally carried out under atmospheric pressure.

When carrying out process (C) according to the invention, the reactants of the formula (IV) and the acid are employed, for example, in equimolar amounts. If appropriate, however, it is also possible to employ the acid in catalytic amounts.

Process (E) according to the invention is characterized in that carbonyl compounds of the formula (VIII) or their silyl enol ethers of the formula (VIIIa) are reacted with ketene acid halides of the formula (V), if appropriate in the presence of a diluent and if appropriate in the presence of an acid acceptor.

Diluents which can be employed in process (E) according to the invention are all organic solvents which are inert to the reactants. The following can preferably be used: hydrocarbons, such as o-dichlorobenzene, tetralin, toluene and xylene, furthermore ethers, such as dibutyl ether, glycol dimethyl ether and diglycol dimethyl ether, moreover polar solvents, such as dimethyl sulphoxide, sulpholane, dimethylformamide or N-methyl-pyrrolidone.

Acid acceptors which can be used when carrying out process (E) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base or N,N-dimethyl-aniline.

When carrying out process (E) according to the invention, the reaction temperature can be varied within a substantial range. Expediently, the process is carried out at temperatures between 0° C. and 250° C., preferably between 50° C. and 220° C.

Process (E) according to the invention is preferably carried out under atmospheric pressure.

When carrying out process (E) according to the invention, the reactants of the formulae (VIII) or (VIIIa) and (V) and, if appropriate, the acid acceptor are generally employed in approximately equimolar amounts. However, it is also possible to use one or the other reactant in a larger excess (up to 5 mol).

Process (F) according to the invention is characterized in that thioamides of the formula (IX) are reacted with ketene acid halides of the formula (V), if appropriate in the presence of a diluent and if appropriate in the presence of an acid acceptor.

Diluents which can be employed in process variant (F) according to the invention are all inert organic solvents. The following can preferably be used: hydrocarbons, such as o-dichlorobenzene, tetralin, toluene and xylene, furthermore ethers, such as dibutyl ether, glycol dimethyl ether and diglycol dimethyl ether, moreover polar solvents, such as dimethyl sulphoxide, sulpholane, dimethylformamide or N-methyl-pyrrolidone.

Acid acceptors which can be used when carrying out process (F) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base or N,N-dimethyl-aniline.

When carrying out process (F) according to the invention, the reaction temperature can be varied within a substantial range. Expediently, the process is carried out at temperatures between 0° C. and 250° C., preferably between 20° C. and 220° C.

Process (F) according to the invention is preferably carried out under atmospheric pressure.

When carrying out process (F) according to the invention, the reactants of the formulae (IX) and (V) and, if appropriate, the acid acceptors are generally employed in approximately equimolar amounts. However, it is also possible to use one or the other reactant in a larger excess (up to 5 mol).

Process (Gα) is characterized in that compounds of the formulae (I-1-a) to (I-6-a) are reacted in each case with carboxylic acid halides of the formula (X), if appropriate in the presence of a diluent and if appropriate in the presence of an acid-binding agent.

Diluents which can be employed in process (Gα) according to the invention are all solvents which are inert to the acid halides. The following can preferably be used: hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. If the acid halide is sufficiently stable to hydrolysis, the reaction can also be carried out in the presence of water.

Acid-binding agents which are suitable for the reaction in accordance with process (Gα) according to the invention are all customary acid acceptors. The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and alkali metal hydroxides, such as sodium hydroxide and potassium hydroxide.

When carrying out process (Gα) according to the invention, the reaction temperature can be varied within a substantial range. In general, the process is carried out at temperatures between −20° C. and +150° C., preferably between 0° C. and 100° C.

When carrying out process (Gα) according to the invention, the starting substances of the formulae (I-1-a) to (I-6-a) and the carboxylic acid halide of the formula (X) are generally employed in each case in approximately equivalent amounts. However, it is also possible to employ the carboxylic acid halide in a larger excess (up to 5 mol). Working-up is carried out by customary methods.

Process (Gβ) is characterized in that compounds of the formulae (I-1-a) to (I-6-a) are reacted in each case with carboxylic anhydrides of the formula (XI), if appropriate in the presence of a diluent and if appropriate in the presence of an acid-binding agent.

Diluents which can be used in process (Gβ) according to the invention are preferably those which are also preferably suitable when using acid halides. Moreover, a carboxylic anhydride employed in an excess may also simultaneously act as the diluent.

Acid-binding agents which are optionally added in process (Gβ) are preferably those acid-binding agents which are also preferably suitable when using acid halides.

When carrying out process (Gβ) according to the invention, the reaction temperature can be varied within a substantial range. In general, the process is carried out at temperatures between −20° C. and +150° C., preferably between 0° C. and 100° C.

When carrying out process (Gβ) according to the invention, the starting substances of the formulae (I-1-a) to (I-6-a) and the carboxylic anhydride of the formula (XI) are generally employed in each case in approximately equivalent amounts. However, it is also possible to employ the carboxylic anhydride in a larger excess (up to 5 mol). Working-up is carried out by customary methods.

In general, a procedure is followed in which diluents and an excess of carboxylic anhydride and the carboxylic acid which forms are removed by distillation or by washing with an organic solvent or with water.

Process (H) is characterized in that compounds of the formulae (I-1-a) to (I-6-a) are reacted in each case with chloroformic esters or chloroformic thioesters of the formula (XII), if appropriate in the presence of a diluent and if appropriate in the presence of an acid-binding agent.

Acid-binding agents which are suitable in process (H) according to the invention are all customary acid acceptors. The following can preferably be used: tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Diluents which can be employed in process (H) according to the invention are all solvents which are inert to the chloroformic esters or chloroformic thioesters. The following can preferably be used: hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out process (H) according to the invention, the reaction temperature can be varied within a substantial range. The reaction temperature is generally between −20° C. and +100° C., preferably between 0° C. and 50° C.

Process (H) according to the invention is generally carried out under atmospheric pressure.

When carrying out process (H) according to the invention, the starting substances of the formulae (I-1-a) to (I-6-a) and the relevant chloroformic ester or chloroformic thioester of the formula (XII) are generally employed in each case in approximately equimolar amounts. However, it is also possible to employ one or the other reactant in a larger excess (up to 2 mol). Working up is carried out by customary methods. In general, a procedure is followed in which precipitated salts are removed and the reaction mixture which remains is concentrated by stripping off the diluent.

Process (I) according to the invention is characterized in that compounds of the formulae (I-1-a) to (I-6-a) are reacted in each case with (Iα) compounds of the formula (XIII) in the presence of a diluent and, if appropriate, in the presence of an acid-binding agent, or (Iβ) carbon disulphide and subsequently with alkyl halides of the formula (XIV), if appropriate in the presence of a diluent and if appropriate in the presence of a base.

In preparation process (Iα), approximately 1 mol of chloromonothioformic ester or chlorodithioformic ester of the formula (XIII) is reacted per mol of starting compound of the formulae (I-1-a) to (I-6-a) at 0 to 120° C., preferably at 20 to 60° C.

Suitable diluents which are optionally added are all inert polar organic solvents, such as ethers, amides, sulphones, sulphoxides, but also halogenoalkanes.

Dimethyl sulphoxide, tetrahydrofuran, dimethylformamide or methylene chloride are preferably employed.

If, in a preferred embodiment, the enolate salt of the compounds (I-1-a) to (I-6-a) is synthesized by adding strong deprotonating agents, such as, for example, sodium hydride or potassium tertiary butylate, a further addition of acid-binding agents can be dispensed with.

If acid-binding agents are employed, then suitable substances are customary inorganic or organic bases, examples which may be mentioned being sodium hydroxide, sodium carbonate, potassium carbonate, pyridine and triethylamine.

The reaction can be carried out under atmospheric pressure or elevated pressure, preferably under atmospheric pressure. Working-up is carried out by customary methods.

In preparation process (Iβ), the equimolar amount or an excess of carbon disulphide is added in each case per mol of starting compounds of the formulae (I-1-a) to (I-6-a). This process is preferably carried out at temperatures from 0 to 50° C., in particular 20 to 30° C.

Frequently, it is expedient first to prepare the corresponding salt from the compounds of the formulae (I-1-a) to (I-6-a) by adding a base (such as, for example, potassium tertiary butylate or sodium hydride). The compounds (I-1-a) to (I-6-a) are reacted with carbon disulphide in each case for such a period of time that the formation of the intermediate is complete, for example after stirring at room temperature for several hours.

Bases which can be employed in process (Iβ) are all customary proton acceptors. The following are preferably suitable: alkali metal hydrides, alkali metal alcoholates, alkali metal carbonates, alkali metal hydrogen carbonates, alkaline earth metal carbonates, alkaline earth metal hydrogen carbonates or nitrogen bases. Examples which may be mentioned are, for example, sodium hydride, sodium methanolate, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

Diluents which can be used in this process are all customary solvents.

The following can preferably be used: aromatic hydrocarbons, such as benzene or toluene, alcohols, such as methanol, ethanol, isopropanol or ethylene glycol, nitrites, such as acetonitrile, ethers, such as tetrahydrofuran or dioxane, amides, such as dimethylformamide, or other polar solvents, such as dimethyl sulphoxide or sulpholane.

The further reaction with the alkyl halide of the formula (XIV) is preferably carried out at 0 to 70° C., in particular at 20 to 50° C. At least the equimolar amount of alkyl halide is employed.

The process is carried out under atmospheric pressure or under elevated pressure, preferably under atmospheric pressure.

Again, working-up is carried out by customary methods.

Process (J) according to the invention is characterized in that compounds of the formulae (I-1-a) to (I-6-a) are reacted in each case with sulphonyl chlorides of the formula (XV), if appropriate in the presence of a diluent and if appropriate in the presence of an acid-binding agent.

In preparation process (J), approximately 1 mol of sulphonyl chloride of the formula (XV) is reacted per mole of starting compound of the formulae (I-1-a) to (I-6-a) at −20 to 150° C., preferably at 20 to 70° C.

Process (J) is preferably carried out in the presence of a diluent.

Diluents which can be used are all inert polar organic solvents, such as ethers, amides, nitrites, sulphones, sulphoxides, or halogenated hydrocarbons, such as methylene chloride.

Dimethyl sulphoxide, tetrahydrofuran, dimethylformamide or methylene chloride are preferably employed.

If, in a preferred embodiment, the enolate salt of the compounds I-1-a) to (I-6-a) is synthesized by adding strong deprotonating agents (such as, for example, sodium hydride or potassium tertiary butylate) a further addition of acid-binding agents can be dispensed with.

If acid-binding agents are employed, then suitable substances are customary inorganic or organic bases, examples which may be mentioned being sodium hydroxide, sodium carbonate, potassium carbonate, pyridine and triethylamine.

The reaction can be carried out under atmospheric pressure or elevated pressure, preferably under atmospheric pressure. Working-up is carried out by customary methods.

Process (K) according to the invention is characterized in that compounds of the formulae (I-1-a) to (I-6-a) are reacted in each case with phosphorus compounds of the formula (XVI), if appropriate in the presence of a diluent and if appropriate in the presence of an acid-binding agent.

In preparation process (K), 1 to 2, preferably 1 to 1.3, mol of the phosphorus compound of the formula (XVI) are reacted per mol of the compounds I-1-a) to (I-6-a) at temperatures between −40° C. and 150° C., preferably between −10 and 110° C., to obtain compounds of the formulae (I-1-e) to (I-6-e).

Process (K) is preferably carried out in the presence of a diluent.

Suitable diluents are all inert polar organic solvents, such as ethers, amides, nitrites, alcohols, sulphides, sulphones, sulphoxides and the like.

Acetonitrile, dimethyl sulphoxide, tetrahydrofuran, dimethylformamide or methylene chloride are preferably employed.

Suitable acid-binding agents which are optionally added are customary inorganic or organic bases, such as hydroxides, carbonates or amines. Examples which may be mentioned are sodium hydroxide, sodium carbonate, potassium carbonate, pyridine and triethylamine.

The reaction can be carried out under atmospheric pressure or under elevated pressure, preferably under atmospheric pressure. Working-up is carried out by customary methods of organic chemistry. The end products are preferably purified by crystallization, chromatography or by so-called "incipient distillation", i.e. removal of the volatile components in vacuo.

Process (L) is characterized in that compounds of the formulae (I-1-a) to (I-6-a) are reacted in each case with metal hydroxides or metal alkoxides of the formula (XVII) or amines of the formula (XVIII), if appropriate in the presence of a diluent.

Diluents which can be employed in process (L) according to the invention are, preferably, ethers, such as tetrahydrofuran, dioxane or diethyl ether, or else alcohols, such as methanol, ethanol or isopropanol, but also water. Process (L) according to the invention is generally carried out under atmospheric pressure. The reaction temperature is generally between −20° C. and 100° C., preferably between 0° C. and 50° C.

Process (M) according to the invention is characterized in that compounds of the formulae (I-1-a) to (I-6-a) are reacted in each case with (Mα) compounds of the formula (XIX), if appropriate in the presence of a diluent and if appropriate in the presence of a catalyst, or (Mβ) with compounds of the formula (XX), if appropriate in the presence of a diluent and if appropriate in the presence of an acid-binding agent.

In preparation process (Mα), approximately 1 mol of isocyanate of the formula (XIX) is reacted per mole of starting compound of the formulae (I-1-a) to (I-6-a) at 0 to 100° C., preferably at 20 to 50° C.

Process (Mα) is preferably carried out in the presence of a diluent.

Suitable diluents are all inert organic solvents, such as ethers, amides, nitrites, sulphones or sulphoxides.

If appropriate, catalysts may be added to accelerate the reaction. Catalysts which can be employed very advantageously are organotin compounds, such as, for example, dibutyltin dilaurate.

The process is preferably carried out under atmospheric pressure.

In preparation process (Mβ), approximately 1 mol of carbamoyl chloride of the formula (XX) is reacted per mole of starting compound of the formulae (I-1-a) to (I-6-a) at 0 to 150° C., preferably at 20 to 70° C.

Diluents which are optionally added are all inert polar organic solvents, such as ethers, amides, sulphones, sulphoxides or halogenated hydrocarbons.

Dimethyl sulphoxide, tetrahydrofuran, dimethylformamide or methylene chloride are preferably employed.

If, in a preferred embodiment, the enolate salt of the compounds (I-1-a) to (I-6-a) is synthesized by adding strong deprotonating agents, such as, for example, sodium hydride or potassium tertiary butylate, a further addition of acid-binding agents can be dispensed with.

If acid-binding agents are employed, then suitable substances are customary inorganic or organic bases, examples which may be mentioned being sodium hydroxide, sodium carbonate, potassium carbonate, triethylamine or pyridine.

The reaction can be carried out under atmospheric pressure or elevated pressure, preferably under atmospheric pressure. Working-up is carried out by customary methods.

The active compounds are suitable for combating animal pests, preferably arthropods and nematodes, particularly insects and arachnids, encountered in agriculture, in forests, in the protection of stored products and materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides,* Melanoplus differentialis and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctaturn, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acaris siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaricidal activity.

They can be employed particularly successfully for combating insects which damage plants, such as, for example, against the larvae of the mustard beetle (*Phaedon cochleariae*) or against the larvae of the green rice leafhopper (*Nephotettix cincticeps*) or against the caterpillars of the diamond-back moth (*Plutella maculipennis*).

The active compounds according to the invention can furthermore be used as defoliants, desiccants, agents for destroying broad-leaved plants and, especially, as weedkillers. By weeds, in the broadest sense, there are to be understood all plants which grow in locations where they are not wanted. Whether the substances according to the invention act as total or selective herbicides depends essentially on the amount used.

The dosage rates of the active compounds according to the invention which are required for combating weeds are between 0.001 and 10 kg/ha, preferably between 0.005 and 5 kg/ha.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Sacchanim, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are highly suitable for selectively combating monocotyledon weeds in dicotyledon cultures by the pre- and post-emergence method. For example they can be employed very successfully for combating grass weeds in cotton or sugar beet.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

The active compound according to the invention can be present in their commercially available formulations and in the use forms, prepared from these formulations, as a mixture with other active compounds, such as insecticides, attractants, sterilants, acaricides, nematicides, fungicides, growth-regulating substances or herbicides. The insecticides include, for example, phosphates, carbamates, carboxylates, chlorinated hydrocarbons, phenylureas, substances produced by microorganisms, and the like.

Examples of particularly advantageous components for the mixtures are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl)acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bacteincides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phermedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlorotoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imaza-methabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfiron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphesate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 up to 95% by weight of active compound, preferably between 0.0001 and 1% by weight.

The compounds are employed in a customary manner appropriate for the use forms.

When used against hygiene pests and stored-product pests, the active compound is distinguished by an outstanding residual action on wood and clay and by a good stability to alkali on limed substrates.

The active compounds according to the invention are not only active against plant pests, hygiene pests and stored-product pests but also, in the field of veterinary medicine, against animal parasites (ectoparasites) such as scaly ticks, Argasidae, scab mites, Trombidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Wemeckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomnitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica,* Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp., Varroa spp.

From the order of the Actinedida (Prostigmata) and Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

For example, they show an outstanding activity against *Boophilus microplus* and *Lucilia cuprina.*

The active compounds of the formula (I) according to the invention are also suitable for combating arthropods which infest agricultural productive livestock such as, for example, cattle, sheep, goats, horses, pigs, donkeys, camels, buffalo, rabbits, chickens, turkeys, ducks, geese and bees, other domestic animals, such as, for example, dogs, cats, cage birds and aquarium fish, and also so-called experimental animals, such as, for example, hamsters, guinea pigs, rats and mice. By combating these arthropods, cases of death and reductions in productivity (for meat, milk, wool, hides, eggs, honey etc) should be diminished, so that more economic and simpler animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intra-muscular, subcutaneous, intravenous, intraperitoneal, etc.), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used as a chemical bath.

Furthermore, it has been found that the compounds of the formula I according to the invention have a potent insecticidal action against insects which destroy industrial materials.

The following insects may be mentioned by way of example and of being preferred, but not by way of limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Dermaptera, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.* bristletails, such as *Lepisma saccharina.*

Industrial materials are to be listed as meaning, in the present context, non-live materials such as, preferably, synthetic materials, glues, sizes, paper and board, leather, wood and derived timber products, and paints.

The material to be protected against attack by insects is very particularly preferably wood and derived timber products.

Wood and derived timber products which can be protected by the agent according to the invention or by compositions comprising it are to be understood as meaning, for example, construction timber, wooden beams, railway sleepers, bridge components, jetties, wooden vehicles, boxes, pallets, containers, telephone poles, wood laggings, windows and doors made of wood, plywood, particle board, joiner's work, or wood products which, quite generally, are used in construction or in joinery.

The active compounds can be used as such, in the form of concentrates or generally customary formulations, such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if appropriate desiccants and UV stabilizers, and, if appropriate, colorants and pigments, and other processing auxiliaries.

The insecticidal compositions or concentrates used for the protection of wood and timber products comprise the active compound according to the invention in a concentration of 0.0001 to 95% by weight, in particular 0.001 to 60% by weight.

The amount of the compositions or concentrates employed depends on the species and the occurrence of the insects and on the medium. The optimum amount used can be determined in each case upon use by test series. However, in general it suffices to employ 0.0001 to 20% by weight, preferably 0.001 to 10% by weight, of the active compound based on the material to be protected.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

The organochemical solvents employed are preferably oily or oil-like solvents with an evaporation number of above 35 and a flash point of above 30° C., preferably above 45° C. Substances which are used as such oily and oil-type solvents of low volatility which are insoluble in water are suitable mineral oils or their aromatic fractions or mineral-oil-comprising solvent mixtures, preferably white spirit, petroleum and/or alkylbenzene.

It is advantageous. to use mineral oils with a boiling range of −170 to 220° C., white spirit with a boiling range of 170 to 220° C., spindle oil with a boiling point of 250 to 350° C., petroleum or aromatics of a boiling range of 160 to 280° C., spirit of turpentine and the like.

In a preferred embodiment, the substances used are liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene.

The organic oily or oil-type solvents of low volatility with an evaporation number above 35 and a flashpoint of above 30° C., preferably 45° C., can be replaced in part by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organo-chemical solvent or solvent mixture is replaced by an aliphatic polar organochemical solvent or solvent mixture. Substances which are preferably used are aliphatic organochemical solvents containing hydroxyl and/or ester and/or ether groups, such as, for example, glycol ethers, esters and the like.

Organochemical binders which are used within the scope of the present invention are the binding drying oils and/or synthetic resins which are known per se, can be diluted with water and/or are soluble, dispersible or emulsifiable in the organochemical solvents employed, in particular binders composed of or comprising an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene-coumarone resin, silicone resin, drying vegetable and/or drying oils and/or physically drying binders based on a natural and/or synthetic resin.

The synthetic resin used as binder can be employed in the form of an emulsion, dispersion or solution. Substances which can also be used as binders are bitumen or bituminous substances in amounts of up to 10% by weight. In addition, colorants, pigments, water repellants, odoriferous substances and inhibitors or anticorrosives which are known per se can be employed, inter alia.

The composition or concentrate preferably comprises, in accordance with the invention, at least one alkyd resin or modified alkyd resin and/or a drying vegetable oil as the organochemical binder. Substances which are preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds or crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, phosphoric esters, such as tributyl phosphate, adipic esters, such as di-(2-ethylhexyl) adipate, stearates, such as butyl stearate or amyl stearate, oleates, such as butyl oleate, glycerol ethers or higher-molecular-weight glycol ethers, glycerol esters and p-toluenesulphonic esters.

Fixatives are based chemically on polyvinyl alkyl ethers, such as, for example, polyvinyl methyl ether, or ketones, such as benzophenone or ethylenebenzophenone.

Another suitable solvent or diluent is, in particular, water, if appropriate in a mixture with one or more of the above-mentioned organochemical solvents or diluents, emulsifiers and dispersants.

A particularly effective protection of wood is achieved by means of industrial-scale impregnating processes, for example vacuum, double-vaccum or pressure processes.

If appropriate, the ready-to-use compositions can comprise other insecticides and, if appropriate, one or more other fungicides.

Additional components which may be admixed are preferably the insecticides and fungicides mentioned in WO 94/29 268. The compounds mentioned in the above document are expressly part of the present application.

Components which may very particularly preferably be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octyl-isothiazolin-3-one and 4,5-dichloro-N-octylisothiazolin-3-one.

Preparation and use of the active compounds according to the invention can be seen from the examples which follow.

PREPARATION EXAMPLES

Example (I-1-a-1)

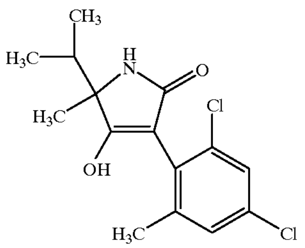

25.1 g (0.072 mol) of the compound of Example (II-1) in 160 ml of anhydrous toluene are added dropwise at reflux temperature to 17.36 g (0.159 mol) of potassium tert-butylate in 55 ml of anhydrous tetrahydrofuran (THF), and the mixture is stirred under reflux for 1.5 hours. For working up, 230 ml of water are added, the aqueous phase is separated off, the toluene phase is extracted using 120 ml of water, and the aqueous phases are combined, washed with toluene and acidified with approximately 25 ml of concentrated HCl at 10 to 20° C. The product is filtered off with suction, washed, dried and washed by stirring in methyl tert-butyl (MTB) ethyl/n-hexane.

Yield: 16.7 g (73% of theory), m.p.: 159° C.

The following compounds of the formula (I-1-a) are obtained analogously or in accordance with the general preparation instructions:

TABLE 10

(I-1-a)

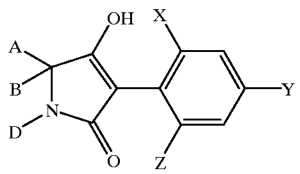

| Example No. | X | Y | Z | B | A | D | M.p. ° C. | Isomer |
|---|---|---|---|---|---|---|---|---|
| I-1-a-2 | Cl | Cl | $CH_3$ | | $—(CH_2)_3—CHCH_3—CH_2—$ | | H | 192 | β |
| I-1-a-3 | Cl | Cl | $CH_3$ | | $—(CH_2)_5—$ | H | 176 | — |
| I-1-a-4 | Cl | Cl | $CH_3$ | | $—(CH_2)_2—CHCH_3—(CH_2)_2—$ | H | 189 | β |
| I-1-a-5 | Cl | Cl | $CH_3$ | | $—(CH_2)_2—O—(CH_2)_2—$ | H | >220 | — |
| I-1-a-6 | Cl | Cl | $CH_3$ | | $—(CH_2)_2—CHOCH_3—(CH_2)_2—$ | H | 216 | β |
| I-1-a-7 | Cl | $CH_3$ | Cl | | $—(CH_2)_2—CHCH_3—(CH_2)_2—$ | H | >220 | β |
| I-1-a-8 | Cl | $CH_3$ | Cl | | $—(CH_2)_3—CHCH_3—CH_2—$ | H | 209 | β |
| I-1-a-9 | Cl | $CH_3$ | Cl | | $—(CH_2)_5—$ | H | >220 | — |
| I-1-a-10 | Cl | $CH_3$ | Cl | | $—(CH_2)_2—O—(CH_2)_2—$ | H | >220 | — |
| I-1-a-11 | Cl | $CH_3$ | Cl | i-$C_3H_7$ | $CH_3$ | H | >220 | — |

TABLE 10-continued (I-1-a)

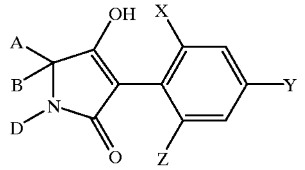

| Example No. | X | Y | Z | B | A | D | M.p. ° C. | Isomer |
|---|---|---|---|---|---|---|---|---|
| I-1-a-12 | Cl | $CH_3$ | Cl | $—(CH_2)_2—CHOCH_3—(CH_2)_2—$ | | H | >220 | β |
| I-1-a-13 | Cl | Cl | $CH_3$ | H | $—(CH_2)_4—$ | | >220 | — |
| I-1-a-14 | Cl | Cl | $CH_3$ | H | H | $i\text{-}C_3H_7$ | >220 | — |
| I-1-a-15 | Cl | Cl | $CH_3$ | $—(CH_2)_2—CHOCH_3—(CH_2)_2—$ | | H | >220 | α |
| I-1-a-16 | Br | Cl | $CH_3$ | $—(CH_2)_3—CHCH_3—CH_2—$ | | H | 148 | β |
| I-1-a-17 | Br | Cl | $CH_3$ | $—(CH_2)_2—CHOCH_3—(CH_2)_2—$ | | H | >220 | β |
| I-1-a-18 | Br | Cl | $CH_3$ | $CH_3$ | $CH_3$ | H | >220 | — |
| I-1-a-19 | Br | Cl | $CH_3$ | $CH_3$ | $i\text{-}C_3H_7$ | H | >200 | — |
| I-1-a-20 | Br | $CH_3$ | Cl | $—(CH_2)_2—CHCH_3—(CH_2)_2—$ | | H | 219 | β |
| I-1-a-21 | Br | $CH_3$ | Cl | $CH_3$ | $CH_3$ | H | 206 | — |
| I-1-a-22 | Cl | Br | $CH_3$ | $—(CH_2)_2—CH(CH_3)—(CH_2)_2—$ | | H | >220 | β |
| I-1-a-23 | Cl | Br | $CH_3$ | $—(CH_2)_2—O—(CH_2)_2—$ | | H | >220 | — |
| I-1-a-24 | Cl | Br | $CH_3$ | $—(CH_2)_2—CHOCH_3—(CH_2)_2—$ | | H | >220 | β |
| I-1-a-25 | Cl | $CH_3$ | Cl | $CH_3$ | $CH_3$ | H | >220 | — |
| I-1-a-26 | Cl | $CH_3$ | Cl | H | $—CH_2—CHCH_3—CHCH_3—$ | | 201 | |

EXAMPLE (I-1-b-1)

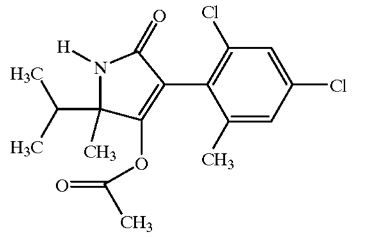

4.7 g of (0.015 mol) of the compound of Example (I-1-a-1) and 4.2 ml (30 mmol) of triethylamine in 70 ml of absolute methylene chloride are treated with 2.14 ml (0.03 mol) of acetyl chloride in 5 ml of absolute methylene chloride at 0 to 10° C. The mixture is stirred at room temperature until a thin-layer chromatography check confirms that the reaction has ended. For working up, the mixture is washed twice using 50 ml of 0.5 N sodium hydroxide solution, dried over magnesium sulphate and evaporated. The crude product is recrystallized from MTB ether/n-hexane.

Yield: 2.30 g (43% of theory), m.p.: 211° C.

The following compounds of the formula (I-b-1) are obtained analogously or in accordance with the general preparation instructions:

TABLE 11

(I-1-b)

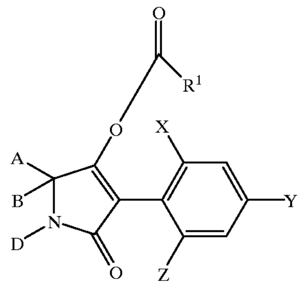

| Example No. | X | Y | Z | B | A | D | $R^1$ | M.p. ° C. | Isomer |
|---|---|---|---|---|---|---|---|---|---|
| I-1-b-2 | Cl | Cl | $CH_3$ | $—(CH_2)_3—CHCH_3—CH_2—$ | | H | $CH_3—$ | >220 | β |
| I-1-b-3 | Cl | Cl | $CH_3$ | $—(CH_2)_3—CHCH_3—CH_2—$ | | H | $i\text{-}C_3H_7—$ | 191 | β |
| I-1-b-4 | Cl | Cl | $CH_3$ | $—(CH_2)_3—CHCH_3—CH_2—$ | | H | $H_5C_2—O—CH_2—$ | 168 | β |
| I-1-b-5 | Cl | Cl | $CH_3$ | $—(CH_2)_3—CHCH_3—CH_2—$ | | H | $C_6H_5—$ | >220 | β |
| I-1-b-6 | Cl | Cl | $CH_3$ | $—(CH_2)_3—CHCH_3—CH_2—$ | | H | $t\text{-}C_4H_9—CH_2—$ | 218 | β |

TABLE 11-continued (I-1-b)

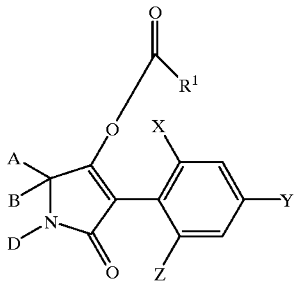

| Example No. | X | Y | Z | B | A | D | $R^1$ | M.p. ° C. | Isomer |
|---|---|---|---|---|---|---|---|---|---|
| I-1-b-7 | Cl | Cl | $CH_3$ | | $—(CH_2)_5—$ | H | $CH_3—$ | >220 | — |
| I-1-b-8 | Cl | Cl | $CH_3$ | | $—(CH_2)_5—$ | H | $i-C_3H_7—$ | 188 | — |
| I-1-b-9 | Cl | Cl | $CH_3$ | | $—(CH_2)_5—$ | H | $t-C_4H_9—CH_2—$ | >220 | — |
| I-1-b-10 | Cl | Cl | $CH_3$ | | $—(CH_2)_2—CHCH_3—CH_2—$ | H | $CH_3—$ | >220 | β |
| I-1-b-11 | Cl | Cl | $CH_3$ | | $—(CH_2)_2—CHCH_3—CH_2—$ | H | $i-C_3H_7—$ | 189 | β |
| I-1-b-12 | Cl | Cl | $CH_3$ | | $—(CH_2)_2—CHCH_3—CH_2—$ | H | $4-Cl—C_6H_4—$ | >220 | β |
| I-1-b-13 | Cl | Cl | $CH_3$ | | $—(CH_2)_2—CHCH_3—CH_2—$ | H | $H_3CO—CH_2—CHCH_3—$ | >220 | β |
| I-1-b-14 | Cl | Cl | $CH_3$ | | $—(CH_2)_2—O—(CH_2)_2—$ | H | $CH_3—$ | 216 | — |
| I-1-b-15 | Cl | Cl | $CH_3$ | | $—(CH_2)_2—O—(CH_2)_2—$ | H | $i-C_3H_7—$ | 187 | — |
| I-1-b-16 | Cl | Cl | $CH_3$ | | $—(CH_2)_2—O—(CH_2)_2—$ | H | $s-C_4H_9—$ | 198 | — |
| I-1-b-17 | Cl | Cl | $CH_3$ | | $—(CH_2)_2—O—(CH_2)_2—$ | H | $C_2H_5—$ | >220 | — |
| I-1-b-18 | Cl | $CH_3$ | Cl | | $—(CH_2)_2—CHCH_3—(CH_2)_2—$ | H | $i-C_3H_7—$ | >220 | β |
| I-1-b-19 | Cl | $CH_3$ | Cl | | $—(CH_2)_3—CHCH_3—CH_2—$ | H | $CH_3—$ | >220 | β |
| I-1-b-20 | Cl | $CH_3$ | Cl | | $—(CH_2)_3—CHCH_3—CH_2—$ | H | $i-C_3H_7—$ | 190 | β |
| I-1-b-21 | Cl | $CH_3$ | Cl | | $—(CH_2)_2—O—(CH_2)_2—$ | H | $CH_3—$ | >220 | — |
| I-1-b-22 | Cl | $CH_3$ | Cl | | $—(CH_2)_2—O—(CH_2)_2—$ | H | $i-C_3H_7—$ | 215 | — |
| I-1-b-23 | Cl | CH | Cl | $i-C_3H_7$ | $CH_3$ | H | $CH_3—$ | 209 | — |
| I-1-b-24 | Cl | $CH_3$ | Cl | $i-C_3H_7$ | $CH_3$ | H | $i-C_3H_7—$ | 105 | — |
| I-1-b-25 | Cl | $CH_3$ | Cl | | $—(CH_2)_2—CHOCH_3—(CH_2)_2—$ | H | $i-C_3H_7—$ | 183 | β |
| I-1-b-26 | Cl | $CH_3$ | Cl | | $—(CH_2)2—CHOCH_3—(CH_2)_2—$ | H | $H_5C_2—O—CH_2—$ | >220 | β |
| I-1-b-27 | Cl | $CH_3$ | Cl | | $—(CH_2)_2—CHOCH_3—(CH_2)_2—$ | H | $t-C_4H_9—CH_2—$ | 219 | β |
| I-1-b-28 | Cl | Cl | $CH_3$ | | $—(CH_2)_2—CHOCH_3—(CH_2)_2—$ | H | $i-C_3H_7—$ | >220 | β |
| I-1-b-29 | Cl | Cl | $CH_3$ | | $—(CH_2)_2—CHOCH_3—(CH_2)_2—$ | H | $H_5C_2—O—CH_2—$ | >220 | β |
| I-1-b-30 | Cl | Cl | $CH_3$ | | $—(CH_2)_2—CHOCH_3—(CH_2)_2—$ | H | $t-C_4H_9—CH_2—$ | 197 | β |
| I-1-b-31 | Cl | Cl | $CH_3$ | | $—(CH_2)_2—CHOCH_3—(CH_2)_2—$ | H | $i-C_3H_7—$ | 193 | α[a)] |
| I-1-b-32 | Cl | Cl | $CH_3$ | | $—(CH_2)_2—CHOCH_3—(CH_2)_2—$ | H | $H_5C_2—O—CH_2—$ | 171 | α[a)] |
| I-1-b-33 | Cl | Cl | $CH_3$ | | $—(CH_2)_2—CHCH_3—(CH_2)_2—$ | H | $C_2H_5O—CH_2—$ | 156 | β |
| I-1-b-34 | Cl | Cl | $CH_3$ | | $—(CH_2)_2—CHCH_3—(CH_2)_2—$ | H | 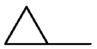 | 219 | β |
| I-1-b-35 | Cl | Cl | $CH_3$ | | $—(CH_2)_2—CHCH_3—(CH_2)_2—$ | H | 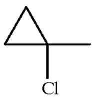 | 185 | β |
| I-1-b-36 | Cl | Cl | $CH_3$ | | $—(CH_2)_2—CHCH_3—(CH_2)_2—$ | H | $i-C_4H_9—$ | 160 | β |
| I-1-b-37 | Cl | Cl | $CH_3$ | | $—(CH_2)_2—CHCH_3—(CH_2)_2—$ | H | 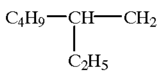 | 141 | β |
| I-1-b-38 | Cl | Cl | $CH_3$ | | $—(CH_2)_2—CHCH_3—(CH_2)_2—$ | H | cyclohexyl | >220 | β |
| I-1-b-39 | Cl | Cl | $CH_3$ | | $—(CH_2)_2—CHCH_3—(CH_2)_2—$ | H | $C(CH_3)_2{=}CH—$ | 219 | β |
| I-1-b-40 | Cl | Cl | $CH_3$ | | $—(CH_2)_2—CHCH_3—(CH_2)_2—$ | H | 3-(6-Cl-pyridyl)- | 167 | β |
| I-1-b-41 | Cl | Cl | $CH_3$ | | $—(CH_2)_2—CHCH_3—(CH_2)_2—$ | H | 2-thienyl- | 213 | β |
| I-1-b-42 | Cl | Cl | $CH_3$ | | $—(CH_2)_2—CHCH_3—(CH_2)_2—$ | H | 2-furanyl- | >220 | β |
| I-1-b-43 | Cl | Cl | $CH_3$ | H | | $—(CH_2)_4—$ | $t-C_4H_9—$ | 147 | — |
| I-1-b-44 | Br | Cl | $CH_3$ | $CH_3$ | $CH_3$ | H | $i-C_4H_9—$ | 164 | — |
| I-1-b-45 | Cl | Br | $CH_3$ | | $—(CH_2)_2—CHCH_3—(CH_2)_2—$ | H | $CH_3—$ | >220 | β |
| I-1-b-46 | Cl | Br | $CH_3$ | | $—(CH_2)_2—CHCH_3—(CH_2)_2—$ | H | $i-C_3H_7—$ | 210 | β |
| I-1-b-47 | Cl | Br | $CH_3$ | | $—(CH_2)_2—CHCH_3—(CH_2)_2—$ | H | $C_2H_5—O—CH_2—$ | 158 | β |
| I-1-b-48 | Cl | Br | $CH_3$ | | $—(CH_2)_2—CHCH_3—(CH_2)_2—$ | H | $4-Cl-C_6H_4—$ | 213 | β |
| I-1-b-49 | Cl | Br | $CH_3$ | | $—(CH_2)_2—O—(CH_2)_2—$ | H | $i-C_3H_7—$ | 216 | — |
| I-1-b-50 | Cl | Br | $CH_3$ | | $—(CH_2)_2—O—(CH_2)_2—$ | H | $i-C_4H_9—$ | >220 | — |
| I-1-b-51 | Cl | Br | $CH_3$ | | $—(CH_2)_2—O—(CH_2)_2—$ | H | $C_2H_5—O—CH_2—$ | 217 | — |

TABLE 11-continued (I-1-b)

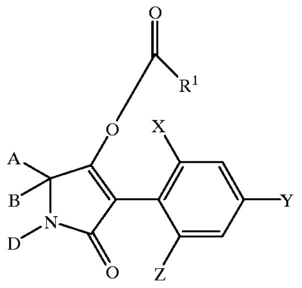

| Example No. | X | Y | Z | B | A | D | $R^1$ | M.p. ° C. | Isomer |
|---|---|---|---|---|---|---|---|---|---|
| I-1-b-52 | Cl | Br | $CH_3$ | | $—(CH_2)_2—O—(CH_2)_2—$ | H | $C(CH_3)_2{=}CH—$ | 205 | — |
| I-1-b-53 | Cl | Br | $CH_3$ | | $—(CH_2)_2—CHOCH_3—(CH_2)_2—$ | H | $i\text{-}C_3H_7—$ | 192 | β |
| I-1-b-54 | Cl | Br | $CH_3$ | | $—(CH_2)_2—CHOCH_3—(CH_2)_2—$ | H | $C_2H_5—O—CH_2—$ | 173 | β |
| I-1-b-55 | Cl | $CH_3$ | Cl | $CH_3$ | $CH_3$ | H | $i\text{-}C_3H_7—$ | 161 | — |
| I-1-b-56 | Cl | $CH_3$ | Cl | H | H | $i\text{-}C_3H_7$ | $t\text{-}C_4H_9—$ | 104 | |
| I-1-b-57 | Cl | $CH_3$ | Cl | H | $—CH_2—CHCH_3—CHCH_3—$ | | $t\text{-}C_4H_9$ | oil | |

[a)]The α isomers were obtained by chromatographic separation of a mixture of α and β isomers on silica gel using methylene chloride/ethyl acetate 2:1 as the eluent.

EXAMPLE (I-1-c-1)

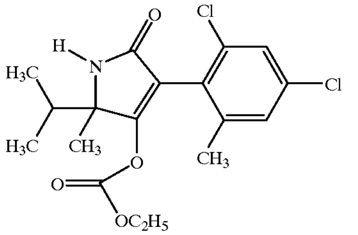

1.8 ml (18 mmol) of ethyl chloroformate in 5 ml of absolute methylene chloride are added dropwise at 0 to 10° C. to 4.7 g (0.015 mol) of the compound of Example (I-1-a-1) and 2.1 ml of triethylamine in 70 ml of absolute THF, and the mixture is stirred at room temperature until a thin-layer chromatography check confirms the reaction has ended. For working-up, the mixture is washed twice using 50 ml of 0.5 N sodium hydroxide solution, dried over magnesium sulphate and evaporated.

Yield: 4.0 g (69% of theory), m.p.: >220° C.

The following compounds of the formula (I-1-c) are obtained analogously or in accordance with the general preparation instructions:

TABLE 12

(I-1-c)

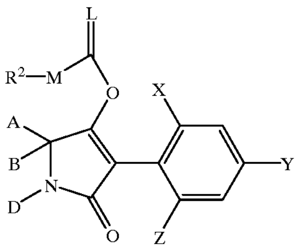

| Example No. | X | Y | Z | B | A | D | L | M | $R^2$ | M.p. ° C. | Isomer |
|---|---|---|---|---|---|---|---|---|---|---|---|
| I-1-c-2 | Cl | Cl | $CH_3$ | | $—(CH_2)_3—CHCH_3—CH_2—$ | H | O | O | $C_2H_5—$ | 196 | β |
| I-1-c-3 | Cl | Cl | $CH_3$ | | $—(CH_2)_5—$ | H | O | O | $C_2H_5—$ | 182 | — |
| I-1-c-4 | Cl | Cl | $CH_3$ | | $—(CH_2)_2—CHCH_3—(CH_2)_2—$ | H | O | O | $C_2H_5—$ | 196 | β |
| I-1-c-5 | Cl | Cl | $CH_3$ | | $—(CH_2)_2O—(CH_2)_2—$ | H | O | O | $C_2H_5—$ | >220 | — |
| I-1-c-6 | Cl | $CH_3$ | Cl | | $—(CH_2)_2—CHCH_3—(CH_2)_2—$ | H | O | O | $C_2H_5—$ | 201 | β |
| I-1-c-7 | Cl | $CH_3$ | Cl | | $—(CH_2)_3—CHCH_3—CH_2—$ | H | O | O | $C_2H_5—$ | 206 | β |
| I-1-c-8 | Cl | $CH_3$ | Cl | | $—(CH_2)_2—O—(CH_2)_2—$ | H | O | O | $C_2H_5—$ | 197 | — |
| I-1-c-9 | Cl | $CH_3$ | Cl | $CH_3$ | $i\text{-}C_3H_7$ | H | O | O | $C_2H_5—$ | 174 | — |
| I-1-c-10 | Cl | $CH_3$ | Cl | | $—(CH_2)_2—CHOCH_3—(CH_2)_2—$ | H | O | O | $C_2H_5—$ | >220 | β |
| I-1-c-11 | Cl | Cl | $CH_3$ | | $—(CH_2)_2—CHOCH_3—(CH_2)_2—$ | H | O | O | $C_2H_5—$ | 176 | β |
| I-1-c-12 | Cl | Cl | $CH_3$ | | $—(CH_2)_2—CHCOH_3—(CH_2)_2—$ | H | O | O | $C_2H_5—$ | 198 | α[a)] |

TABLE 12-continued (I-1-c)

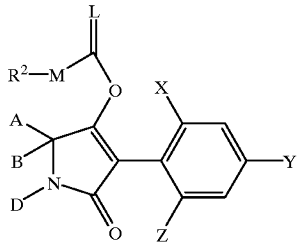

| Example No. | X | Y | Z | B | A | D | L | M | $R^2$ | M.p. ° C. | Isomer |
|---|---|---|---|---|---|---|---|---|---|---|---|
| I-1-c-13 | Cl | Cl | $CH_3$ | | $—(CH_2)_2—CHCH_3—(CH_2)_2—$ | H | O | O | $i-C_4H_9—$ | 201 | β |
| I-1-c-14 | Cl | Cl | $CH_3$ | | $—(CH_2)_2—CHCH_3—(CH_2)_2—$ | H | O | O | $C_6H_5—$ | >220 | β |
| I-1-c-15 | Cl | Cl | $CH_3$ | | $—(CH_2)_2—CHCH_3—(CH_2)_2—$ | H | O | O | $C_6H_5—CH_2—$ | >220 | β |
| I-1-c-16 | Cl | Cl | $CH_4$ | | $—(CH_2)_2—CHCH_3—(CH_2)_2—$ | H | O | O | $s-C_4H_9—$ | 206 | β |
| I-1-c-17 | Cl | Cl | $CH_3$ | | $—(CH_2)_2—CHCH_3—(CH_2)_2—$ | H | O | S | $t-C_4H_9—CH_2—$ | 232 | β |
| I-1-c-18 | Cl | Cl | $CH_3$ | | $—(CH_2)_2—CHCH_3—(CH_2)_2—$ | H | O | S | $s-C_4H_9—$ | 205 | β |
| I-1-c-19 | Cl | Cl | $CH_3$ | | $—(CH_2)_2—CHCH_3—(CH_2)_2—$ | H | O | S | $i-C_3H_7—$ | 218–220 | β |
| I-1-c-20 | Cl | Cl | $CH_2$ | | $—(CH_2)_2—CHCH_3—(CH_2)_2—$ | H | O | S | $C_6H_5—CH_2—$ | 179–181 | β |
| I-1-c-21 | Cl | Cl | $CH_3$ | | $—(CH_2)_2—CHCH_3—(CH_2)_2—$ | H | O | S | $t-C_4H_9—$ | 245–247 | β |
| I-1-c-22 | Cl | Cl | $CH_3$ | H | $—(CH_2)_4—$ | | O | S | $t-C_4H_9—$ | oil | |
| I-1-c-23 | Cl | Cl | $CH_3$ | H | $—(CH_2)_4—$ | | O | S | $t-C_4H_9—CH_2—$ | oil | |
| I-1-c-24 | Cl | Cl | $CH_3$ | H | $—(CH_2)_4—$ | | O | S | $s-C_4H_9—$ | oil | |
| I-1-c-25 | Cl | Cl | $CH_3$ | H | H | $i-C_3H_7$ | O | S | $t-C_4H_9—CH_2—$ | oil | |
| I-1-c-26 | Cl | Cl | $CH_3$ | H | H | $i-C_3H_7$ | O | S | $s-C_4H_9—$ | 84–86 | |
| I-1-c-27 | Cl | Br | $CH_3$ | | $—(CH_2)_2—CHCH_3—(CH_2)_2—$ | H | O | O | $C_2H_5—$ | >220 | β |
| I-1-c-28 | Cl | Br | $CH_3$ | | $—(CH_2)_2—O—(CH_2)_2—$ | H | O | O | $C_2H_5—$ | >220 | — |
| I-1-c-29 | Cl | Br | $CH_3$ | | $—(CH_2)_2—O—(CH_2)_2—$ | H | O | O | $i-C_4H_9—$ | >220 | — |
| I-1-c-30 | Cl | $CH_3$ | Cl | $CH_3$ | $CH_3$ | H | O | O | $i-C_4H_9—$ | 132 | — |
| I-1-c-31 | Cl | $CH_3$ | Cl | H | H | $i-C_3H_7$ | O | S | $t-C_4H_9—$ | 141 | — |
| I-1-c-32 | Cl | $CH_3$ | Cl | H | $—CH_2—CHCH_3—CHCH_3—$ | | O | S | $t-C_4H_9—$ | 160 | — |

[a]The compound was obtained by chromatographic separation of a mixture of α and β isomers on silica gel using methylene chloride/ethyl acetate 2:1 as the eluent.

Example (I-1-d-1)

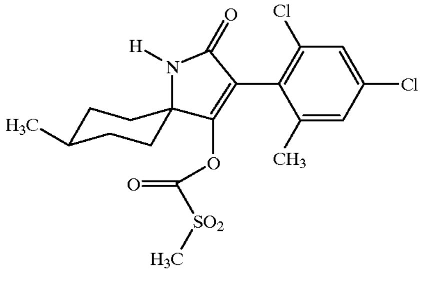

0.93 ml (0.012 mmol) of methanesulphonyl chloride in 5 ml of absolute methylene chloride is added dropwise at 0° C. to 10° C. to 4.08 g of the compound of Example I-1-a-4 and 1.7 ml (0.012 mol) of triethylamine in 70 ml of absolute methylene chloride, and the mixture is stirred at room temperature until the reaction has ended (TLC check). The mixture is washed 2× using 50 ml of 0.5 N NaOH, dried and concentrated, and the residue is recrystallized from methyl tert-butyl ether (MTB ether)/n-hexane.

Yield: 2.80 g (52% of theory), m.p.: 211° C.

Example (I-1-f-1)

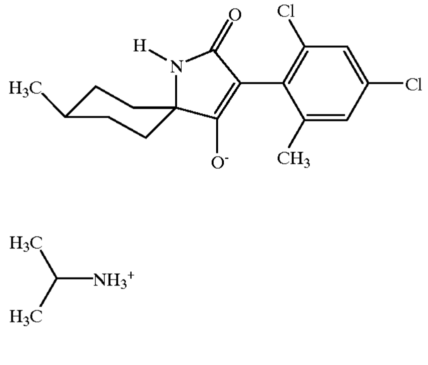

0.85 ml (0.01 mol) of anhydrous isopropylamine is added to 2.04 g of the compound of Example I-1-a-4 in 40 ml of MTB ether and the mixture is stirred for 10 minutes at room temperature. It is subsequently evaporated to dryness in vacuo.

Yield: 2.20 g (91% of theory), m.p.: >220° C.

Example (II-1)

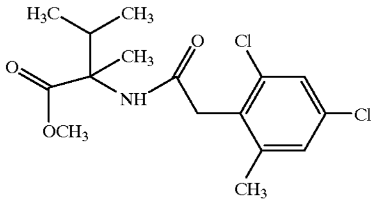

30.8 g of the compound of Example (XXI-1) are carefully added dropwise at 30 to 40° C. to 48.4 g (0.493 mol) of concentrated sulphuric acid and the mixture is stirred for 2 hours at this temperature. 67 ml of absolute methanol are then added dropwise in such a way that an internal temperature of approximately 40° C. is established, and the mixture is stirred for a further 6 hours at 40 to 70° C.

For working-up, the mixture is poured onto 0.48 kg of ice and extracted using methylene chloride, and the methylene chloride phase is washed using aqueous sodium hydrogen carbonate solution, dried and evaporated. The crude product is recrystallized from MTB ether/n-hexane.

Yield: 25.1 g (73% of theory), m.p.: 114° C.

Example (II-2)

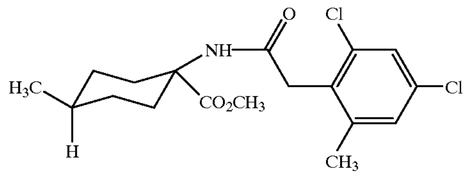

26.3 g (0.12 mol) of 2,4-dichloro-6-methyl-phenylacetic acid according to Example (XXV-2) and 17.7 ml (0.24 mol) of thionyl chloride are stirred at 80° C. until the evolution of gas has ended. Excess thionyl chloride is removed in vacuo at 50° C. 50 ml of absolute toluene are then added and the mixture is evaporated once more. The residue is taken up in 100 ml of absolute THF (solution 1).

Solution 1 is added dropwise at 0 to 10° C. to 25.03 g of methyl 4-methylcyclohexylamine-1-carboxylate and 37 ml (0.264 mol) of triethylamine in 250 ml of absolute THF, and the mixture is subsequently stirred for 1 hour at room temperature. It is then filtered with suction, washed with absolute THF and evaporated. The residue is taken up in methylene chloride, and the mixture is washed with 0.5 N HCl, dried and evaporated. The crude product is recrystallized from MTB ether/n-hexane.

Yield: 34.6 g (77% of theory), m.p.: 145° C.

The following compounds of the formula (II) are prepared analogously to Examples (II-1) and (II-2) or in accordance with the general preparation instructions.

TABLE 13

(II)

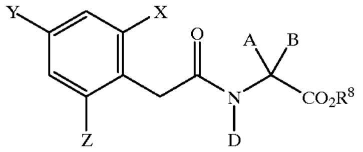

| Example No. | X | Y | Z | B | A | D | $R^8$ | Isomer | M.p. ° C. |
|---|---|---|---|---|---|---|---|---|---|
| II-3 | Cl | Cl | $CH_3$ | | $—(CH_2)_3—CHCH_3—CH_2—$ | H | $CH_3$ | β | 141 |
| II-4 | Cl | Cl | $CH_3$ | | $—(CH_2)_5—$ | H | $CH_3$ | — | 139 |
| II-5 | Cl | Cl | $CH_3$ | | $—(CH_2)_2—O—(CH_2)_2—$ | H | $CH_3$ | — | 129 |
| II-6 | Cl | Cl | $CH_3$ | | $—(CH_2)_2—CHOCH_3—(CH_2)_2—$ | H | $CH_3$ | β | 141 |
| II-7 | Cl | $CH_3$ | Cl | | $—(CH_2)_2—CHCH_3—(CH_2)_2—$ | H | $CH_3$ | β | 93 |
| II-8 | Cl | $CH_3$ | Cl | | $—(CH_2)_3—CHCH_3—(CH_2)_2—$ | H | $CH_3$ | β | 112 |
| II-9 | Cl | $CH_3$ | Cl | | $—(CH_2)_5—$ | H | $CH_3$ | — | 121 |
| II-10 | Cl | $CH_3$ | Cl | | $—(CH_2)_2—O—(CH_2)_2—$ | H | $CH_3$ | — | 146 |
| II-11 | Cl | $CH_3$ | Cl | $i-C_3H_7$ | $CH_3$ | H | $CH_3$ | — | 128 |
| II-12 | Cl | $CH_3$ | Cl | | $—(CH_2)_2—CHOCH_3—(CH_2)_2—$ | H | $CH_3$ | β | 158 |
| II-13 | Cl | Cl | $CH_3$ | $CH_3$ | $CH_3$ | H | $CH_3$ | — | 175 |
| II-14 | Cl | Cl | $CH_3$ | | $—(CH_2)_2—CHOCH_3—(CH_2)_2—$ | H | $CH_3$ | α | 141 |
| II-15 | Br | $CH_3$ | Cl | $CH_3$ | $CH_3$ | H | $CH_3$ | — | 137 |
| II-16 | Br | $CH_3$ | Br | | $—(CH_2)_2—CHCH_3—(CH_2)_2—$ | H | $CH_3$ | β | 203 |
| II-17 | Br | $CH_3$ | Br | | $—(CH_2)_2—CHOCH_3—(CH_2)_2—$ | H | $CH_3$ | β | 149 |
| II-18 | Br | $CH_3$ | Br | | $—(CH_2)_2—O—(CH_2)_2—$ | H | $CH_3$ | — | 172 |
| II-19 | Br | Br | $CH_3$ | | $—(CH_2)_2—CHCH_3—(CH_2)_2—$ | H | $CH_3$ | β | 159 |
| II-20 | Br | Br | $CH_3$ | | $—(CH_2)_2—CHOCH_3—(CH_2)_2—$ | H | $CH_3$ | β | 138 |
| II-21 | Br | Br | $CH_3$ | $CH_3$ | $CH_3$ | H | $CH_3$ | — | 158 |
| II-22 | Br | Br | $CH_3$ | | $—(CH_2)_2—O—(CH_2)_2—$ | H | $CH_3$ | — | 152 |
| II-23 | Br | Cl | $CH_3$ | | $—(CH_2)_2—CHCH_3—(CH_2)_2—$ | H | $CH_3$ | β | 163 |
| II-24 | Br | Cl | $CH_3$ | | $—(CH_2)_3—CHCH_3—CH_2—$ | H | $CH_3$ | β | 139 |
| II-25 | Br | Cl | $CH_3$ | | $—(CH_2)_2—CHOCH_3—(CH_2)_2—$ | H | $CH_3$ | β | 133 |
| II-26 | Br | Cl | $CH_3$ | $CH_3$ | $CH_3$ | H | $CH_3$ | — | 164 |
| II-27 | Br | Cl | $CH_3$ | | $—(CH_2)_2—O—(CH_2)_2—$ | H | $CH_3$ | — | 184 |
| II-28 | Br | Cl | $CH_3$ | $i-C_3H_7$ | $CH_3$ | H | $CH_3$ | — | 102 |
| II-29 | Br | $CH_3$ | Cl | | $—(CH_2)_2—CHCH_3—(CH_2)_2—$ | H | $CH_3$ | β | 141 |
| II-30 | Br | $CH_3$ | Cl | $CH_3$ | $CH_3$ | H | $CH_3$ | — | 127 |
| II-31 | Br | $CH_3$ | Cl | | $—(CH_2)_2—O—(CH_2)_2—$ | H | $CH_3$ | — | 174 |

TABLE 13-continued (II)

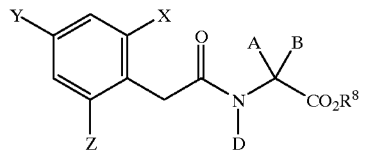

| Example No. | X | Y | Z | B | A | D | $R^8$ | Isomer | M.p. ° C. |
|---|---|---|---|---|---|---|---|---|---|
| II-32 | Cl | Br | $CH_3$ | | $-(CH_2)_2-CHCH_3-(CH_2)_2-$ | H | $CH_3$ | — | 169 |
| II-33 | Cl | Br | $CH_3$ | | $-(CH_2)_2-O-(CH_2)_2-$ | H | $CH_3$ | — | 158 |
| II-34 | Cl | Br | $CH_3$ | | $-(CH_2)_2-CHOCH_3-(CH_2)_2-$ | H | $CH_3$ | β | 158 |
| II-35 | Cl | Cl | $CH_3$ | H | | $-(CH_2)_4-$ | $C_2H_5$ | — | oil |
| II-36 | Cl | Cl | $CH_3$ | H | H | $i-C_3H_7$ | $C_2H_5$ | — | oil |
| II-37 | Cl | $CH_3$ | Cl | H | | $-CH_2-S-(CH_2)_2-$ | $C_2H_5$ | — | oil |
| II-38 | Cl | $CH_3$ | Cl | H | | $-CH_2-CHCH_3-CHCH_3-$ | $C_2H_5$ | — | oil |

Example (XXXI-1)

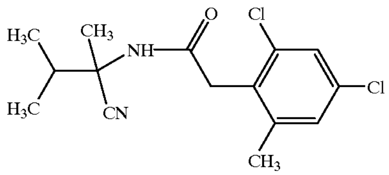

Solution 1 is prepared as described in Example (II-2) starting from 26.3 g of 2,4-dichloro-6-methyl-phenylacetic acid.

Solution 1 is added dropwise at 0 to 10° C. to 13.46 g of 2-amino-2,3-dimethylbutyronitrile and 18.5 ml (0.132 mol) of triethylamine in 150 ml of absolute THF, and the mixture is stirred for a further hour at room temperature. It is then filtered off with suction, washed with absolute THF and evaporated. The residue is taken up in methylene chloride, washed using 0.5 N HCl, dried and evaporated. The crude product is recrystallized from MTB ether/n-hexane.

Yield: 30.8 g (81% of theory), m.p.: 112° C.

The following compounds of the formula (XXXI) were prepared analogously to Example (XXXI-1) or in accordance with the general preparation instructions.

TABLE 14

(XXXI)

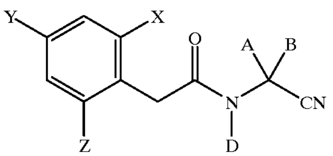

| Example No. | X | Y | Z | A | B | D | M.p. ° C. |
|---|---|---|---|---|---|---|---|
| XXXI-2 | Cl | Cl | $CH_3$ | $-(CH_2)_2-O-(CH_2)_2-$ | | H | 117 |
| XXXI-3 | Cl | $CH_3$ | Cl | $-(CH_2)_2-O-(CH_2)_2-$ | | H | 119 |
| XXXI-4 | Cl | $CH_3$ | Cl | $CH_3$ | $i-C_3H_7$ | H | 71 |
| XXXI-5 | Br | $CH_3$ | Br | $-(CH_2)_2-O-(CH_2)_2-$ | | H | >220 |
| XXXI-6 | Br | Br | $CH_3$ | $-(CH_2)_2-O-(CH_2)_2-$ | | H | 196 |
| XXXI-7 | Br | Cl | $CH_3$ | $-(CH_2)_2-O-(CH_2)_2-$ | | H | 172 |

TABLE 14-continued (XXXI)

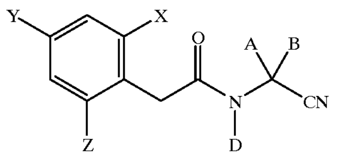

| Example No. | X | Y | Z | A | B | D | M.p. ° C. |
|---|---|---|---|---|---|---|---|
| XXXI-8 | Br | Cl | $CH_3$ | $CH_3$ | $i-C_3H_7$ | H | 128 |
| XXXI-9 | Br | $CH_3$ | Cl | $-(CH_2)_2-O-(CH_2)_2-$ | | H | 139 |
| XXXI-10 | Cl | Br | $CH_3$ | $-(CH_2)_2-O-(CH_2)_2-$ | | H | 171 |

Example (I-2-a-1)

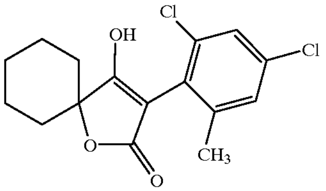

8.42 g (75 mmol) of potassium tert-butylate are introduced into 50 ml of DMF, a solution of 18.6 g (50 mmol) of 1-ethyloxycarbonyl-cyclohexyl 2,4-dichloro-6-methyl-phenylacetate according to Example (III-1) in 50 ml of DMF is added dropwise at 0 to 10° C., and the mixture is stirred overnight at room temperature.

For working-up, the reaction mixture is added dropwise to 500 ml of ice-cold 1 N HCl, and the product which has precipitated is filtered off with suction, washed with water and dried in a vacuum drying oven. For further purification, the crude product is then boiled with n-hexane/acetone.

Yield: 6.71 g (41% of theory) of 3-(2,4-dichloro-6-methyl-phenyl)-5-spirocyclohexyltetronic acid, m.p.: >240° C.

The following compounds of the formula (I-2-a) are obtained analogously or in accordance with the general preparation instructions:

TABLE 15

(I-2-a)

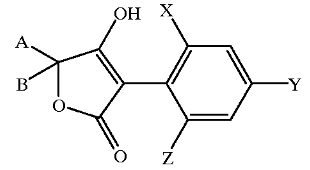

| Example No. | X | Y | Z | A | B | M.p. ° C. |
|---|---|---|---|---|---|---|
| I-2-a-2 | Cl | Cl | $CH_3$ | $—(CH_2)_2—CHCH_3—(CH_2)_2—$ | | >240 |
| I-2-a-3 | Cl | Cl | $CH_3$ | $—(CH_2)_2—CHOCH_3—(CH_2)_2—$ | | oil[1)] |
| I-2-a-4 | Cl | Cl | $CH_3$ | $—(CH_2)_4—$ | | >230 |
| I-2-a-5 | Cl | $CH_3$ | Cl | $—(CH_2)_5—$ | | >260 |
| I-2-a-6 | Cl | $CH_3$ | Cl | $—(CH_2)_2—CHCH_3—(CH_2)_2—$ | | >230 |
| I-2-a-7 | Cl | $CH_3$ | Cl | $—(CH_2)_4—$ | | >260 |
| I-2-a-8 | Br | $CH_3$ | Cl | $—(CH_2)_5—$ | | 284–285 |
| I-2-a-9 | Br | Cl | $CH_3$ | $—(CH_2)_5—$ | | 282 |
| I-2-a-10 | Br | Cl | $CH_3$ | $—(CH_2)_2—O—(CH_2)_2—$ | | 218–219 |
| I-2-a-11 | Cl | Cl | $CH_3$ | $—(CH_2)_2—O—(CH_2)_2—$ | | 230 |
| I-2-a-12 | Cl | $CH_3$ | Cl | $—(CH_2)_2—O—(CH_2)_2—$ | | 280 |
| I-2-a-13 | Br | Br | $CH_3$ | $—(CH_2)_5—$ | | 245 |
| I-2-a-14 | Br | $CH_3$ | Br | $—(CH_2)_5—$ | | 248 |

[1)] $^1H$—NMR, $d_6$-DMSO: $\delta$ = 1.4–2.1(m, 8H); 2.15/2.20(2s, 3H); 3.2/3.55(2m, 1H); 3.24/3.27 (2s, 3H); 7.25–7.50(m, 2H).

Example (I-2-b-1)

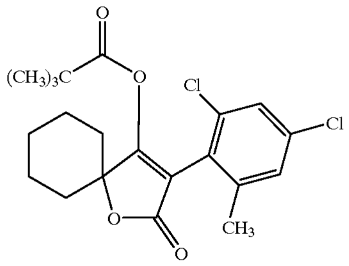

3.27 g (10 mmol) of the compound in accordance with Example I-2-a-1 are introduced into 40 ml of dichloromethane, 1.52 g (15 mmol) of triethylamine are added, a solution of 1.57 g (13 mmol) of pivaloyl chloride in 40 ml of dichloromethane is added dropwise with ice-cooling, and stirring is continued for 1 to 2 h at room temperature. For working-up, the mixture is washed in succession with 10% strength citric acid, 1N NaOH and NaCl solution, and the organic phase is dried over $MgSO_4$ and evaporated. For further purification, the crude product is then stirred with a little petroleum ether.

Yield: 3.6 g (88% of theory) of 4-pivaloyl-oxy-3-(2,4-dichloro-6-methyl-phenyl)-5-spiro-cyclohexyl-tetronic acid, m.p.: 137° C.

The following compounds of the formula (I-2-b) are obtained analogously or in accordance with the general preparation instructions:

TABLE 16

(I-2-b)

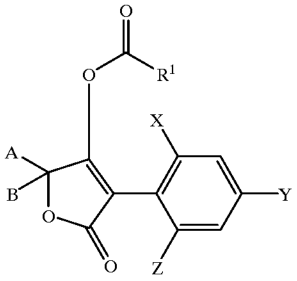

| Example No. | X | Y | Z | A | B | $R^1$ | M.p. ° C. |
|---|---|---|---|---|---|---|---|
| I-2-b-2 | Cl | Cl | $CH_3$ | $—(CH_2)_2—CHCH_3—(CH_2)_2—$ | | $t-C_4H_9—$ | 154 |
| I-2-b-3 | Cl | Cl | $CH_3$ | $—(CH_2)_2—CHOCH_3—(CH_2)_2—$ | | $t-C_4H_9—$ | 147 |
| I-2-b-4 | Cl | Cl | $CH_3$ | $—(CH_2)_4—$ | | $t-C_4H_9—$ | 112 |

TABLE 16-continued (I-2-b)

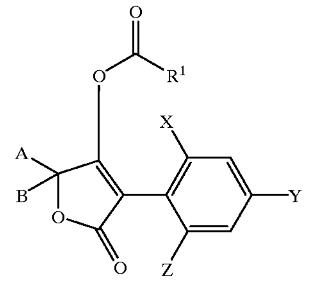

| Example No. | X | Y | Z | A | B | $R^1$ | M.p. ° C. |
|---|---|---|---|---|---|---|---|
| I-2-b-5 | Cl | $CH_3$ | Cl | | $—(CH_2)_5—$ | $t-C_4H_9—$ | 123—128 |
| I-2-b-6 | Cl | $CH_3$ | Cl | | $—(CH_2)_2—CHCH_3—(CH_2)_2—$ | $t-C_4H_9—$ | 125—127 |
| 1-2-b-7 | Cl | $CH_3$ | Cl | | $—(CH_2)_4—$ | $t-C_4H_9—$ | 116-118 |
| I-2-b-8 | Br | Cl | $CH_3$ | | $—(CH_2)_5—$ | $t-C_4H_9—$ | 133 |
| I-2-b-9 | Br | Cl | $CH_3$ | | $—(CH_2)_5—$ | $t-C_4H_9—CH_2—$ | 140 |
| I-2-b-10 | Cl | Cl | $CH_3$ | | $—(CH_2)_2—O—(CH_2)_2—$ | $t-C_4H_9—ch_2$ | 149 |
| I-2-b-11 | Cl | Cl | $CH_3$ | | $—(CH_2)_2—O—(CH_2)_2—$ | $t-C_4H_9—$ | 124 |
| I-2-b-12 | Cl | $CH_3$ | Cl | | $—(CH_2)_2—O—(CH_2)_2—$ | $t-C_4H_9—CH_2—$ | 114 |
| I-2-b-13 | Cl | $CH_3$ | Cl | | $—(CH_2)_2—O—(CH_2)_2—$ | $t-C_4H_9—$ | 133—135 |
| I-2-b-14 | Br | Br | $CH_3$ | | $—(CH_2)_5—$ | $t-C_4H_9—$ | oil |
| I-2-b-15 | Br | Br | $CH_3$ | | $—(CH_2)_5—$ | $t-C_4H_9—CH_2—$ | 113-115 |
| I-2-b-16 | Br | $CH_3$ | Br | | $—(CH_2)_5—$ | $t-C_4H_9—$ | 175 |
| I-2-b-17 | Br | $CH_3$ | Br | | $—(CH_2)_5—$ | $t-C_4H_9—CH_2—$ | 160—162 |

Example (III-1)

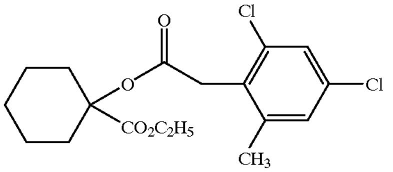

10.95 g (50 mmol) of 2,4-dichloro-6-methyl-phenylacetic acid are introduced into 50 ml of toluene, 11.9 g (100 mmol) of thionyl chloride are added, and the mixture is stirred at 80° C. until the evolution of hydrogen has ceased and is then evaporated. The crude acid chloride is boiled overnight in 50 ml of toluene together with 8.6 g (50 mmol) of ethyl 1-hydroxy-cyclohexanecarboxylate, and the mixture is subsequently evaporated.

Yield: 18.6 g (quantitative) of 1-ethoxycarbonyl-cyclohexyl 2,4-dichloro-6-methyl-phenylacetate as a colourless oil.

$^1H$ NMR ($CDCl_3$): δ=1.2 (t, 3H); 1.3–2.0 (m, 9H); 2.3 (s, 3H); 3.8 (s, 2H); 4.15 (q, 2H); 7.3 (m, 2H).

The following compounds of the formula (III) are obtained analogously or in accordance with the general preparation instructions:

TABLE 17

(III)

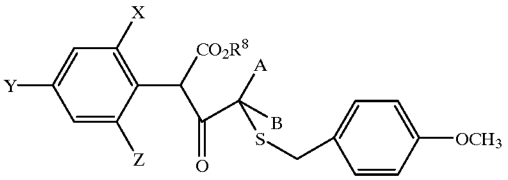

| Example No. | A | B | X | Y | Z | $R^8$ | M.p. ° C. |
|---|---|---|---|---|---|---|---|
| III-2 | | $—(CH_2)_2—CHCH_3—(CH_2)_2—$ | Cl | Cl | $CH_3$ | $C_2H_5$ | oil |
| III-3 | | $—(CH_2)_2—CHOCH_3—(CH_2)_2—$ | Cl | Cl | $CH_3$ | $C_2H_5$ | oil |

TABLE 17-continued (III)

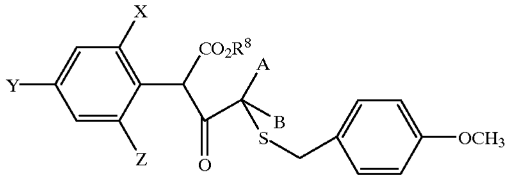

| Example No. | A | B | X | Y | Z | $R^8$ | M.p. ° C. |
|---|---|---|---|---|---|---|---|
| III-4 | | $-(CH_2)_4-$ | Cl | Cl | $CH_3$ | $C_2H_5$ | oil |
| III-5 | | $-(CH_2)_5-$ | Cl | $CH_3$ | Cl | $C_2H_5$ | oil |
| III-6 | | $-(CH_2)_2-CHCH_3-(CH_2)_2-$ | Cl | $CH_3$ | Cl | $C_2H_5$ | oil |
| III-7 | | $-(CH_2)_4-$ | Cl | $CH_3$ | Cl | $C_2H_5$ | oil |
| III-8 | | $-(CH_2)_5-$ | Br | $CH_3$ | Cl | $C_2H_5$ | oil |
| III-9 | | $-(CH_2)_5-$ | Br | Cl | $CH_3$ | $C_2H_5$ | oil |
| III-10 | | $-(CH_2)_5-$ | Br | $CH_3$ | Br | $C_2H_5$ | oil |
| III-11 | | $-(CH_2)_5-$ | Br | Br | $CH_3$ | $C_2H_5$ | oil |
| III-12 | | $-(CH_2)_2-O-(CH_2)_2-$ | Br | Cl | $CH_3$ | $C_2H_5$ | oil |
| III-13 | | $-(CH_2)_2-O-(CH_2)_2-$ | Cl | Cl | $CH_3$ | $C_2H_5$ | oil |
| III-14 | | $-(CH_2)_2-O-(CH_2)_2-$ | Cl | $CH_3$ | Cl | $C_2H_5$ | oil |

Example (I-3-a-1)

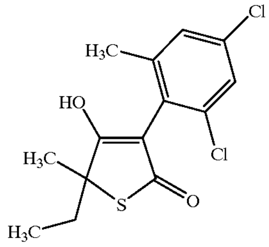

10.8 g (23 mmol) of the compound in accordance with Example (IV-1) are refluxed for 5 hours in 25 ml of trifluoroacetic acid and 50 ml of toluene. The mixture is concentrated to dryness, the residue is treated with 120 ml of water and 40 ml of MTB ether, and NaOH is added until a pH of 14 is reached. The mixture is extracted twice using MTB ether. The aqueous phase is then acidified and extracted 3 times using MTB ether. The organic phase is dried and concentrated, and the residue is stirred with cyclohexane and filtered with suction.

Yield: 0.60 g (8% of theory), m.p.: 222° C.

The following compounds of the formula (I-3-a) were obtained analogously or in accordance with the general preparation instructions:

TABLE 18

(I-3-a)

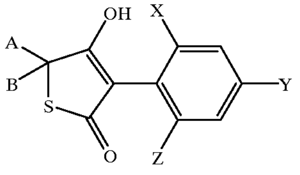

| Example No. | X | Y | Z | A | B | M.p. ° C. |
|---|---|---|---|---|---|---|
| I-3-a-2 | Cl | $CH_3$ | Cl | | $-(CH_2)_5-$ | >250 |
| I-3-a-2 | Cl | Cl | $CH_3$ | | $-(CH_2)_5-$ | >230 |

Example (I-3-b-1)

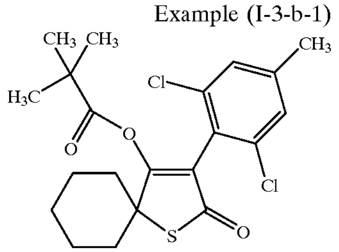

1 g (2.9 mmol) of the compound in accordance with Example (I-3-a-2) are introduced into 12 ml of absolute methylene chloride, and 0.6 ml (1.5 eq.) of triethylamine are added. A solution of 0.47 ml (0.45 g, 3.77 mmol) of pivaloyl chloride in 3 ml of absolute methylene chloride is added dropwise with ice-cooling. The batch is stirred at room temperature for 1 to 2 hours. Due to the incomplete reaction, 0.3 ml of triethylamine and 0.24 ml of acid chloride are additionally metered in. The mixture is subsequently washed twice using 10% strength citric acid, and the combined aqueous phases are extracted using methylene chloride. The combined organic phases are washed twice using 1 N NaOH and the aqueous phases are extracted using methylene chloride. The combined organic phases are dried and concentrated. The residue is stirred into petroleum ether, filtered off with suction and dried.

Yield: 0.70 g (56% of theory), m.p.: 100–108° C.

Example (I-3-c-1)

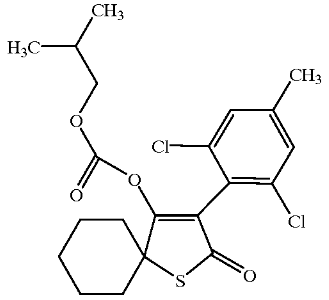

1 g (2.9 mmol) of the compound in accordance with Example (I-3-a-2) are introduced into 12 ml of absolute methylene chloride, and 0.6 ml (1.5 eq.) of triethylamine are added. A solution of 0.49 ml (0.51 g, 3.77 mmol) of isobutyl chloroformate in 3 ml of absolute methylene chloride is added dropwise with ice-cooling. The batch is stirred for 1 to 2 hours at room temperature. Working-up as in Example (I-3-b-1).

Yield: 0.60 g (47% of theory), m.p.: 174–176° C.

Example (IV-1)

A

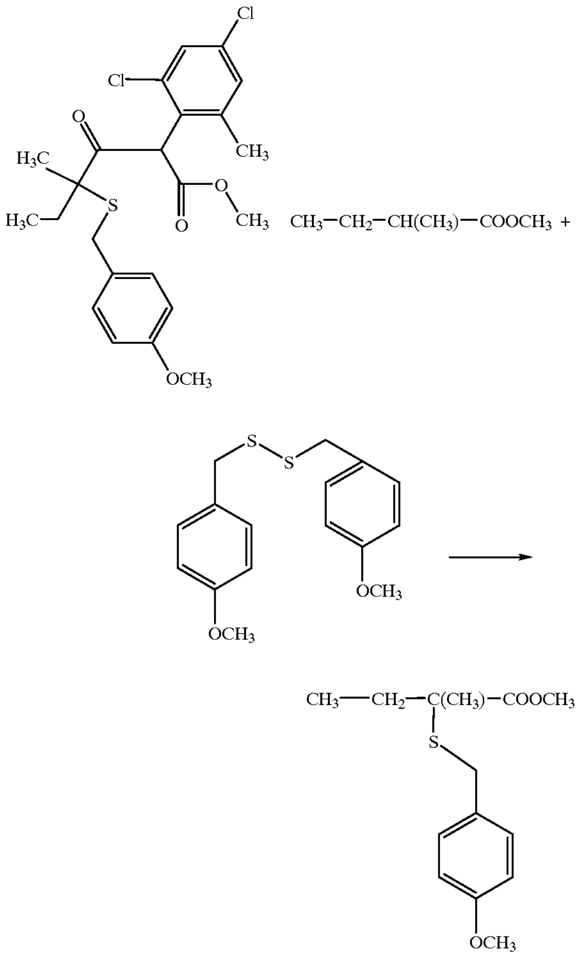

100 ml (160 mmol) of n-butyllithium (1.6 N in n-hexane) are added dropwise at −78° C. to 17.65 g (173.2 mmol) of diisopropylamine in 130 ml of absolute THF, and the mixture is stirred for 20 minutes. 15.5 g (133.2 mmol) of methyl 2-methylbutyrate in 30 ml of absolute THF are then added, and the mixture is stirred for 60 minutes. 40.63 g (133.2 mmol) of bis-(4-methoxybenzyl) disulphide, dissolved in 120 ml of THF, are subsequently added dropwise, and the mixture is allowed to come to room temperature and stirred for 1 hour. 300 ml of MTB ether are added, and the mixture is washed using 150 ml of water, dried and concentrated.

Yield: 35.1 g

B:

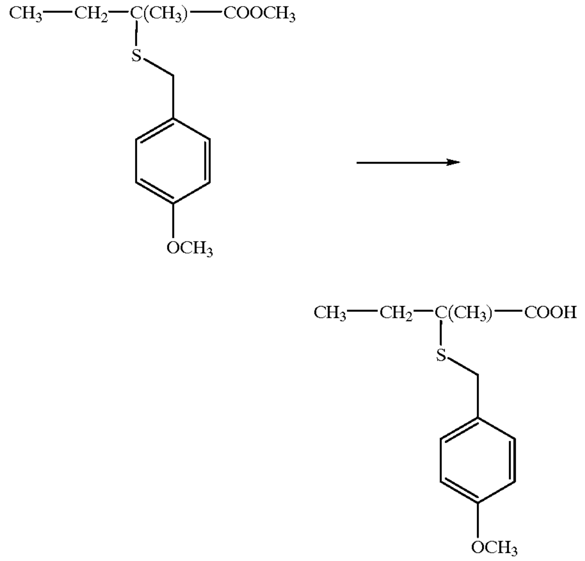

1.5 g (5.6 mmol) of the above compound prepared in accordance with A and 2.0 g of KOH are stirred for 48 hours at 40° C. in 20 ml of methanol. After the mixture has been worked up as usual and the crude product purified by column chromatography (eluent: cyclohexane/ethyl acetate 1/1), 0.6 g (42% of theory) of the acid is obtained.

C:

25 g (98 mmol) of the above carboxylic acid prepared in accordance with B in 107 ml of toluene are treated with one drop of dimethylformamide (DMF) and 17.5 g (147 mmol) of thionyl chloride, and the mixture is stirred at 100° C. until evolution of gas has ceased. The mixture is subsequently evaporated to dryness and the acid chloride dissolved in 40 ml of absolute THF (acid chloride solution).

71.6 ml (118 mmol) of butyllithium (1.6 M in n-hexane) are added dropwise at 0° C. to 13.0 g (129 mmol) of diisopropylamine in 100 ml of THF. After 15 minutes, 25.05 g (108 mmol) of methyl 2,4-dichloro-6-mnethylphenylacetate in 40 ml of THF are added dropwise at 0° C. and the mixture is stirred for 30 minutes. The acid chloride solution prepared above is subsequently added dropwise at 0° C., and the mixture is stirred for one hour at room temperature. 350 ml of MTB ether are added, the mixture is washed twice using 10% strength ammnonium chloride solution, and the organic phase is dried and concentrated. After purification of the crude product by column chromatography (eluent cyclohexane/ethyl acetate 20/1 to 10/1), 11.3 g (25% of theory) of the compound of the formula (IV-1) are obtained.

The compounds of the formula (IV) listed in the table below are obtained analogously or in accordance with the general preparation instructions:

TABLE 19

(IV)

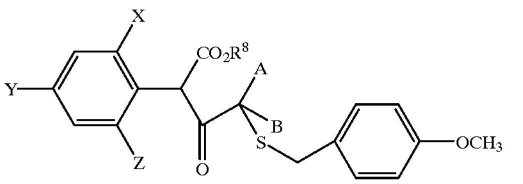

| Example No. | X | Y | Z | A | B | $R^8$ | M.p. ° C. |
|---|---|---|---|---|---|---|---|
| IV-2 | Cl | Cl | $CH_3$ | $-(CH_2)_5-$ | | $CH_3$ | oil |
| IV-3 | Cl | $CH_3$ | Cl | $-(CH_2)_5-$ | | $CH_3$ | 130–135 |

Example (I-5-a-1)

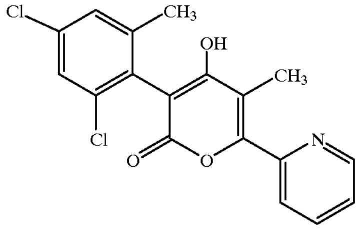

2.6 g (10 mmol) of 2,4-dichloro-6-methyl-phenyl chlorocarbonyl ketene is introduced into 20 ml of absolute toluene, 1.3 g (10 mmol) of ethyl 2-pyridyl ketene is added at 20° C., and the mixture is refluxed for 8 hours. The precipitate is separated off under cold conditions and chromatographed on 200 g of silica gel (35 to 70 μm. (eluent: toluene ethanol 10:1).

1.0 g (28%) of solid of m.p. 96–100° C. are obtained.

The compounds of the formula (1-5-a) listed in the table below are obtained analogously or in accordance with the general preparation instructions:

TABLE 20

(I-5-a)

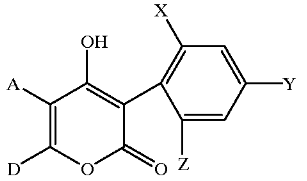

| Example No. | X | Y | Z | A | D | M.p. ° C. |
|---|---|---|---|---|---|---|
| I-5-a-2 | Cl | Cl | $CH_3$ | $CH_3$ | $4\text{-F}-C_6H_4-$ | 194–197 |
| I-5-a-3 | Cl | Cl | $CH_3$ | $CH_3$ | $t\text{-}C_4H_9-$ | 243–245 |
| I-5-a-4 | Cl | $CH_3$ | Cl | $CH_3$ | $4\text{-F}-C_6H_4-$ | 235–238 |
| I-5-a-5 | Cl | $CH_3$ | Cl | | $-(CH_2)_4-$ | 253–256 |
| I-5-a-6 | Cl | $CH_3$ | Cl | $CH_3$ | $t\text{-}C_4H_9-$ | 245–246 |
| I-5-a-7 | Cl | $CH_3$ | Cl | $CH_3$ | cyclopenyl | 260–261 |
| I-5-a-8 | Cl | Cl | $CH_3$ | | $-(CH_2)_4-$ | 295–296 |

Example (V-1)

(V-1)

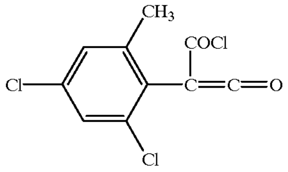

85 ml of thionyl chloride are added at room temperature to 26 g (0.1 mol) of the compound in accordance with Example (XXXV-1) in 115 ml of toluene. The mixture is subsequently refluxed overnight. It is allowed to cool and evaporated to dryness.

Yield: 26.2 g (99% of theory).

$^1H$ NMR (200 MHz, $CDCl_3$): δ=2.35, 2.37 (2s, 3H, Ar—$CH_3$), 7.05–7.45 (m, 2H Ar—H).

Example (V-2)

Starting from the compound in accordance with Example (XXXV-2), 2-(2,6-dichloro-4-methylphenyl) chlorocarbonyl ketene is obtained analogously as an oil.

Example (XXXV-1)

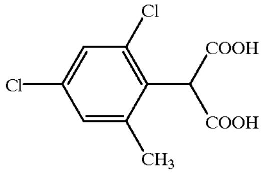

A solution of 6.4 g (0.114 mol) of KOH in 8.6 ml of water is added dropwise to 10 g (0.034 mol) of the compound in accordance with Example (VI-1) in 20 ml of methanol at room temperature. The mixture is subsequently refluxed for 10 hours.

After the mixture has been worked up as usual, 4.7 g (53% of theory) of a solid of m.p.: 176–179° C. are obtained.

Example (XXXV-2)

Starting from the compound in accordance with Example (VI-2), 2-(2,6-dichloro-4-methylphenyl)malonic acid of m.p. 199–207° C. are obtained analogously.

Example (VI-1)

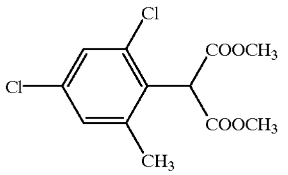

21.7 g (0.7 mol) of 80% pure sodium hydride are added at room temperature to 820 ml of dimethyl carbonate. 125 g (0.54 mol) of methyl 2,4-dichloro-6-methylphenylacetate are subsequently added dropwise at 80 to 90° C., and the mixture is stirred overnight at this temperature. A little methanol is added, and the mixture is poured into ice-water and acidified using 20% strength HCl. The phases are dried and repeatedly extracted with methylene chloride, and the combined organic phases are dried and evaporated.

Yield: 132.1 g (84% of theory), m.p.: 96–99° C.

Example (VI-2)

Dimethyl 2-(2,6-dichloro-4-methylphenyl)-malonate is obtained analogously as an oil.

| | |
|---|---|
| $^1H$ NMR (200 MHz, $CDCl_3$): δ = | 2.31(s, 3H, 4-$CH_3$—Ar), 2.77(s, 6H, $OCH_3$), 5.43(s, 1H, CH), 7.18(s, 1H, Ar—H). |

Example (XXII-1)

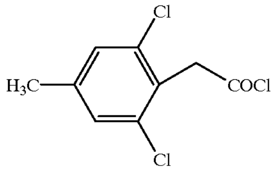

63 g (0.531 mol) of thionyl chloride are added dropwise at room temperature to 38.9 g (0.177 mol) of 2,6-dichloro-4-methylphenylacetic acid, and the mixture is subsequently heated at 70° C. until the evolution of gas has ceased. Excess thionyl chloride is distilled off in vacuo, and the residue is distilled under a high vacuum.

37.8 g (92% of theory) of the phenylacetyl chloride (XXII-1) of b.p.$_{0.06\text{-}0.03\ mbar}$ 109–115° C. are obtained.

The compounds of the formula (XXII) listed in the table below were prepared analogously or in accordance with the general preparation instructions:

TABLE 21

(XXII)

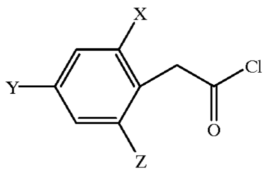

| Example No. | X | Y | Z | b.p. ° C. | mbar |
|---|---|---|---|---|---|
| XXII-2 | Cl | Cl | $CH_3$ | 108–116 | 0.07 |
| XXII-3 | Br | $CH_3$ | Cl | 124 | 0.35 |
| XXII-4 | Br | Br | $CH_3$ | 136 | 0.39 |

All the other acid chlorides which were employed for the synthesis of the compounds (II), (III) and (XXXI) were employed in the form of crude products and not characterized in greater detail.

Example (XXV-1)

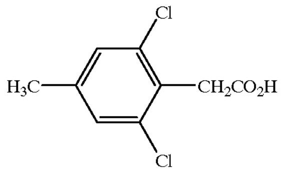

228.6 g (0.98 mol) of the compound of Example (XXVI-1) (94% pure) are added dropwise at room temperature to a mixture of 88.51 g (1.58 mol) of KOH in 115 ml of water and 230 ml of methanol, and the mixture is refluxed for 5 hours. After cooling, it is diluted with 300 ml of water and extracted using ethyl acetate. The aqueous phase is acidified using semiconcentrated hydrochloric acid, and the precipitate is filtered off with suction and dried.

Yield: 183 g (90% of theory), m.p.: 201–203° C.

The compounds of the formula (XXV) listed in the table below were obtained analogously or in accordance with the general preparation instructions:

TABLE 22

(XXV)

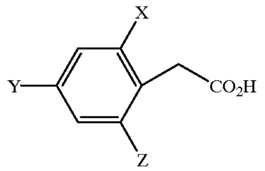

| Example No. | X | Y | Z | M.p. ° C. |
|---|---|---|---|---|
| XXV-2 | Cl | Cl | $CH_3$ | 191–193 |
| XXV-3 | Br | Cl | $CH_3$ | 187–189 |
| XXV-4 | Br | Br | $CH_3$ | 196–198 |
| XXV-5 | Br | $CH_3$ | Br | 206–208 |
| XXV-6 | Br | $CH_3$ | Cl | 208–210 |
| XXV-7 | Cl | Br | $CH_3$ | 188–190 |

Example (XXVI-1)

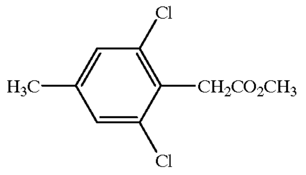

740 ml of a 30% strength solution of sodium methylate in methanol are added dropwise at room temperature to a solution of 283.5 g (0.97 mol) of the compound in accordance with Example (XXVII-1) in 410 ml of methanol, the mixture is refluxed for 5 hours and cooled to room temperature, and 110 ml of concentrated sulphuric acid are added dropwise. The mixture is refluxed for one hour, the methanol is distilled off, and the solid residue is taken up in water. The organic phase is separated off, and the aqueous phase is extracted twice using 1.5 l of methylene chloride. The combined organic phases are dried over $MgSO_4$ and concentrated.

Yield: 228.6 g of an oil (quantitative yield) of b.p.$_{0.1\ mbar}$ 104–108° C.

The compounds of the formula (XXVI) listed in the table below were obtained analogously or in accordance with the general preparation instructions:

TABLE 23

(XXVI)

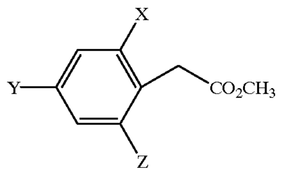

| Example No. | X | Y | Z | M.p. ° C. b.p. | mbar |
|---|---|---|---|---|---|
| XXVI-2 | Cl | Cl | $CH_3$ | 98–110 | 0.5 |
| XXVI-3[1)] | Cl | Br | $CH_3$ | oil | |
| XXVI-4 | Br | $CH_3$ | Cl | 109–112 | 0.1 |
| XXVI-5 | Br | Cl | $CH_3$ | 113–133 | 0.35 |
| XXVI-6 | Br | Br | $CH_3$ | 126–130 | 0.35 |
| XXIV-7[1)] | Br | $CH_3$ | Br | oil | |

[1)]To prepare the acids (XXV), the compounds were employed as crude oils.

Example (XXVII-1)

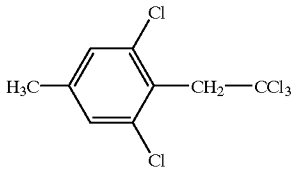

886.5 g (9.135 mol) of 1,1-dichloroethene are added dropwise to a well-cooled mixture of 92.37 g (0.914 mol) of tert-butyl nitrite and 102.5 g (0.715 mol) of anhydrous copper(II) chloride in 360 ml of anhydrous acetonitrile, the mixture being kept at room temperature. A mixture of 106.5 g (0.6 mol) of 2,6-dichloro-4-methylaniline and 600 ml of anhydrous acetonitrile is then added dropwise at a temperature of below 30° C. The mixture is stirred at room temperature until the evolution of gas has ceased, and the mixture is then poured carefully into 2.4 l of 20% strength HCl and extracted repeatedly with a total of 2.5 l of methyl tert-butyl ether (MTBE). The combined organic phases are washed with 20% strength HCl, dried and concentrated. The oil which remains is rectified.

Yield: 72 g (42% of theory), b.p.$_{0.8\ mbar}$ 130–135° C.

The compounds of the formula (XXVII) listed in the table below were obtained analogously or in accordance with the general preparation instructions:

TABLE 24

(XXVII)

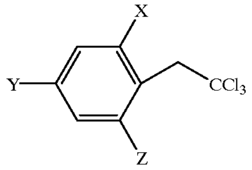

| Example No. | X | Y | Z | M.p. ° C. b.p. | mbar |
|---|---|---|---|---|---|
| XXVII-2 | Cl | Cl | $CH_3$ | 50–52 | |
| XXVII-3 | Cl | Br | $CH_3$ | 79–81 | |
| XXVII-4[1)] | Br | Cl | $CH_3$ | oil | |
| XXVII-5[1)] | Br | Br | $CH_3$ | oil | |
| XXVII-6[1)] | Br | $CH_3$ | Br | oil | |
| XXVII-7[1)] | Br | $CH_3$ | Cl | oil | |

[1)]In the reactions to the esters of the formula (XXVI), the compounds were employed as crude products.

USE EXAMPLES

Example 1

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, a destruction of 100% was caused, after 7 days, for example by the compounds of Preparation Examples (I-3-a-1), (I-3-a-2), (I-3-a-3), (I-5-a-3), (I-5-a-4), (I-2-b-5), (I-2-a-6), (I-1-a-2), (I-1-b-7), (I-1-a-8), (I-1-a-9), (I-1-a-10) and (I-1-a-11) at an exemplary active compound concentration of 0.1% and a destruction of at least 80% by the compounds of Preparation Examples (I-3-b-1) and (I-3-c-1).

Example 2

Plutella Test

Solvent: 7 parts by weight of dimnethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a destruction of 100% was caused, after 7 days, for example by the compounds of Preparation Examples (I-3-a-3), (I-3-b-1), (I-3-a-1), (I-5-a-3), (I-5-a-4), (I-1-a-3), (I-1-a-4), (I-1-b-2), (I-1-c-2), (I-1-a-1) and (I-1-a-7) at an exemplary active compound concentration of 0.1%.

Example 3

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa) are treated by being dipped into the preparation of active compound of the desired concentration and are infested with the green rice leafhopper (Nephotettix cincticeps*) while the seedlings are still moist.

After the specified period of time, the destruction in % is determined. 100% means that all the leafhoppers have been killed; 0% means that none of the leafhoppers have been killed.

In this test, a destruction of 100% was caused, after 6 days, for example by the compounds of Preparation Examples (I-3-a-2), (I-5-a-3), (I-5-a-4), (I-5-a-8), (I-3-b-1), (I-5-a-4), (I-1-a-2), (I-1-a-3), (I-1-a-4), (I-1-c-3), (I-1-a-1), (I-1-b-10), (I-1-c-4), (I-1-b-13), (I-1-a-7), (I-1-a-8), (I-1-a-9) and (I-1-a-11) at an exemplary active compound concentration of 0.1%.

Example 4

Spodoptera Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the fall armyworm (*Spodoptera frugiperda*) while the leaves are still moist.

After the specified period of time, the destruction in % is determined. 100% means that all the caterpillars have been killed; 0% means that none of the caterpillars have been killed.

In this test, a destruction of 100% was caused, after 7 days, for example by the compound of Preparation Example (I-1-b-5) at an exemplary active compound concentration of 0.1%.

Example 5

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the green peach aphid (*Myzus persicae*) are treated by being dipped into the preparation of active compound of the desired concentration.

After the specified period of time, the destruction in % is determined. 100% means that all the aphids have been killed; 0% means that none of the aphids have been killed.

In this test, a destruction of 100% was caused, after 6 days, for example by the compounds of Preparation Examples (I-2-a-5), (I-2-b-5), (I-2-a-6), (I-1-b-7) and (I-1-a-1) at an exemplary active compound concentration of 0.1%.

Example 6

Panonychus Test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Plum trees (*Prunus domestica*) approx. 30 cm high which are severely infested with all stages of the fruit tree spider mite (*Panonychus ulmi*) are sprayed with a preparation of active compound of the desired concentration.

After the specified period of time, the activity in % is determined. 100% means that all the spider mites have been killed; 0% means that none of the spider mites have been killed.

In this test, a destruction of at least 95% was caused, after 7 days, for example by the compounds of Preparation Examples (I-2-a-1), (I-2-b-1), (I-2-a-2), (I-2-b-2), (I-2-b-4) and (I-2-b-5) at an exemplary active compound concentration of 0.004%.

Example 7

Tetranychus Test (OP-resistant/spray Treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Bean plants (*Phaseolus vulgaris*) which are severely infested with all development stages of the greenhouse red spider mite or two-spotted spider-mite (*Tetranychus urticae*) are sprayed with a preparation of active compound of the desired concentration.

After the specified period of time, the destruction in % is determined. 100% means that all the spider mites have been killed; 0% means that none of the spider mites have been killed.

In this test, an activity of 100% was caused, after 7 days, for example by the compounds of Preparation Examples (I-2-b-1), (I-2-b-4) and (I-2-b-5) at an exemplary active compound concentration of 0.004%.

Example 8

Tetranychus Test (OP-resistant/immersion Treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Bean plants (*Phaseolus vulgaris*) which are severely infested with all development stages of the greenhouse red spider mite or two-spotted spider-mite (*Tetranychus urticae*)

are immersed in a preparation of active compound of the desired concentration.

After the specified period of time, the destruction in % is determined. 100% means that all the spider mites have been killed; 0% means that none of the spider mites have been killed.

In this test, an activity of 100% was caused, after 13 days, for example by the compounds of Preparation Examples (I-2-b-2), (I-2-b-6), (I-1-b-7), (I-1-b-10), (I-1-c-4), (I-1-a-7), (I-1-a-11), (I-3-a-2), (I-3-b-1), (I-3-c-1), (I-5-a-4), (I-5-a-3) and (I-5-a-8) at an exemplary active compound concentration of 0.1%.

Example 9

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100% =total destruction

Example 9a

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 1 of water/ha. After three weeks, the degree of damage to the plants is rated in % damage in comparison to the development of the untreated control.

The figures denote:

0%=no action (like untreated control)

100%=total destruction

Pre-emergence Test/greenhouse

| Example No. | g/ha | *Beta vulgaris* | *Alopecurus myosuroides* | *Avena fatua* | *Setaria viridis* | *Sinapis arvensis* |
|---|---|---|---|---|---|---|
| I-1-a-2 | 250 | 0 | 100 | 90 | 100 | — |
| I-1-a-3 | 250 | 0 | 100 | — | 100 | 80 |
| I-1-a-4 | 250 | 0 | 100 | 100 | 100 | 95 |
| I-1-b-2 | 250 | 0 | 100 | 80 | 100 | 70 |
| I-1-b-4 | 250 | 0 | 95 | 80 | 100 | 80 |

-continued

| | | | | | | |
|---|---|---|---|---|---|---|
| I-1-b-7 | 250 | 30 | 95 | 80 | 100 | 100 |
| I-1-b-8 | 250 | 0 | 95 | 50 | 100 | 100 |
| I-1-c-3 | 250 | 30 | 80 | 80 | 100 | 100 |
| I-1-b-10 | 250 | 20 | 100 | 100 | 100 | 100 |
| I-1-b-11 | 250 | 30 | 95 | 40 | 100 | 90 |
| I-1-b-12 | 250 | 20 | 100 | 80 | 100 | 95 |
| I-1-c-4 | 250 | 50 | 100 | 100 | 100 | 100 |
| I-1-b-13 | 250 | 30 | 100 | 80 | 100 | 90 |
| I-1-a-7 | 250 | — | 100 | 90 | 100 | 100 |
| I-1-a-8 | 250 | — | 100 | 40 | 100 | 100 |
| I-1-c-6 | 250 | — | 100 | 100 | 100 | 95 |
| I-1-b-20 | 250 | 30 | 95 | — | 90 | 80 |
| I-1-c-7 | 250 | 0 | 100 | 80 | 100 | 80 |

| Example No. | g/ha | *Beta vulgaris* | *Alopecurus myosuroides* | Amaranthus | *Sinapis arvensis* |
|---|---|---|---|---|---|
| I-3-a-2 | 250 | 0 | — | 60 | — |
| I-3-c-1 | 250 | 0 | — | 70 | — |
| I-5-a-7 | 250 | 0 | 80 | — | 95 |
| I-5-a-1 | 250 | 0 | 80 | — | — |
| I-5-a-1* | 250 | 0 | 80 | — | — |

*Post-emergence Test

Example 10

Test with Resistant Boophilus Microplus/SP Resistant Parkhurst Strain

Test animals: Female adults which have sucked themselves full

Solvent: Dimethyl sulphoxide 20 mg of active compound are dissolved in 1 ml of dimethyl sulphoxide, and lesser concentrations are prepared by dilution with the same solvent.

The test is carried out in 5 applications. 1 $\mu$l of the solutions is injected into the abdomen, and the animals are transferred into dishes and kept in a controlled-environment cabinet. The activity is determined via the inhibition of oviposition. 100% means that no tick has produced eggs.

In this test, an activity of 100% was shown, for example, by the compounds of Preparation Examples (I-2-b-5), (I-2-a-6), (I-1-b-3) and (I-1-a-5) at an exemplary active compound concentration of 20 $\mu$g/animal.

Example 11

Test with Fly Larvae /Development-inhibitory Action

Test animals: All larval stages of Lucilia cuprina (OP-resistant) [Pupae and adults (without contact with active compound)]

Solvent: 35 parts by weight of ethylene glycol monomethyl ether

Emulsifier: 35 parts by weight of nonylphenol polyglycol ether

To produce a suitable formulation, 3 parts by weight of active compound are mixed with 7 parts of the abovementioned solvent/emulsifier mixture, and the resulting emulsion concentrate is diluted with water to the concentration desired in each case.

For each concentration, 30 to 50 larvae are transferred to horsemeat (1 $cm^3$) located in glass tubes and 500 $\mu$l of the test dilution are pipetted onto the meat. The glass tubes are placed into plastic beakers whose bottom is covered with sea sand and kept in a control-environment cabinet (26° C.±1.5° C., 70% relative humidity±10%). The activity is checked after 24 hours and 48 hours (larvicidal action). After the larvae have left the glass tubes (approximately 72 hours), the tubes are removed, and perforated plastic lids are placed on the beakers. After 1½ times the development period (hatching of the control flies), the hatched flies and the pupae/puparia are counted.

The criterion for the action is death in the treated larvae after 48 hours (larvicidal effect) or inhibition of adults hatching from the pupae or inhibition of pupation. The criterion for the in-vitro action of a substance is the inhibition of fly development or a standstill of development prior to the adult stage. 100% larvicidal activity means that all larvae have died after 48 hours. 100% development-inhibitory activity means that no adult flies have hatched.

In this test, an activity of 100% was shown, for example, by the compounds of Preparation Examples (I-2-b-5), (I-2-a-6), (I-1-b-3) and (I-1-a-5) at an exemplary active compound concentration of 1000 ppm.

What is claimed is:

1. Compounds of the formula (I)

(I)

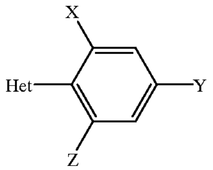

in which

X represents halogen,

Y represents halogen or $C_1$–$C_6$-alkyl,

Z represents halogen or $C_1$–$C_6$-alkyl, where always one of the substituents Y and Z represents halogen, while the other represents allkyl, Het represents (1)

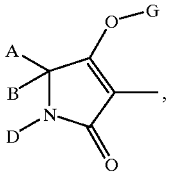

(2)

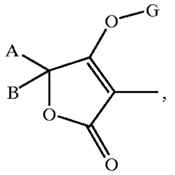

(3)

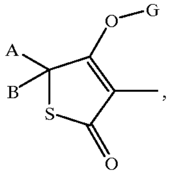

-continued (4)

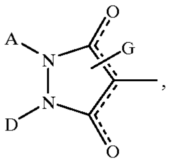

(5)

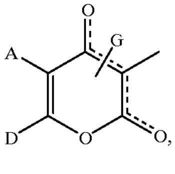

(6)

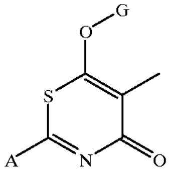

A represents hydrogen, or represents $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl, naphthyl, phenyl-$C_1$–$C_6$-alkyl, naphthyl-$C_1$–$C_6$-alkyl or hetaryl having 5 or 6 ring atoms and one to three hetero atoms from the series consisting of oxygen, sulphur and nitrogen, in each case optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, B represents hydrogen, $C_1$–$C_{12}$-alkyl or $C_1$–$C_8$-alkoxy-$C_1$–$C_6$-alkyl, or A, B and the carbon atom to which they are bonded represent $C_3$–$C_{10}$-cycloalkyl or $C_5$–$C_{10}$-cycloalkenyl in each of which a methylene group is optionally replaced by oxygen or sulphur and which are optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are bonded represent $C_5$–$C_6$-cycloalkyl which is substituted by an alkylenediyl group which optionally contains one or two oxygen and/or sulphur atoms or by an alkylenedioxy or by an alkylenedithioyl group, this group, together with the carbon atom to which it is bonded forming a further five to eight-membered ring, or A, B and the carbon atom to which they are bonded represent $C_3$–$C_8$-cycloalkyl or $C_5$–$C_8$-cycloalkenyl in which two substituents together with the carbon atoms to which they are bonded represent $C_3$–$C_6$-alkanediyl, $C_3$–$C_6$-alkenediyl or $C_4$–$C_6$-alkanedienediyl, each of which is optionally substituted by $C_1$–$C_6$-alkyl, $C_1$–$C_6$-alkoxy or halogen and in which in each case one methylene group is optionally replaced by oxygen or sulphur, G represents hydrogen or represents one of the groups (b)

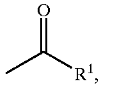

(c)

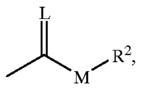

(d)

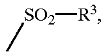

(e)

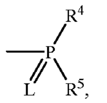

(f)

E or (g)

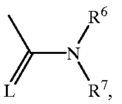

in which

E represents a metal ion equivalent or an ammonium ion,

L represents oxygen or sulphur and

M represents oxygen or sulphur, $R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents 5- or 6-membered hetaryl having one or two hetero atoms from the series consisting of oxygen, sulphur and nitrogen which is optionally substituted by halogen or $C_1$–$C_6$-alkyl, or represents phenoxy-$C_1$–$C_6$-alkyl which is optionally substituted by halogen or $C_1$–$C_6$-alkyl, or represents 5- or 6-membered hetaryloxy-$C_1$–$C_6$-alkyl having one or two hetero atoms from the series consisting of oxygen, sulphur and nitrogen which is optionally substituted by halogen, amino or $C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy, or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ represents $C_1$–$C_8$-alkyl which is optionally substituted by halogen, or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ independently of one another represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_2$–$C_8$-alkenylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, and $R^6$ and $R^7$ independently of one another represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, each of which is optionally substituted by halogen, or represent phenyl or benzyl, each of which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical which is optionally substituted by $C_1$–$C_6$-alkyl and in which one methylene group is optionally replaced by oxygen or sulphur.

2. Compounds of the formula (I) according to claim 1 in which

X represents fluorine, chlorine or bromine,

Y represents fluorine, chlorine, bromine or $C_1$–$C_4$-alkyl,

Z represents fluorine, chlorine, bromine or $C_1$–$C_4$-alkyl, where always one of the radicals Y and Z represents halogen while the other are presents alkyl, Het represents one of the groups (1)

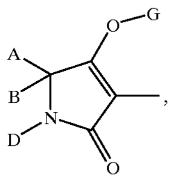

(2)

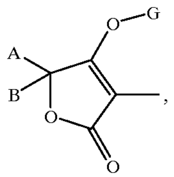

-continued (3)

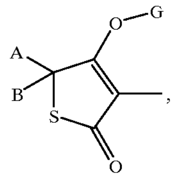

(4)

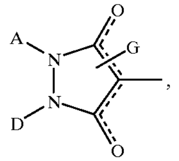

(5)

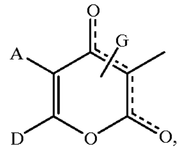

(6)

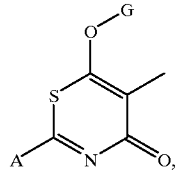

A represents hydrogen, or represents $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl, each of which is optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy and in which one or two methylene groups which are not directly adjacent are optionally replaced by oxygen and/or sulphur, or represents phenyl, furanyl, pyridyl, imidazolyl, triazolyl, pyrazolyl, indolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, B represents hydrogen, $C_1$–$C_{10}$-alkyl or $C_1$–$C_6$-alkoxy-$C_1$–$C_4$-alkyl, or A, B and the carbon atom to which they are bonded represent $C_3$–$C_8$-cycloalkyl or $C_5$–$C_8$-cycloalkenyl in each of which one methylene group is optionally replaced by oxygen or sulphur and which are optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are bonded represent $C_5$–$C_6$-cycloalkyl which is substituted by an alkylenediyl group which optionally contains one or two oxygen or sulphur atoms or by an alkylenedioxy or by an alkylenedithioyl group, this group, together with the carbon atom to which it is bonded forming a further five to seven-membered ring, or A, B and the carbon atom to which they are bonded represent $C_3$–$C_6$-cycloalkyl or $C_5$–$C_6$-cycloalkenyl in which two substituents together with the carbon atoms to which they are bonded represent $C_3$–$C_5$-alkanediyl, $C_3$–$C_5$-alkenediyl or butadienediyl, each of which is optionally substituted by $C_1$–$C_5$-alkyl, $C_1$–$C_5$-alkoxy, fluorine, chlorine or bromine and in which in each case one methylene group is optionally replaced by oxygen or sulphur, G represents hydrogen or represents one of the groups (b)

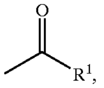

(c)

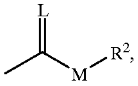

(d)

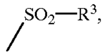

(e)

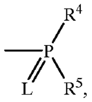

(f)

E or (g)

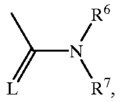

in which

E represents a metal ion equivalent or an ammonium ion,

L represents oxygen or sulphur and

M represents oxygen or sulphur, $R^1$ represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or represents $C_3$–$C_7$-cycloalkyl which is optionally substituted by fluorine, chlorine, $C_1$–$C_5$-alkyl or $C_1$–$C_5$-alkoxy and in which one or two methylene groups which are not directly adjacent are optionally replaced by oxygen and/or sulphur, or represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyrazolyl, thiazolyl, pyridyl, pyrimidyl, furanyl or thienyl, each of which is optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyloxy- $C_1$–$C_5$-alkyl, each of which is optionally substituted by fluorine, chlorine, bromine, amino or $C_1$–$C_4$-alkyl, $R^2$ represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy, or represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy, $R^3$ represents $C_1$–$C_6$-alkyl which is optionally substituted by fluorine or chlorine, or represents phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro, $R^4$ and $R^5$ independently of one another represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, and $R^6$ and $R^7$ independently of one another represent hydrogen, or represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or represent phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical which is optionally substituted by $C_1$–$C_4$-alkyl and in which one methylene group is optionally replaced by oxygen or sulphur.

3. Compounds of the formula (I) according to claim 2, in which

X represents fluorine, chlorine or bromine,

Y represents fluorine, chlorine, bromine, methyl, ethyl, n-propyl or iso-propyl, Z represents fluorine, chlorine, bromine, methyl, ethyl, n-propyl or iso-propyl, where always one of the radicals Y and Z represents halogen while the other represents alkyl, Het represents one of the groups (2)

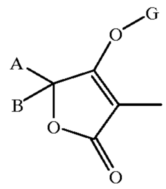

,

A represents hydrogen, or represents $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, each of which is optionally substituted by fluorine or chlorine, or represents $C_3$–$C_6$-cycloalkyl which is optionally substituted by fluorine, chlorine, methyl or methoxy and in which one or two methylene groups which are not directly adjacent are optionally replaced by oxygen and/or sulphur, or represents phenyl, pyridyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, B represents hydrogen, $C_1$–$C_8$-alkyl or $C_1$–$C_4$-alkoxy-$C_1$–$C_2$-alkyl, or A, B and the carbon atom to which they are bonded represent $C_3$–$C_8$-cycloalkyl or $C_5$–$C_8$-cycloalkenyl in each of which one methylene group is optionally replaced by oxygen or sulphur and which are optionally substituted by methyl, ethyl, n-propyl, iso-propyl, butyl, iso-butyl, sec-butyl, tert-butyl, cyclohexyl, trifluoromethyl, methoxy, ethoxy, n-propoxy, iso-propoxy, butoxy, iso-butoxy, sec-butoxy, tert-butoxy, methylthio, ethylthio, fluorine, chlorine or phenyl, or A, B and the carbon atom to which they are bonded represent $C_5$–$C_6$-cycloalkyl which is substituted by an alkylenediyl group which optionally contains an oxygen or sulphur atom or by an alkylenedioxy group, this alkylenediyl or alkylenedioxy group together with the carbon atom to which it is bonded forming a further five to six-membered ring, or A, B and the carbon atom to which they are bonded represent $C_3$–$C_6$-cycloalkyl or $C_5$–$C_6$-cycloalkenyl in which two substituents together with the carbon atoms to which they are bonded represent $C_3$–$C_4$-alkanediyl, $C_3$–$C_4$-alkenediyl or butadienediyl, in each of which one methylene group is optionally replaced by oxygen or sulphur, G represents hydrogen or represents one of the groups (b)

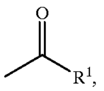

(c)

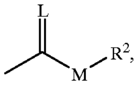

(d)

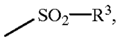

(e)

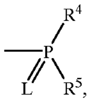

(f)

E or

-continued (g)

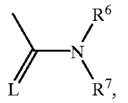

in which

E represents a metal ion equivalent or an ammonium ion,

L represents oxygen or sulphur and

M represents oxygen or sulphur, $R^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is optionally substituted by fluorine or chlorine, or represents $C_3$–$C_6$-cycloalkyl which is optionally substituted by fluorine, chlorine, methyl, ethyl, n-propyl, i-propyl, n-butyl, i-butyl, tert-butyl, methoxy, ethoxy, n-propoxy or iso-propoxy and in which one or two methylene groups which are not directly adjacent are optionally replaced by oxygen and/or sulphur, or represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, or represents benzyl which is optionally substituted by fluorine, chlorine, bromine, methyl, ethyl, n-propyl, i-propyl, methoxy, ethoxy, trifluoromethyl or trifluoromethoxy, or represents furanyl, thienyl or pyridyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl, $R^2$ represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, or represents $C_3$–$C_6$-cycloalkyl which is optionally substituted by fluorine, chlorine, cyano, nitro, methyl, ethyl, n-propyl, iso-propyl, or methoxy, ethoxy, trifluoromethyl or trifluoromethoxy, or represents phenyl or benzyl, each of which is optionally substituted by fluorine, chlorine, methyl, ethyl, n-propyl, iso-propyl or methoxy, cyano, nitro, ethoxy, trifluoromethyl or trifluoromethoxy, $R^3$ represents methyl, ethyl, propyl or isopropyl, each of which is optionally substituted by fluorine or chlorine, or represents phenyl or benzyl, each of which is optionally substituted by fluorine, chlorine, bromine, methyl, ethyl, propyl, isopropyl, tert-butyl, methoxy, ethoxy, isopropoxy, tert-butoxy, trifluoromethyl, trifluoromethoxy, cyano or nitro, $R^4$ and $R^5$ independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, methyl, methoxy, trifluoromethyl or trifluoromethoxy; and $R^6$ and $R^7$ independently of one another represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine or chlorine, or represent phenyl or benzyl, each of which is optionally substituted by fluorine, chlorine, bromine, methyl, methoxy or trinfluoromethyl, or together represent a $C_5$–$C_6$-alkylene radical which is optionally substituted by methyl or ethyl and in which one methylene group is optionally replaced by oxygen or sulphur.

4. Process for the preparation of compounds of the formula (I) according to claim 1, characterized in that (B) compounds of the formula (I-2-a)

(I-2-a)

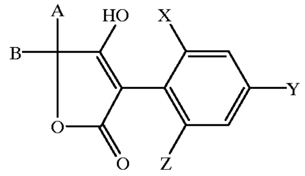

in which

A, B, X, Y and Z have the abovementioned meanings, are obtained when compounds of the formula (III)

(III)

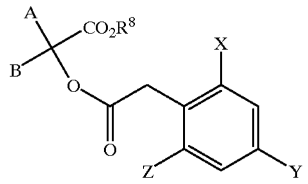

in which

A, B, X, Y, Z and $R^8$ have the abovementioned meanings, are subjected to intramolecular condensation in the presence of a diluent and in the presence of a base, and, if appropriate, the resulting compounds of the formula (I-2-a) and reacted (G)

α) with acid halides of the formula (X)

(X)

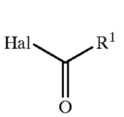

in which $R^1$ has the abovementioned meaning and

Hal represents halogen or

β) with carboxylic anhydrides of the formula (XI)

$R^1$—CO—O—CO—$R^1$ (XI)

in which $R^1$ has the abovementioned meaning, if appropriate in the presence of a diluent and if appropriate in the presence of an acid-binding agent, or (H) with chloroformic esters or chloroformic thioesters of the formula (XII)

$R^2—M—CO—Cl$ (XII)

in which $R^2$ and M have the abovementioned meanings, if appropriate in the presence of a diluent and if appropriate in the presence of an acid-binding agent, or (I)

α) with chloromonothioformic esters or chlorodithioformic esters of the formula (XIII)

(XIII)

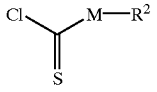

in which

M and $R^2$ have the abovementioned meanings, if appropriate in the presence of a diluent and if appropriate in the presence of an acid-binding agent, or β) with carbon disulphide and subsequently with compounds of the formula (XIV)

$R^2—Hal$ (XIV)

in which $R^2$ has the abovementioned meaning and

Hal represents chlorine, bromine or iodine, if appropiate in the presence of a diluent and if appropiate in the presence of a base, or (J) with sulphonyl chlorides of the formula (XV)

$R^3—SO_2—Cl$ (XV)

in which $R^3$ has the abovementioned meaning, if appropriate in the presence of a diluent and if appropriate in the presence of an acid-binding agent, or (K) with phosphorus compounds of the formula (XVI)

(XVI)

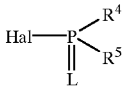

in which

L, $R^4$ and $R^5$ have the abovementioned meanings and Hal represents halogen, if appropriate in the presence of a diluent and if appropriate in the presence of an acid-binding agent, or (L) with metal compounds or amines of the formulae (XVII) or (XVIII)

$Me((OR^{10})_t$ (XVII)

(XVIII)

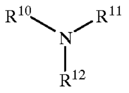

in which

Me represents a mono- or divalent metal, t represents the number 1 or 2 and $R^{10}$, $R^{11}$ and $R^{12}$ independently of one another represent hydrogen or alkyl, if appropriate in the presence of a diluent, or (M)

α) with isocyanates or isothiocyanates of the formula (XIX)

$R^6—N=C=L$ (XIX)

in which $R^6$ and L have the abovementioned meanings, if appropriate in the presence of a diluent and if appropriate in the presence of a catalyst, or β) with carbamoyl chlorides or thiocarbamoyl chlorides of the formula (XX)

(XX)

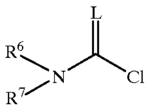

in which

L, $R^6$ and $R^7$ have the abovementioned meanings, if appropriate in the presence of a diluent and if appropriate in the presence of an acid-binding agent.

5. A compound of the formula

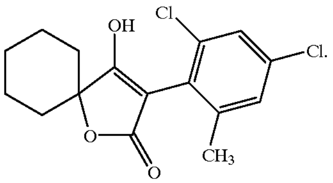

6. A compound of the formula

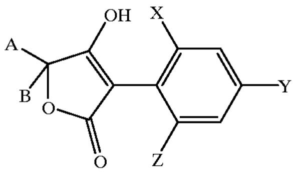

wherein

X represents Cl;

Y represents $CH_3$;

Z represents Cl; and

A and B represent $—(CH_2)_2—CHCH_3—(CH_2)_2$.

7. A compound of the formula

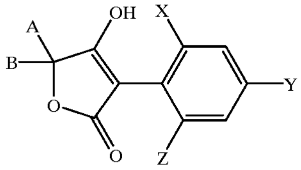

X represents Cl;
Y represents $CH_3$;
Z represents Cl; and
A and B represent $—(CH_2)_4—$.

8. A compound of the formula

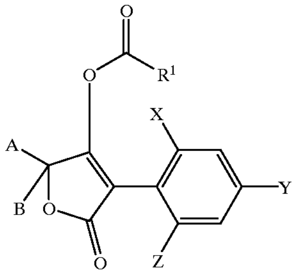

wherein
X represents Cl;

Y represents Cl;
Z represents $CH_3$;
A and B represent $—(CH_2)_2—CHCH_3—(CH_2)_2$; and
$R^1$ represents $t—C_4H_9$.

9. A compound of the formula

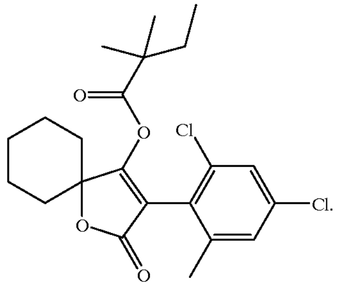

10. Method of combating pests and weeds, characterized in that compounds of the formula (I) according to claim 1 are allowed to act on pests and/or their enviroment or on weeds and/or their enviroment.

11. Process for the preparation of pesticides and herbacides, characterized in that cpmpounds of the formula (I) according to claim 1 are mixed with extenders and/or surface-active agents.

* * * * *